(12) United States Patent
Trent et al.

(10) Patent No.: US 7,816,491 B2
(45) Date of Patent: Oct. 19, 2010

(54) ORDERED BIOLOGICAL NANOSTRUCTURES FORMED FROM CHAPERONIN POLYPEPTIDES

(75) Inventors: Jonathan D. Trent, Watsonville, CA (US); R. Andrew McMillan, San Francisco, CA (US); Hiromi Kagawa, Sunnyvale, CA (US); Chad D. Paavola, Mountain View, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/494,853

(22) PCT Filed: Nov. 8, 2002

(86) PCT No.: PCT/US02/35889

§ 371 (c)(1),
(2), (4) Date: May 6, 2004

(87) PCT Pub. No.: WO03/080796

PCT Pub. Date: Oct. 2, 2003

(65) Prior Publication Data

US 2005/0130258 A1 Jun. 16, 2005

Related U.S. Application Data

(60) Provisional application No. 60/340,538, filed on Nov. 8, 2001.

(51) Int. Cl.
*C07K 14/00* (2006.01)
*A61K 38/00* (2006.01)

(52) U.S. Cl. .......................... 530/350; 514/2; 977/773
(58) Field of Classification Search ........................ None
See application file for complete search history.

(56) References Cited

U.S. PATENT DOCUMENTS

| 5,428,131 | A | 6/1995 | Trent et al. | |
|---|---|---|---|---|
| 6,338,952 | B1 * | 1/2002 | Young | 435/69.7 |
| 6,858,318 | B2 | 2/2005 | Kogiso et al. | |
| 2002/0130353 | A1 | 9/2002 | Lieber et al. | |
| 2003/0078373 | A1 * | 4/2003 | Fersht et al. | 530/350 |
| 2005/0130258 | A1 | 6/2005 | Trent et al. | |

FOREIGN PATENT DOCUMENTS

| EP | 0 881 691 A2 | 2/1998 |
|---|---|---|
| JP | 07-067641 | 3/1995 |
| JP | 11-045990 | 2/1999 |
| JP | 11-204774 | 7/1999 |
| WO | WO 00/77196 | 12/2000 |
| WO | WO 03/080796 | 10/2003 |

OTHER PUBLICATIONS

Weiss and Goloubinoff Journal of Biological Chemistry 270 (23) : 13956-13960 (1995).*
Ursic et al., Molecular Biology of the Cell 5: 1065-1080 (1994), "The essential yeast Tcp1 protein affects actin and microtubules".*
Trent et al., Nature 354(6353): 490-493 (1991), "A molecular chaperone from a thermophilic archaebacterium is related to the eukaryotic protein t-complex polypeptide-1".*
Shpigel et al., Protein Expression and Purification 14: 185-191 (1998), "Production and purification of a recombinant human hsp60 epitope using the cellulose-binding domain in *Escherichia coli*".*
Bosch et al., "Crystal structure of the beta-apical domain of the thermosome reveals structural plasticity in the protrusion region", Journal Molecular Biology 301: 19-25 (Aug. 4, 2000).*
Schoehn et al.,"Three conformations of an archael chaperonin, TF55 from *Sulfolobus shibatae*", Journal of Molecular Biology 296: 813-819 (Feb. 2000).*
Quaite-Randall et al.,"Conformational cycle of the archaesome, a TCP1-like chaperonin from *Sulfolobus shibatae*", Journal of Biological Chemistry 270(48): 28818-28823 (1995).*
Archibald, et al., Recurrent parology in the evolution of archaeal chaperonins, Current Biology, 1999, 1053-1056, 9-18, Elsevier Science Ltd.
Bayburt, et al., Structure, Behavior, and Manipulation of Nanoscale Biologica . . . , Handbook of Nanostructured Materials and Nanotechnology, 2000, 637-710, 5, Academic Press.
Beernink, et al., Random circular permutation leading to chain disruption within and . . . , Protein Science, 2001, 528-537, 10, Cold Spring Harbor Lab. Press.
Berven, et al., Defect-Tolerant Single-Electron Charging at Room Temperature in Metal Nanoparticle Decorated B . . . , Adv. Mater., 2001, 109-113, 13-2, WILEY-VCH-Verlag GmbH.
Brown, et al., a Genetic Analysis of Crystal Growth, J. Mol. Biol. 2000, 725-735, 299, Academic Press.
Brown, Metal-recognition by repeating polypeptides, Nature Biotechnol. 1997, 269-272, 15.
Bruchez, et al., Semiconductor Nanocrystals as Fluorescent Biological Labels, Science, 1998, 2013-2016, 281, AAAS.
Chan, et al., Quantum Dot Bioconjugates for Ultrasensitive Nonisotopic Detection, Science, 1998, 2016-2018, 281, AAAS.
Charlebois, et al., *Sulfolobus* genome: from genomics to biology, Curr. Opin. in Microbio., 1998, 584-588, 1.

(Continued)

*Primary Examiner*—Anand U Desai
(74) *Attorney, Agent, or Firm*—John F. Schipper; Robert M. Padilla

(57) ABSTRACT

The following application relates to nanotemplates, nanostructures, nanoarrays and nanodevices formed from wildtype and mutated chaperonin polypeptides, methods of producing such compositions, methods of using such compositions and particular chaperonin polypeptides that can be utilized in producing such compositions.

17 Claims, 36 Drawing Sheets

OTHER PUBLICATIONS

Dabbousi, et al., (CdSe)ZnS Core-Shell Quantum Dots: Synthesis and Characterization of a Size Series . . . , J. Phys. Chem. B, 1997, 9463-9475, 101, American Chemical Society.

Dat, et al., Mimicking a conformational B cell epitope of the heat shock protein PfHsp70-1 antigen of Pla . . . , Parasite Immunology, 2000. 535-543, 22, Blackwell Science Ltd.

Ditzel, et al., Crystal Structure of the Thermosome, the Archaeal Chaperonin and Homolog of CCT, Cell Press, 1998, 125-138, 93, Cell Press.

Douglas, et al., Nanometer molecular lithography, 1986, Appl. Phys. Lett., 676-678, 48.

Douglas, et al., Virus Particles as Templates for Materials Synthesis, Adv. Mater., 1999, 679-681, 11-8, Wiley-VCH-Verlag GmbH.

Douglas, et al., Host-guest encapsulation of materials by assembled virus protein cages, Nature, 1998, 152-155, 393, Macmillan Publishers Ltd.

Dujardin, et al., Bio-inspired Materials Chemistry, Adv. Mater, 2002, 775-788, 14-11, WILEY-VCH Verlag GMbH.

Ellis, et al., Two-Dimensional Crystallization of the Chaperonin TF55 from the Hyperthermophilic Archaeon Sulfolobus . . . , J. Struc. Biol., 1998, 30-36, 123, Academic Press.

Fenton, et al., GroEL-mediated protein folding, Protein Science, 1997, 743-760, 6, Cold Spring Harbor Laboratory Press.

Furutani, et al., Group II Chaperonin in a Thermophilic Methanoge . . . , J. Biol. Chem., 1998, 28399-28407, 273-43, American Society for Biochemistry & Molecular Biology, Inc.

Galagan, et al., The Genome of M. acetivorans Reveals Extensive Metabolic and Physiological Diversity, Genome Research, 2002, 532-542, 12, Cold Spring Harbor Laboratory Press.

Gerion, et al., Synthesis and Properties of Biocompatible Water-Soluble Silica-Coated CdSe/ZnS Semico . . . , J. Phys. Chem. B, 2001, 8861-8871, 105, American Chemical Society.

Gerstein, et al, Comprehensive assessment of automatic structural alignment against a manual sta . . . , Protein Science, 1998, 445-456, 7, Cold Spring Harbor Laboratory Press.

Gerstein, et al., Using Iterative Dynamic Programming to Obtain Accurate Pairwise and Multiple Al . . . , Proc. of ISMB-96, 1996, 59-67, 96, AAAI Press, Menlo Park, California.

Griesbeck, et al., Reducing the Environmental Sensitivity of Yel . . . , J. Biol. Chem., 2001, 29188-29194, 276-31, American Society for Biochemistry & Molecular Biology, Inc.

Guex, et al., Protein modelling for all, TiBS, 1999, 364, 24.

Guex, et al., SWISS-MODEL and the Swiss-Pdb Viewer: An environment for comparative protein modeling, Electrophoresis, 1997, 2714-2723, 18-15.

Hall, et al., Site-Specific Organization of Gold Nanoparticles by Biomolecular Templating CHEMPHYSCHEM, 2001, 184-186,3, WILEY-VCH-Verlag GmbH.

Harris, et al., Electron Microscopy of the GroEL-GroES Filament, J. Structural Biol., 1995, 68-77, 115, Academic Press, Inc.

Hartl, Molecular chaperones in cellular protein folding, Nature, 1996, 571-580, 381.

Hartl, et al., Molecular Chaperones in the Cytosol: from Nascent Chain to Folded Protein, Science, 2002, 1852-1858, 295.

Heinemann, et al., Circular Permutation of Polypeptide Chains: Implications for Protein Folding and Stability, Prog. Biophys. Mol. Biol., 1995, 121-143, 64.

Horwich, et al., Protein folding in the cell: functions of two families of molecular chaperone, hsp60 and TF55-TCP1, Phil. Trans R. Soc. Lond., 1993, 313-326, 339.

Hulteen, et al., Nanosphere lithography: A materials general fabrication process for periodic p . . . , J. Vac. Sci. Technol. A, 1995, 1553-1558, 13-3, American Vacuum Society.

Iwakura, et al., Systemic circular permutation of an entire protein reveals essential folding elements, Nat. Struct. Biol., 2000, 580-585, 7.

Kagawa, et al., The 60 kDa Heat Schock Proteins in the Hyperthermophilic Archaeon *Sulfolobus shibatae*, J. Mol. Biol., 1995, 712-725, 253, Academic Press Ltd.

Kagawa, et al., The composition, structure and stability of a group II chaperonin are temperature regulated in a hyperthermophilic . . . , Molec Microbio, 2003, 143-156, 48-1.

Karlin, et al., Characterizations of Highly Expressed Genes of Four Fast-Growing Bacteria, J. Bacteriol., 2001, 5025-5040, 183-17, American Society for Microbiology.

Keren, et al., Sequence-Specific Molecular Lithography on Single DNA Molecules, Science, 2002, 72-75, 297.

Klumpp, et al., The thermosome: archetype of group II chaperonins, FEBS Letters, 1998, 73-77, 430, Federation of European Biochemical Societies.

Koeck, et al., Two-dimensional crystals of reconstituted B-subunits of the chaperonin TF55 from *Sulfolobus shibatae*, Biochim. Biophys. Acta, 1998, 40-44, 1429-1.

Kramer, et al., Engineered protein cages for nanomaterial synthesis, J. Am. Chem. Soc., 2004, 13282-13286, 126-41.

Kroger, et al., Polycationic Peptides from Diatom Biosilica That Direct Silica Nanosphere Formation, Science, 1999, 1129-1132, 286.

Labas, et al., Diversity and evolution of the green fluorescent protein family, Proc Natl Acad Sci USA, 2002, 4256-4261, 99.

Lee, et al., Ordering of Quantum Dots Using Genetically Engineered Viruses, Science, 2002, 892-895, 296, AAAS.

Likharev, Single-Electron Devices and Their Applications, Proc. IEEE, 1999, 606-632, 87-4, IEEE.

Lin, et al., The unique hetero-oligomeric nature of the subunits in the catalytic coope . . . , Proc. Natl. Acad. Sci. USA, 1997, 10780-10785, 94, National Academy of Sciences.

Llorca, et al., 3D reconstruction of the ATP-bound form of CCT reveals the asymmetric fold . . . , Nature Structural Biology, , Jul. 1999, 639-642, 6, 7.

Loweth, et al., DNA-Based Assembly of Gold Nanocrystals, 1999, Angew. Chem. Int. Ed., 1808-1812, 38-12, WILEY-VCK Verlag GmbH.

Maier, et al., Plasmonics—A Route to Nanoscale Optical Devices, Adv. Mater., 2001, 1501-1505, 13-19, WILEY-VCH Verlag GmbH.

Maier, et al., Observation of near-field coupling in metal nanoparticle chains using far-field polarization spectroscopy, Phys Rev B, 2002, 65, American Physical Society.

Marco, et al., The molecular chaperone TF55 Assessment of symmetry, FEBS Letters, 1994, 152-155, 341, Federation of European Biochemical Societies.

McMillan, et al., Ordered nanoparticle arrays formed on engineered chaperonin protein templates, Nature Materials, 2002, 247-252, 1.

Miklos, et al., Primary structure and function of a second essential member of the heterooligomeric TCPI chaperon . . . , Proc. Natl. Acad. Sci. USA, Mar. 1994, 2743-2747, 91.

Naik et al., Biomimetic synthesis and patterning of silver nanoparticles, Nature Materials, 2002, 169-172, 1.

Novak, et al., Purification of Molecularly Bridged Metal Nanoparticle Arrays by Centrifugation and Size . . . , Anal. Chem., 2001, 5758-5761, 73-23, American Chemical Society.

Ochman, et al., Genetic Applications of an Inverse Polymerase Chain Reaction, Genetics, 1988, 621-623, 120 Genetics Society of America.

Park, et al., Large area dense nanoscale patterning of arbitrary surfaces, Appl. Phys. Lett., 2001, 257-259, 79-2, American Institute of Physics.

Patterson, et al., Fluorescent protein spectra, J. Cell Sci., 2001, 837-838, 114-5.

Pazirandeh, et al., Metalized nanotubes derived from bacteria, Biomimetics, 1992, 41-50, 1-1.

Peitsch, Protein Modeling by E-mail, Bio/Technology, 1995, 658-660, 13.

Peng, et al., Shape control of CdSe nanocrystals, Nature, 2000, 59-61, 404, Macmillan Magazines Ltd.

Phipps, et al., A novel ATPase complex selectively accumulated upon heat schock is a major cellular . . . , The EMBO Journal, 1991, 1711-1722, 10-7, Oxford University Press.

Richter, et al., Nanoscale Palladium Metallization fo DNA, Adv. Mater., 2000, 507-510, 12.

Sambrook, et al., Plasmid Vectors, Molecular Cloning: A Laboratory Manual, 1989, 1.1-1.110, Cold Spring Harbor Laboratory Press, NY.

Sanger, et al., DNA sequencing with chain-terminating inhibitors, Proc. Natl. Acad. Sci. USA, 1977, 5463-5467, 74-12.

Sato, et al., Single electron transistor using a molecularly linked gold colloidal particle chain, J. Appl. Phys., 1997, 696-701, 82-2, American Institute of Physics.

Shenton, et al., Inorganic-Organic Nanotube Composites from Template Mineralization of Tobacco Mosaic Virus, Adv. Mater., 1999, 253-256, 11.

Shipway, et al., Nanoparticles as structural and functional units in surface-confined architectures, Chem. Commun., 2001, 2035-2045, The Royal Society of Chemistry.

Sleytr, et al., Crystalline Bacterial Cell Surface Layers (S Layers): From Supramolecular Cell Stru . . . , Angew. Chem. Int. Ed., 1999, 1034-1054, 38, WILEY-VCH Verlag GmbH.

Slocik, et al., Monoclonal antibody recognition of histidine-rich peptide encapsulated nanoclusters, Nanoletters, 2002, American Chemical Society.

Thelander, et al., Gold nanoparticle single-electron transistor with carbon nanotube leads, Appl. Phys. Lett., 2001, 2106-2108, 79-13, American Institute of Physics.

Trent, et al., A molecular chaperone from a thermophilic archaebacterium is related to the eukaryotic protein t-complex polypeptide-1, Nature, 1991, 490-493, 354.

Trent, A review of acquired thermotolerance, heat-shock proteins, and molecular chaperones in archaea, FEMs Microbiol Reviews, 1996, 249-258, 18.

Trent, et al., Chaperone filaments The archaeal cytoskeleton?, Proc. Nat. Acad. Sci USA, 1997, 5383-5388, 94, National Academy of Sciences of the USA.

Trent, et al., The Role of Chaperonins in Vivo: The Next Frontier, Annals of the New York Academy of Sciences, 1998, 42-47, 851.

Udono, et al., Heat Shock Protein 70-associated Peptides Elicit Specific Cancer Immunity, J. Exp. Med., 1993, 1391-1396, 178, Rockefeller University Press.

Van Bommel, et al., Organic templates for the generation of inorganic materials, Agnew. Chem. Int. Ed., 2003, 980-999, 42-9, Wiley-VCH Verlag GmbH & Co.

Wall, et al., Effects of overexpressing folding modulators on the in vivo folding of heterologous proteins in *Escherichia coli*, Curr Opin Biotechnol, 1995, 507-516, 6-5.

Wang et al., Icosahedral Virus Particles as Addressable Nanoscale Building blocks, Angew. Chem. Int. Ed., 2002, 459-462, 41-3, WILEY-VCH Verlag GmbH.

Weiss, et al., A Mutant at Position 87 of the GroEL Chaperonin is Affected in Protein Binding and ATP Hydrolysis, J. Biological Chemistry, 13956-13960, 1995, 270-23.

Whaley, et al., Selection of peptides with semiconductor binding specificity for directed nanocrystal assembly, 2000, Nature 405, 665-668, Macmillan Magazines Ltd.

Xia et al., Monodispersed Colloidial Spheres: Old Materials With New Applications, Adv. Mater., 2000, 693-713, 12.

Xu, Z. et al., The crystal structure of the assymetric GroEL-GroES-(ADP)7 chaperonin complex, Nature, 1997, 741-750, 388, Macmillan Publishers Ltd.

Yamishita, Fabrication of a two-dimensional array of nano-particles using ferritin molecule, Thin Solid Films, 2001, 393, 12-18, Elsevier Science B.V.

Yaoi, et al., Chaperonin Filaments: Their Formation and an Evaluation of Methods for Studyi . . . , Archives of Biochemistry and Biophysics, 1998, 55-62, 356-1, Academic Press.

Zhirnov et al., New Frontiers: Self-Assembly and Nanoelectronics, Computer, 2001, 34-43, IEEE.

Zrenner, A. et al., Coherent properties of a two-level system based on a quantum-dot photodiode, Nature, 2002, 612-614, 418, Nature Publishing Group.

Jiang, et al., Formation of Huge Rotaxane by Encapsulating Luminescent Dendrimer Rod in Na . . . , Chemical Society of Japan, 80th Fall Meeting, Sep. 7, 2001, 209, 3BC-07.

Ishii, et al., Novel Protein-Forming Nanocluster Hybrid System: Stabilization of CdS Nanoc . . . , Chemical Society of Japan, 80th Fall Meeting, Sep. 7, 2001, 222, 1C1-04.

Office Action dated Nov. 16, 2007, from continuation-in-part case, U.S. Appl. No. 11/194,991, filed Aug. 1, 2005.

Bosch, et al., Crystal structure of the beta-apical domain of the thermosome reveals structural plasticity in the protrusion region, J. Molecular Bio., Aug. 4, 2000, 19-25, 301.

USPTO Office Action in CIP U.S. Appl. No. 11/194,994, mailing date: Jul. 9, 2008, 14pages.

Response to USPTO Office Action, mailing date: Jul. 9, 2008, in a CIP U.S. Appl. No. 11/194,994, 23 pages. Response filed Jan. 9, 2009.

USPTO Office Action, mailing date Apr. 3, 2009, in a CIP U.S. Appl. No. 11/194,994, 9 pages.

Nonfinal Rejection mailed Oct. 19, 2009 in related U.S. Appl. No. 11/653,479, filed Jan. 8, 2007.

* cited by examiner

Section 18

| | | 579 | | | | 590 | | | | | | 606 |
|---|---|---|---|---|---|---|---|---|---|---|---|---|
| TF55 beta – S. shibatae | (534) | K G G S E P G G K K E K E E K S S E D – – – – – – – – – – |
| GroEL – E. coli | (526) | K – – – – – N D A A D L G A A G G M G G M G G M M |
| thermosome beta – T. acidophilum | (525) | S S S S S N P P K S G S S S E S S E D – – – – – – – |
| cyanobacterial HSP60 synechococcus | (526) | E P – – – – K E K A P A G A G G G M G D F D Y – – – |
| HSP60-4 M. acetivorans | (536) | – – – – – – – – – – – – – – – – – – – – – – – – – – |
| HSP65 – M. tuberculosis | (523) | E – – – – – K E K A S V P G G G D M G G M D F – – – |
| thermosome alpha – A. pernix | (530) | P K K K E K K K G K T G E E E E G G G S K F E F – – – |
| thermosome alpha – M. mazei | (525) | G G R A A P G G M P G G D M E D M M – – – – – – – |
| mitochondrial HSP60 – A. thaliana | (557) | K D E – – S E S G A A G A G M G G M G G M D Y – – – |
| TCP1 alpha – YEAST | (550) | E P P K E D P H D H – – – – – – – – – – – – – – – – |
| mitochondrial HSP60 – HUMAN | (463) | K E E K D P G M G A M D G M G G M G G M F – – – |
| mitochondrial HSP60 – MOUSE | (551) | K E E K D P G M G A M G G M G G M G G M S M L – – – |
| TCP1 alpha – HUMAN | (536) | E S – K D D K H G S Y E D A V H S G A L N D – – – |
| TCP1 alpha – MOUSE | (536) | E S – K D D K H G S Y E N A V H S G A L D D – – – |
| Consensus | (579) | D A M G |

FIG.2R

LEGEND:
G IDENTICAL RESIDUES EXA.
G BLOCK OF SIMILAR EXA.
G CONSERVATIVE EXA.
G WEAKLY SIMILAR EXA.
G NON-SIMILAR EXA.

```
  1  MAS----------PVLLLKEGTSRTTGRDALRNNILAAKTLAEMLR        Alpha
  1  MATATVATTPEGIPVIILKEGSSRTYGKEALRANIAAVKAIEEALK        Beta
  1  MA------------YLLREGTQRSTGNEVILNNIAVAKILLEMLK         Gamma 37  SSLGPKGLDKMLIDSFGDVTITNDGATIVKDMEIQHPAAKLLVEAA        Alpha
 47  STYGPRGMDKMFVDSLGDITITNDGATILDKMDLQHPTGKLLVQIA        Beta
 34  SSLGPKGLDKMLVEG-QDITITNDGATIVKNMEVQHPTAKLLIETA        Gamma 83  KAQDAEVGDGTTSAVVLAGALLEKAESLLDQNIHPTIIIEGYKKAY        Alpha
 93  KGQDEETADGTKTAVILAGELAKKAEDLLYKEIHPTIVSGYKKAE         Beta
 79  KTVDTEVGDGTTSVVVLAGLLLEKAEDLLNQKIHPTVIIEGYRKAL        Gamma 129  TKALELLPQLGTRIDIRDLNSSVARDTLRKIAFTTLASKFIAEGAE        Alpha
139  EIALKTIQDIAQPVSIND------TDVLRKVALTSLGSKAVAGARE        Beta
125  SSSLELLKSIADKISPED------RKIVHDLVYTTLSSKFFSTEHT        Gamma 175  LNKIIDMVIDAIVNVAEPLPNGGYNVSLDLIKIDKKKGGSIEDSVL        Alpha
179  Y--LADLVVKAVAQVAE-LRGDKWYVDLDNVQIVKKHGGSINDTQL        Beta
165  LEKIINLVIEASLAVLD-KRDGTYDLDIKNIKIVKVNGGEFDDSEL        Gamma 221  VKGLVLDKEVVHPGMPRRVTKAKIAVLDAALEVEKPEISAKISITS        Alpha
222  VYGIVVDKEVVHPGMPKRIENAKIALLDASLEVEKPELDAEIRIND        Beta
210  VNGIVVDKEPTNENMPKRAENVKVMLADFPLKLEKTEISMKLGISD        Gamma 267  PEQIKAFLDEESKYLKDMVDKLASIGANVVICQKGIDDIAQHFLAK        Alpha
268  PTQMHKFLEEENILKEKVDKIAATGANVVICQKGIDEVAQHYLAK         Beta
256  PTQIKGYLDEQTAYVKQMVDKIKAMGVKLFITQKDIDEVASYLMGK        Gamma 313  KGILAVRRVKRSDIEKLEKALGARIISSIKDATPDDLGYAELVEER        Alpha
314  KGILAVRRAKKSDLEKLARATGGRVISNIDELTSQDLGYAALVEER        Beta
302  SGIIALKNVKRSDIELLSRATGAKIASSMKDANESDLGEAKLVEVR        Gamma 359  RVGNDKMVFIEGAKNLKAVNILLRGSNDMALDEAERSINDALHALR        Alpha
360  KVGEDKMVFVEGAKNPKSVSILLRGGLERVVDETERALRDALGTVA        Beta
348  NLGKNKYLFIQSDKA-KAVTVIIKGSNNMVTDEAERSLNDAFNSIR        Gamma 405  NILLEPVILPGGGAIELELAMKLREYARSVGGKEQLAIEAFADALE        Alpha
406  DVIRDGRAVAGGGAVEIEIAKRLRKYAPQVGGKEQLAIEAYANAIE        Beta
393  NLLLEPYIVAGGGAVEEELAKRLRENAGKVPGKEQLAFNAFADALE        Gamma 451  EIPTLAETAGLEAISALMDLRARHAKGLTN-TGVDIIGGKIVDDV         Alpha
452  GLIMLAENAGLDPIDKLMCLRSLHENETNKWYGLNLFTGN-PEDM         Beta
439  EYVSILSETAGMDPISALTEIRHKHANGLKN-AGIDIVKARIYDNM        Gamma 496  YALNIIEPIRVKAQVLKSATEAATAILKIDDLIAAAPLKSEKKGGE        Alpha
497  WKLGVIEPALVKMNAIKAATEAVTLVLRIDDIVAAGKKGGSEPGGK        Beta
484  LELKVIDSLKVKEQVLKSATEAATAILKIDDMIAAAPAKQQPQ---        Gamma 542  GSKEESGGEGGAGTPSLGD                                   Alpha
543  KEKEEKSSE--------D                                    Beta
527  -PQQPNPYL--------G                                    Gamma
```

FIG. 15

```
atg gcc tat tta tta aga gaa gga aca cag aga tct act gga aac gag    48
Met Ala Tyr Leu Leu Arg Glu Gly Thr Gln Arg Ser Thr Gly Asn Glu
1               5                   10                  15
gta ata cta aac aac ata gct gta gcc aaa ata tta ctg gaa atg cta    96
Val Ile Leu Asn Asn Ile Ala Val Ala Lys Ile Leu Leu Glu Met Leu
            20                  25                  30
aag tca agc cta ggt cct aag ggt tta gac aag atg tta gtt gag ggg   144
Lys Ser Ser Leu Gly Pro Lys Gly Leu Asp Lys Met Leu Val Glu Gly
        35                  40                  45
caa gac att aca ata act aat gac ggt gcg aca ata gtt aaa aac atg   192
Gln Asp Ile Thr Ile Thr Asn Asp Gly Ala Thr Ile Val Lys Asn Met
    50                  55                  60
gaa gtg cag cat cct act gca aaa tta ctc att gaa acc gct aaa act   240
Glu Val Gln His Pro Thr Ala Lys Leu Leu Ile Glu Thr Ala Lys Thr
65                  70                  75                  80
gtt gat acc gag gta gga gat ggg aca act tca gta gtc gtt ctt gcc   288
Val Asp Thr Glu Val Gly Asp Gly Thr Thr Ser Val Val Val Leu Ala
                85                  90                  95
ggg tta cta tta gaa aaa gct gag gat ttg ctg aat cag aag atc cat   336
Gly Leu Leu Leu Glu Lys Ala Glu Asp Leu Leu Asn Gln Lys Ile His
            100                 105                 110
cca act gtc ata ata gaa ggt tat agg aag gct cta agt tca tca tta   384
Pro Thr Val Ile Ile Glu Gly Tyr Arg Lys Ala Leu Ser Ser Ser Leu
        115                 120                 125
gaa ttg tta aaa agt att gca gat aag att agt cca gaa gat agg aag   432
Glu Leu Leu Lys Ser Ile Ala Asp Lys Ile Ser Pro Glu Asp Arg Lys
    130                 135                 140
ata gtt cac gat cta gta tat act cta tcg agt aag ttc ttc tca       480
Ile Val His Asp Leu Val Tyr Thr Thr Leu Ser Ser Lys Phe Phe Ser
145                 150                 155                 160
aca gag cat act cta gag aag ata ata aat cta gtt att gaa gct tca   528
Thr Glu His Thr Leu Glu Lys Ile Ile Asn Leu Val Ile Glu Ala Ser
                165                 170                 175
ttg gcg gta ttg gat aaa aga gat gga acc tat gat ctg gat att aag   576
Leu Ala Val Leu Asp Lys Arg Asp Gly Thr Tyr Asp Leu Asp Ile Lys
            180                 185                 190
aat ata aag att gta aaa gtc aat ggt ggg gaa ttt gat gat agt gag   624
Asn Ile Lys Ile Val Lys Val Asn Gly Gly Glu Phe Asp Asp Ser Glu
        195                 200                 205
ctt gta aat ggg atc gtt gta gat aag gag ccc acc aat gag aat atg   672
Leu Val Asn Gly Ile Val Val Asp Lys Glu Pro Thr Asn Glu Asn Met
    210                 215                 220
ccg aaa agg gcg gaa aac gtt aag gta atg tta gct gac ttc cca tta   720
Pro Lys Arg Ala Glu Asn Val Lys Val Met Leu Ala Asp Phe Pro Leu
225                 230                 235                 240
aaa ctt gaa aaa acg gaa att agc atg aag ctg gga ata agt gac ccc   768
Lys Leu Glu Lys Thr Glu Ile Ser Met Lys Leu Gly Ile Ser Asp Pro
                245                 250                 255
act cag ata aag gga tac ttg gat gaa caa acg gca tat gtt aag caa   816
Thr Gln Ile Lys Gly Tyr Leu Asp Glu Gln Thr Ala Tyr Val Lys Gln
            260                 265                 270
```

FIG. 16A

```
atg gtg gat aag ata aag gct atg ggc gtt aaa ttg ttt att aca caa       864
Met Val Asp Lys Ile Lys Ala Met Gly Val Lys Leu Phe Ile Thr Gln
        275                 280                 285
aag gac att gat gaa gtc gct tca tat tta atg gga aaa agt ggg ata       912
Lys Asp Ile Asp Glu Val Ala Ser Tyr Leu Met Gly Lys Ser Gly Ile
        290                 295                 300
ata gcg tta aag aac gta aag agg agt gac ata gag tta ctg agt aga       960
Ile Ala Leu Lys Asn Val Lys Arg Ser Asp Ile Glu Leu Leu Ser Arg
305                 310                 315                 320
gct act ggt gcg aaa att gca agt agc atg aaa gac gct aat gag agt      1008
Ala Thr Gly Ala Lys Ile Ala Ser Ser Met Lys Asp Ala Asn Glu Ser
                325                 330                 335
gat tta ggg gaa gct aaa tta gtg gag gtt aga aat tta gga aag aac      1056
Asp Leu Gly Glu Ala Lys Leu Val Glu Val Arg Asn Leu Gly Lys Asn
            340                 345                 350
aaa tac ctc ttc att caa tct gat aaa gct aaa gcg gtg act gta atc      1104
Lys Tyr Leu Phe Ile Gln Ser Asp Lys Ala Lys Ala Val Thr Val Ile
        355                 360                 365
ata aag ggc tcg aat aac atg gta act gat gaa gca gaa agg agt tta      1152
Ile Lys Gly Ser Asn Asn Met Val Thr Asp Glu Ala Glu Arg Ser Leu
370                 375                 380
aat gac gcc ttt aac tcc ata aga aac ttg tta cta gaa ccc tat att      1200
Asn Asp Ala Phe Asn Ser Ile Arg Asn Leu Leu Leu Glu Pro Tyr Ile
385                 390                 395                 400
gtg gct ggt ggt ggt gct gta gag gag gag ttg gct aag agg tta agg      1248
Val Ala Gly Gly Gly Ala Val Glu Glu Glu Leu Ala Lys Arg Leu Arg
                405                 410                 415
gag aac gct gga aaa gtt ccc gga aag gag caa ttg gca ttt aat gca      1296
Glu Asn Ala Gly Lys Val Pro Gly Lys Glu Gln Leu Ala Phe Asn Ala
            420                 425                 430
ttt gcg gat gct ttg gag gag tac gtt tca ata cta tca gaa act gct      1344
Phe Ala Asp Ala Leu Glu Glu Tyr Val Ser Ile Leu Ser Glu Thr Ala
        435                 440                 445
ggc atg gat ccc ata agt gcg tta acc gaa ata aga cat aaa cat gca      1392
Gly Met Asp Pro Ile Ser Ala Leu Thr Glu Ile Arg His Lys His Ala
    450                 455                 460
aac ggg tta aag aat gct ggg att gac ata gtt aag gct aga att tac      1440
Asn Gly Leu Lys Asn Ala Gly Ile Asp Ile Val Lys Ala Arg Ile Tyr
465                 470                 475                 480
gat aac atg ctt gag ctt aaa gta atc gat tct cta aag gtt aag gaa      1488
Asp Asn Met Leu Glu Leu Lys Val Ile Asp Ser Leu Lys Val Lys Glu
                485                 490                 495
caa gtt tta aag agc gcc aca gaa gcc gct act gcg att tta aag atc      1536
Gln Val Leu Lys Ser Ala Thr Glu Ala Ala Thr Ala Ile Leu Lys Ile
            500                 505                 510
gac gac atg ata gca gca gct cct gca aag caa caa cct caa cca caa      1584
Asp Asp Met Ile Ala Ala Ala Pro Ala Lys Gln Gln Pro Gln Pro Gln
        515                 520                 525
cag cca aat cca tac tta ggt ta                                       1607
Gln Pro Asn Pro Tyr Leu Gly
    530                 535
```

FIG. 16B

SEQUENCE LISTING

```
<160> NUMBER OF SEQ ID NOS: 43

<210> SEQ ID NO 1
<211> LENGTH: 552
<212> TYPE: PRT
<213> ORGANISM: Sulfolobus shibatae
<220> FEATURE:
<221> NAME/KEY: MISC_FEATURE
<223> OTHER INFORMATION: TF55 beta subunit

<400> SEQUENCE: 1

Met Ala Thr Ala Thr Val Ala Thr Thr Pro Glu Gly Ile Pro Val Ile
1               5                   10                  15

Ile Leu Lys Glu Gly Ser Ser Arg Thr Tyr Gly Lys Glu Ala Leu Arg
            20                  25                  30

Ala Asn Ile Ala Ala Val Lys Ala Ile Glu Glu Ala Leu Lys Ser Thr
        35                  40                  45

Tyr Gly Pro Arg Gly Met Asp Lys Met Phe Val Asp Ser Leu Gly Asp
    50                  55                  60

Ile Thr Ile Thr Asn Asp Gly Ala Thr Ile Leu Asp Lys Met Asp Leu
65                  70                  75                  80

Gln His Pro Thr Gly Lys Leu Leu Val Gln Ile Ala Lys Gly Gln Asp
                85                  90                  95

Glu Glu Thr Ala Asp Gly Thr Lys Thr Ala Val Ile Leu Ala Gly Glu
            100                 105                 110

Leu Ala Lys Lys Ala Glu Asp Leu Leu Tyr Lys Glu Ile His Pro Thr
        115                 120                 125

Ile Ile Val Ser Gly Tyr Lys Lys Ala Glu Glu Ile Ala Leu Lys Thr
    130                 135                 140
```

```
Ile Gln Asp Ile Ala Gln Pro Val Ser Ile Asn Asp Thr Asp Val Leu
145                 150                 155                 160

Arg Lys Val Ala Leu Thr Ser Leu Gly Ser Lys Ala Val Ala Gly Ala
                165                 170                 175

Arg Glu Tyr Leu Ala Asp Leu Val Val Lys Ala Val Ala Gln Val Ala
            180                 185                 190

Glu Leu Arg Gly Asp Lys Trp Tyr Val Asp Leu Asp Asn Val Gln Ile
        195                 200                 205

Val Lys Lys His Gly Gly Ser Ile Asn Asp Thr Gln Leu Val Tyr Gly
    210                 215                 220

Ile Val Val Asp Lys Glu Val Val His Pro Gly Met Pro Lys Arg Ile
225                 230                 235                 240

Glu Asn Ala Lys Ile Ala Leu Leu Asp Ala Ser Leu Glu Val Glu Lys
                245                 250                 255

Pro Glu Leu Asp Ala Glu Ile Arg Ile Asn Asp Pro Thr Gln Met His
            260                 265                 270

Lys Phe Leu Glu Glu Glu Asn Ile Leu Lys Glu Lys Val Asp Lys
        275                 280                 285

Ile Ala Ala Thr Gly Ala Asn Val Val Ile Cys Gln Lys Gly Ile Asp
    290                 295                 300

Glu Val Ala Gln His Tyr Leu Ala Lys Lys Gly Ile Leu Ala Val Arg
305                 310                 315                 320

Arg Ala Lys Lys Ser Asp Leu Glu Lys Leu Ala Arg Ala Thr Gly Gly
                325                 330                 335

Arg Val Ile Ser Asn Ile Asp Glu Leu Thr Ser Gln Asp Leu Gly Tyr
            340                 345                 350

Ala Ala Leu Val Glu Glu Arg Lys Val Gly Glu Asp Lys Met Val Phe
        355                 360                 365

Val Glu Gly Ala Lys Asn Pro Lys Ser Val Ser Ile Leu Ile Arg Gly
    370                 375                 380

Gly Leu Glu Arg Val Val Asp Glu Thr Glu Arg Ala Leu Arg Asp Ala
385                 390                 395                 400

Leu Gly Thr Val Ala Asp Val Ile Arg Asp Gly Arg Ala Val Ala Gly
                405                 410                 415

Gly Gly Ala Val Glu Ile Glu Ile Ala Lys Arg Leu Arg Lys Tyr Ala
            420                 425                 430

Pro Gln Val Gly Gly Lys Glu Gln Leu Ala Ile Glu Ala Tyr Ala Asn
        435                 440                 445

Ala Ile Glu Gly Leu Ile Met Ile Leu Ala Glu Asn Ala Gly Leu Asp
    450                 455                 460

Pro Ile Asp Lys Leu Met Gln Leu Arg Ser Leu His Glu Asn Glu Thr
465                 470                 475                 480

Asn Lys Trp Tyr Gly Leu Asn Leu Phe Thr Gly Asn Pro Glu Asp Met
                485                 490                 495

Trp Lys Leu Gly Val Ile Glu Pro Ala Leu Val Lys Met Asn Ala Ile
            500                 505                 510

Lys Ala Ala Thr Glu Ala Val Thr Leu Val Leu Arg Ile Asp Asp Ile
        515                 520                 525

Val Ala Ala Gly Lys Lys Gly Gly Ser Glu Pro Gly Gly Lys Lys Glu
    530                 535                 540

Lys Glu Glu Lys Ser Ser Glu Asp
545                 550
```

```
<210> SEQ ID NO 2
<211> LENGTH: 548
<212> TYPE: PRT
<213> ORGANISM: Escherichia coli
<220> FEATURE:
<221> NAME/KEY: MISC_FEATURE
<223> OTHER INFORMATION: GroEL

<400> SEQUENCE: 2

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Ala Val Val Asn Thr Ile Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365
```

-continued

```
Val Ala Lys Leu Ala Gly Gly Val Val Ile Lys Val Gly Ala Ala
    370             375             380
Thr Glu Val Glu Met Lys Glu Lys Lys Ala Arg Val Glu Asp Ala Leu
385             390             395             400
His Ala Thr Arg Ala Ala Val Glu Glu Gly Val Val Ala Gly Gly Gly
                405             410             415
Val Ala Leu Ile Arg Val Ala Ser Lys Leu Ala Asp Leu Arg Gly Gln
            420             425             430
Asn Glu Asp Gln Asn Val Gly Ile Lys Val Ala Leu Arg Ala Met Glu
        435             440             445
Ala Pro Leu Arg Gln Ile Val Leu Asn Cys Gly Glu Glu Pro Ser Val
    450             455             460
Val Ala Asn Thr Val Lys Gly Asp Gly Asn Tyr Gly Tyr Asn Ala
465             470             475             480
Ala Thr Glu Glu Tyr Gly Asn Met Ile Asp Met Gly Ile Leu Asp Pro
                485             490             495
Thr Lys Val Thr Arg Ser Ala Leu Gln Tyr Ala Ala Ser Val Ala Gly
            500             505             510
Leu Met Ile Thr Thr Glu Cys Met Val Thr Asp Leu Pro Lys Asn Asp
        515             520             525
Ala Ala Asp Leu Gly Ala Ala Gly Gly Met Gly Gly Met Gly Gly Met
    530             535             540
Gly Gly Met Met
545

<210> SEQ ID NO 3
<211> LENGTH: 543
<212> TYPE: PRT
<213> ORGANISM: Thermoplasma acidophilum
<220> FEATURE:
<221> NAME/KEY: MISC_FEATURE
<223> OTHER INFORMATION: beta subunit

<400> SEQUENCE: 3

Met Ile Ala Gly Gln Pro Ile Phe Ile Leu Lys Glu Gly Thr Lys Arg
1               5               10              15
Glu Ser Gly Lys Asp Ala Met Lys Glu Asn Ile Glu Ala Ala Ile Ala
            20              25              30
Ile Ser Asn Ser Val Arg Ser Leu Gly Pro Arg Gly Met Asp Lys
        35              40              45
Met Leu Val Asp Ser Leu Gly Asp Ile Val Ile Thr Asn Asp Gly Val
    50              55              60
Thr Ile Leu Lys Glu Met Asp Val Glu His Pro Ala Ala Lys Met Met
65              70              75              80
Val Glu Val Ser Lys Thr Gln Asp Ser Phe Val Gly Asp Gly Thr Thr
            85              90              95
Thr Ala Val Ile Ile Ala Gly Leu Leu Gln Ala Gln Gly Leu
        100             105             110
Ile Asn Gln Asn Val His Pro Thr Val Ile Ser Glu Gly Tyr Arg Met
    115             120             125
Ala Ser Glu Glu Ala Lys Arg Val Ile Asp Glu Ile Ser Thr Lys Ile
130             135             140
Gly Ala Asp Glu Lys Ala Leu Leu Leu Lys Met Ala Gln Thr Ser Leu
145             150             155             160
Asn Ser Lys Ser Ala Ser Val Ala Lys Asp Lys Leu Ala Glu Ile Ser
            165             170             175
```

Tyr Glu Ala Val Lys Ser Val Ala Glu Leu Arg Asp Gly Lys Tyr Tyr
            180                 185                 190

Val Asp Phe Asp Asn Ile Gln Val Lys Lys Gln Gly Gly Ala Ile
        195                 200                 205

Asp Asp Thr Gln Leu Ile Asn Gly Ile Ile Val Asp Lys Glu Lys Val
        210                 215                 220

His Pro Gly Met Pro Asp Val Val Lys Asp Ala Lys Ile Ala Leu Leu
225                 230                 235                 240

Asp Ala Pro Leu Glu Ile Lys Lys Pro Glu Phe Asp Thr Asn Leu Arg
            245                 250                 255

Ile Glu Asp Pro Ser Met Ile Gln Lys Phe Leu Ala Gln Glu Glu Asn
            260                 265                 270

Met Leu Arg Glu Met Val Asp Lys Ile Lys Ser Val Gly Ala Asn Val
            275                 280                 285

Val Ile Thr Gln Lys Gly Ile Asp Asp Met Ala Gln His Tyr Leu Ser
        290                 295                 300

Arg Ala Gly Ile Tyr Ala Val Arg Arg Val Lys Lys Ser Asp Met Asp
305                 310                 315                 320

Lys Leu Ala Lys Ala Thr Gly Ala Ser Ile Val Ser Thr Ile Asp Glu
            325                 330                 335

Ile Ser Ser Ser Asp Leu Gly Thr Ala Glu Arg Val Glu Gln Val Lys
            340                 345                 350

Val Gly Glu Asp Tyr Met Thr Phe Val Thr Gly Cys Lys Asn Pro Lys
        355                 360                 365

Ala Val Ser Ile Leu Val Arg Gly Glu Thr Glu His Val Val Asp Glu
    370                 375                 380

Met Glu Arg Ser Ile Thr Asp Ser Leu His Val Val Ala Ser Ala Leu
385                 390                 395                 400

Glu Asp Gly Ala Tyr Ala Ala Gly Gly Gly Ala Thr Ala Ala Glu Ile
            405                 410                 415

Ala Phe Arg Leu Arg Ser Tyr Ala Gln Lys Ile Gly Gly Arg Gln Gln
        420                 425                 430

Leu Ala Ile Glu Lys Phe Ala Asp Ala Ile Glu Glu Ile Pro Arg Ala
        435                 440                 445

Leu Ala Glu Asn Ala Gly Leu Asp Pro Ile Asp Ile Leu Leu Lys Leu
        450                 455                 460

Arg Ala Glu His Ala Lys Gly Asn Lys Thr Tyr Gly Ile Asn Val Phe
465                 470                 475                 480

Thr Gly Glu Ile Glu Asp Met Val Lys Asn Gly Val Ile Glu Pro Ile
            485                 490                 495

Arg Val Gly Lys Gln Ala Ile Glu Ser Ala Thr Glu Ala Ala Ile Met
        500                 505                 510

Ile Leu Arg Ile Asp Asp Val Ile Ala Thr Lys Ser Ser Ser Ser Ser
        515                 520                 525

Ser Asn Pro Pro Lys Ser Gly Ser Ser Ser Glu Ser Ser Glu Asp
    530                 535                 540

<210> SEQ ID NO 4
<211> LENGTH: 544
<212> TYPE: PRT
<213> ORGANISM: Cyanobacterial synechococcus
<220> FEATURE:
<221> NAME/KEY: MISC_FEATURE
<223> OTHER INFORMATION: Cyanobacterial HSP60

-continued

```
<400> SEQUENCE: 4

Met Ala Lys Arg Ile Ile Tyr Asn Glu Asn Ala Arg Arg Ala Leu Glu
1               5                   10                  15

Lys Gly Ile Asp Ile Leu Ala Glu Ala Val Ala Val Thr Leu Gly Pro
            20                  25                  30

Lys Gly Arg Asn Val Val Leu Glu Lys Lys Phe Gly Ala Pro Gln Ile
        35                  40                  45

Ile Asn Asp Gly Val Thr Ile Ala Lys Glu Ile Glu Leu Glu Asp His
50                  55                  60

Ile Glu Asn Thr Gly Val Ala Leu Ile Arg Gln Ala Ala Ser Lys Thr
65                  70                  75                  80

Asn Asp Ala Ala Gly Asp Gly Thr Thr Thr Ala Thr Val Leu Ala His
                85                  90                  95

Ala Val Val Lys Glu Gly Leu Arg Asn Val Ala Ala Gly Ala Asn Ala
            100                 105                 110

Ile Leu Leu Lys Arg Gly Ile Asp Lys Ala Thr Asn Phe Leu Val Glu
        115                 120                 125

Gln Ile Lys Ser His Ala Arg Pro Val Glu Asp Ser Lys Ser Ile Ala
130                 135                 140

Gln Val Gly Ala Ile Ser Ala Gly Asn Asp Phe Glu Val Gly Gln Met
145                 150                 155                 160

Ile Ala Asp Ala Met Asp Lys Val Gly Lys Glu Gly Val Ile Ser Leu
                165                 170                 175

Glu Glu Gly Lys Ser Met Thr Thr Glu Leu Glu Val Thr Glu Gly Met
            180                 185                 190

Arg Phe Asp Lys Gly Tyr Ile Ser Pro Tyr Phe Ala Thr Asp Thr Glu
        195                 200                 205

Arg Met Glu Ala Val Phe Asp Glu Pro Phe Ile Leu Ile Thr Asp Lys
210                 215                 220

Lys Ile Gly Leu Val Gln Asp Leu Val Pro Val Leu Glu Gln Val Ala
225                 230                 235                 240

Arg Ala Gly Arg Pro Leu Val Ile Ala Glu Asp Ile Glu Lys Glu
                245                 250                 255

Ala Leu Ala Thr Leu Val Val Asn Arg Leu Arg Gly Val Leu Asn Val
            260                 265                 270

Ala Ala Val Lys Ala Pro Gly Phe Gly Asp Arg Arg Lys Ala Met Leu
        275                 280                 285

Glu Asp Ile Ala Val Leu Thr Gly Gly Gln Leu Ile Thr Glu Asp Ala
290                 295                 300

Ala Arg Lys Leu Asp Thr Thr Lys Leu Asp Gln Leu Gly Lys Ala Arg
305                 310                 315                 320

Arg Ile Thr Ile Thr Lys Asp Asn Thr Thr Ile Val Ala Glu Gly Asn
                325                 330                 335

Glu Ala Ala Val Lys Ala Arg Val Asp Gln Ile Arg Gln Ile Glu
            340                 345                 350

Glu Thr Glu Ser Ser Tyr Asp Lys Glu Lys Leu Gln Glu Arg Leu Ala
        355                 360                 365

Lys Leu Ser Gly Gly Val Ala Val Val Lys Val Gly Ala Ala Thr Glu
370                 375                 380

Thr Glu Met Lys Asp Arg Lys Leu Arg Leu Glu Asp Ala Ile Asn Ala
385                 390                 395                 400

Thr Lys Ala Ala Val Glu Glu Gly Ile Val Pro Gly Gly Gly Thr Thr
                405                 410                 415
```

```
Leu Ala His Leu Ala Pro Gln Leu Glu Glu Trp Ala Thr Ala Asn Leu
            420                 425                 430

Ser Gly Glu Glu Leu Thr Gly Ala Gln Ile Val Ala Arg Ala Leu Thr
            435                 440                 445

Ala Arg Leu Lys Arg Ile Ala Glu Asn Ala Gly Leu Asn Gly Ala Val
            450                 455                 460

Ile Ser Glu Arg Val Lys Glu Leu Pro Phe Asp Glu Gly Tyr Asp Ala
465                 470                 475                 480

Ser Asn Asn Gln Phe Val Asn Met Phe Thr Ala Gly Ile Val Asp Pro
                485                 490                 495

Ala Lys Val Thr Arg Ser Ala Leu Gln Asn Ala Ala Ser Ile Ala Ala
            500                 505                 510

Met Val Leu Thr Thr Glu Cys Ile Val Val Asp Lys Pro Glu Pro Lys
            515                 520                 525

Glu Lys Ala Pro Ala Gly Ala Gly Gly Met Gly Asp Phe Asp Tyr
            530                 535                 540
```

<210> SEQ ID NO 5
<211> LENGTH: 535
<212> TYPE: PRT
<213> ORGANISM: Methanosarcina acetivorans
<220> FEATURE:
<221> NAME/KEY: MISC_FEATURE
<223> OTHER INFORMATION: acetivoran HSP60-4

<400> SEQUENCE: 5

```
Met Ala Ser Glu Leu Lys Thr Pro Gly Asn Thr Ser Pro Glu Ser Gln
1               5                   10                  15

Asp Gly Met Ala Lys Leu Ala Arg Thr Ile Arg Asp Lys Ile Leu Ile
            20                  25                  30

Asp Glu Pro Val Lys Glu Glu Leu Ile Asp Gln Leu Glu Arg Ala
            35                  40                  45

Ala Ile Glu Ile Asp Glu Leu Leu Gly Ser Ser Leu Gly Pro Lys Gly
50                  55                  60

Met Asn Lys Ile Ile Val Asn Pro Val Gly Asp Ile Phe Val Thr Ser
65                  70                  75                  80

Asp Gly Lys Val Ile Leu Lys Glu Ile Asp Val Leu His Pro Ile Val
            85                  90                  95

Thr Ser Leu Lys Lys Leu Ala Glu Ser Met Asp Lys Ala Cys Gly Asp
            100                 105                 110

Gly Thr Lys Thr Ala Val Ile Phe Ala Ser Asn Leu Ile Lys Asn Ala
            115                 120                 125

Val Arg Leu Ile Arg Ala Gly Val His Pro Thr Ile Ile Glu Gly
            130                 135                 140

Tyr Glu Leu Ala Met Gln Lys Thr Tyr Glu Met Leu Gln Tyr Ser Ile
145                 150                 155                 160

Arg Gln Ala Ser Glu Glu Asp Ile Arg Thr Thr Ile Met Cys Ser Ala
                165                 170                 175

Thr Gly Lys Gly Ile Glu Arg Gln Gln Ala Gln Ala Val Thr Glu Ile
            180                 185                 190

Ala Leu Lys Val Ile Ser His Leu Ser Glu Lys Gln Ala Gly Arg Ile
            195                 200                 205

Asp Leu Asn Arg Asn Val Lys Ile Leu Lys Lys Gly Gly Pro Glu
            210                 215                 220

Ile Val Ala Ile Glu Gly Leu Ile Met Asp Glu Asn Pro Ala Arg Glu
```

```
                225                 230                 235                 240

Asp Met Pro Lys Ser Tyr Gln Asn Pro Ala Val Leu Ile Thr Asn Tyr
                245                 250                 255

Asp Leu Lys Ile Lys Ser Gly Tyr Leu Asn Pro Gln His Asn Phe Lys
                260                 265                 270

Met Asp Ser Val Gln Thr Ala Leu Leu Phe Glu Glu Arg Lys Lys Gln
                275                 280                 285

Leu Cys Gly Glu Ile Ala Arg Lys Ile Ile Asp Ser Gly Ala Asn Val
        290                 295                 300

Leu Phe Ser Glu Gly Asp Ile Asp Pro Tyr Ile Glu Thr Leu Leu Arg
305                 310                 315                 320

Asp Ser Asn Ile Leu Ala Phe Lys Lys Leu Lys Met Lys Asp Leu Glu
                325                 330                 335

Lys Leu Ala Glu Ala Thr Gly Thr Thr Leu Met Ala Gln Pro Asp Glu
                340                 345                 350

Ile Arg Pro Cys Asp Leu Gly Arg Ala Gly Ser Ile Lys Leu Glu Lys
                355                 360                 365

Lys Asn Gly Glu Asn Phe Val Phe Ile Thr Val Lys Asp Lys Ala Ile
                370                 375                 380

Ala Thr Ile Leu Ile Arg Glu Pro Val Lys Tyr Gly Leu Asp Lys Val
385                 390                 395                 400

Glu Glu Ala Val Asp Asp Ala Leu Asn Asn Ala Ala Phe Leu Arg Lys
                405                 410                 415

Asn Arg Glu Ile Val Asn Gly Gly Ala Ile Glu Phe Glu Leu Ala
                420                 425                 430

His Met Val Arg Leu Phe Ala Ala Thr Gln Thr Gly Lys Arg Gln Leu
                435                 440                 445

Ala Val Gln Ala Tyr Ala Glu Ala Leu Glu Lys Ile Pro Val Ile Leu
        450                 455                 460

Ala Arg Asn Ile Gly Met Asn Glu Ile Asp Ala Met Ala Gln Met Arg
465                 470                 475                 480

Asn Ser Tyr Ala Arg Gly Leu Glu Ala Arg Ile Asp Leu Ser Arg Lys
                485                 490                 495

Val Thr Asp Arg Gly Pro Glu Val Tyr Asp Ser Ala Thr Val Lys Lys
                500                 505                 510

Leu Ala Ile Ile Ala Gly Thr Glu Thr Ala Lys Lys Val Leu Arg Ile
        515                 520                 525

Asp Glu Ile Val Pro Lys Lys
        530                 535

<210> SEQ ID NO 6
<211> LENGTH: 540
<212> TYPE: PRT
<213> ORGANISM: Methanosarcina tuberculosis
<220> FEATURE:
<221> NAME/KEY: MISC_FEATURE
<223> OTHER INFORMATION: tuberculosis HSP65

<400> SEQUENCE: 6

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
                20                  25                  30

Lys Gly Arg Asn Val Val Leu Glu Lys Lys Trp Gly Ala Pro Thr Ile
        35                  40                  45
```

-continued

```
Thr Asn Asp Gly Val Ser Ile Ala Lys Glu Ile Glu Leu Glu Asp Pro
 50                  55                  60

Tyr Glu Lys Ile Gly Ala Glu Leu Val Lys Glu Val Ala Lys Lys Thr
 65                  70                  75                  80

Asp Asp Val Ala Gly Asp Gly Thr Thr Thr Ala Thr Val Leu Ala Gln
                 85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
```

-continued

```
              465                 470                 475                 480
        Val Tyr Glu Asp Leu Leu Ala Ala Gly Val Ala Asp Pro Val Lys Val
                        485                 490                 495

Thr Arg Ser Ala Leu Gln Asn Ala Ala Ser Ile Ala Gly Leu Phe Leu
                        500                 505                 510

Thr Thr Glu Ala Val Val Ala Asp Lys Pro Glu Lys Glu Lys Ala Ser
                        515                 520                 525

Val Pro Gly Gly Gly Asp Met Gly Gly Met Asp Phe
                        530                 535                 540

<210> SEQ ID NO 7
<211> LENGTH: 554
<212> TYPE: PRT
<213> ORGANISM: Aeropyrum pernix
<220> FEATURE:
<221> NAME/KEY: MISC_FEATURE
<223> OTHER INFORMATION: Alpha subunit

<400> SEQUENCE: 7

Met Ala Ala Thr Gly Tyr Pro Val Leu Ile Leu Lys Glu Gly Thr Gln
1               5                   10                  15

Arg Thr Tyr Gly Arg Glu Ala Leu Arg Ala Asn Ile Leu Ala Ala Arg
                20                  25                  30

Val Leu Ala Glu Met Leu Lys Ser Ser Leu Gly Pro Arg Gly Leu Asp
            35                  40                  45

Lys Met Leu Val Asp Ala Phe Gly Asp Ile Thr Val Thr Asn Asp Gly
    50                  55                  60

Ala Thr Ile Val Lys Glu Met Glu Ile Gln His Pro Ala Ala Lys Leu
65                  70                  75                  80

Leu Val Glu Val Ala Lys Ala Gln Asp Ala Val Gly Asp Gly Thr
                85                  90                  95

Thr Ser Val Val Val Leu Ala Gly Ala Leu Leu Glu Lys Ala Glu Lys
            100                 105                 110

Leu Leu Asp Glu Asn Leu His Pro Thr Ile Ile Ile Glu Gly Tyr Thr
        115                 120                 125

Lys Ala Met Glu Glu Ala Leu Arg Leu Val Asp Glu Ala Ala Val Pro
    130                 135                 140

Val Glu Val Glu Asp Asp Ser Val Leu Arg Arg Ile Ala Glu Thr Thr
145                 150                 155                 160

Leu Ala Ser Lys Phe Val Gly Thr Gly Pro Glu Arg Asp Lys Ile Ile
                165                 170                 175

Ser Met Val Ile Asp Ala Ile Arg Thr Val Ala Glu Lys Arg Pro Asp
            180                 185                 190

Gly Gly Tyr Glu Val Asp Leu Asp Tyr Val Lys Ile Glu Lys Lys Lys
        195                 200                 205

Gly Gly Ser Leu Leu Asp Ser Lys Leu Val Arg Gly Ile Val Leu Asp
    210                 215                 220

Lys Glu Val Val His Pro Ala Met Pro Lys Arg Val Glu Asn Ala Lys
225                 230                 235                 240

Ile Leu Val Leu Asp Ala Pro Leu Glu Val Gln Lys Pro Glu Leu Thr
                245                 250                 255

Thr Lys Ile Arg Val Thr Asp Ile Glu Lys Leu Glu Ser Phe Leu Glu
            260                 265                 270

Glu Glu Thr Arg Met Leu Arg Asp Met Val Glu Lys Ile Ala Ala Thr
        275                 280                 285
```

-continued

```
Gly Ala Asn Val Val Ile Thr Gln Lys Gly Ile Asp Glu Val Ala Gln
    290                 295                 300

His Phe Leu Ala Lys Lys Gly Ile Leu Ala Val Arg Arg Val Lys Arg
305                 310                 315                 320

Ser Asp Ile Glu Lys Val Ala Lys Ala Thr Gly Ala Lys Ile Val Thr
                325                 330                 335

Ser Leu Arg Asp Leu Lys Pro Glu Tyr Leu Gly Tyr Ala Glu Leu Val
            340                 345                 350

Glu Glu Arg Lys Val Gly Glu Asp Lys Met Val Phe Ile Glu Gly Ala
        355                 360                 365

Lys Asn Pro Lys Ser Val Thr Ile Leu Leu Arg Gly Ala Asn Asp Met
    370                 375                 380

Leu Leu Asp Glu Ala Glu Arg Asn Ile Lys Asp Ala Leu His Gly Leu
385                 390                 395                 400

Arg Asn Ile Leu Arg Glu Pro Lys Ile Val Gly Gly Gly Ala Val
                405                 410                 415

Glu Val Glu Leu Ala Leu Lys Leu Lys Glu Phe Ala Arg Thr Val Gly
            420                 425                 430

Gly Lys Gln Gln Leu Ala Ile Glu Ala Tyr Ala Glu Ala Leu Glu Thr
        435                 440                 445

Ile Pro Thr Val Leu Ala Glu Ser Ala Gly Met Asp Ala Leu Glu Ala
    450                 455                 460

Leu Leu Lys Leu Arg Ser Leu His Ser Gln Gly Tyr Lys Phe Ala Gly
465                 470                 475                 480

Val Asn Val Leu Glu Gly Lys Ile Glu Glu Asp Met Thr Lys Ile Asn
                485                 490                 495

Val Tyr Glu Pro Val Leu Val Lys Lys Gln Val Ile Lys Ser Ala Ser
            500                 505                 510

Glu Ala Ala Ile Ser Ile Leu Lys Ile Asp Asp Val Ile Ala Ala Ala
        515                 520                 525

Pro Pro Lys Lys Lys Glu Lys Lys Gly Lys Thr Gly Glu Glu Glu Glu
    530                 535                 540

Glu Glu Gly Gly Gly Ser Lys Phe Glu Phe
545                 550
```

```
<210> SEQ ID NO 8
<211> LENGTH: 542
<212> TYPE: PRT
<213> ORGANISM: Aeropyrum mazei
<220> FEATURE:
<221> NAME/KEY: MISC_FEATURE
<223> OTHER INFORMATION: Alpha subunit

<400> SEQUENCE: 8
```

```
Met Ala Ala Gln Pro Ile Phe Ile Leu Arg Glu Gly Ser Lys Arg Thr
1               5                   10                  15

His Gly Ser Asp Ala Gln His Asn Asn Ile Met Ala Ala Lys Ala Val
                20                  25                  30

Ala Glu Ala Val Arg Thr Thr Leu Gly Pro Lys Gly Met Asp Lys Met
            35                  40                  45

Leu Val Asp Ala Met Gly Asp Val Val Ile Thr Asn Asp Gly Ala Thr
        50                  55                  60

Ile Leu Lys Glu Met Asp Ile Glu His Pro Gly Ala Lys Met Ile Val
65                  70                  75                  80

Glu Val Ala Lys Thr Gln Asp Ala Glu Val Gly Asp Gly Thr Thr Thr
                85                  90                  95
```

-continued

Ala Ala Val Leu Ala Gly Glu Leu Leu Thr Lys Ala Glu Asp Leu Leu
        100                 105                 110

Glu Ser Gly Val His Pro Thr Val Ile Ala Ser Gly Tyr Arg Leu Ala
        115                 120                 125

Ala Ile Gln Ala Val Lys Ile Leu Asp Thr Ile Thr Ile Ser Ala Ser
        130                 135                 140

Pro Glu Asp Thr Glu Thr Leu Glu Lys Ile Ala Gly Thr Ala Ile Thr
145                 150                 155                 160

Gly Lys Gly Ala Glu Ser His Lys Ala His Leu Ser Asn Leu Ala Val
                165                 170                 175

Arg Ala Ile Lys Ser Ile Val Glu Lys Asp Glu Asn Gly Lys Ile Thr
                180                 185                 190

Val Asp Ile Glu Asp Val Lys Thr Glu Lys Arg Pro Gly Gly Ser Ile
            195                 200                 205

Lys Asp Ser Glu Ile Val Glu Gly Val Ile Val Asp Lys Glu Arg Val
210                 215                 220

His Thr Gly Met Pro Glu Val Lys Asp Ala Lys Val Leu Leu Leu
225                 230                 235                 240

Ser Val Pro Ile Glu Leu Lys Lys Thr Glu Thr Lys Ala Glu Ile Lys
                245                 250                 255

Ile Thr Thr Pro Asp Gln Met Gln Leu Phe Leu Asp Gln Glu Glu Ala
                260                 265                 270

Met Leu Arg Glu Ile Val Asp Lys Val Ile Asp Thr Gly Ala Asn Val
                275                 280                 285

Val Phe Cys Gln Lys Gly Ile Asp Asp Leu Ala Gln Tyr Tyr Leu Thr
        290                 295                 300

Lys Ala Gly Ile Phe Ala Met Arg Arg Val Lys Lys Ser Asp Met Asp
305                 310                 315                 320

Lys Leu Ser Arg Ala Thr Gly Gly Arg Ile Ile Thr Asn Leu Asp Glu
                325                 330                 335

Ile Asp Glu Ser Asp Leu Gly Tyr Ala Gly Met Val Glu Glu Lys Asp
                340                 345                 350

Val Thr Gly Ser Arg Met Thr Phe Val Thr Gly Cys Lys Asp Ser Lys
            355                 360                 365

Thr Thr Ser Ile Leu Leu Arg Gly Gly Thr Glu His Val Val Asp Gly
        370                 375                 380

Leu Glu Arg Ala Leu Glu Asp Ala Leu Arg Val Val Gly Val Ala Leu
385                 390                 395                 400

Glu Asp Gln Lys Ile Val Val Gly Gly Gly Ser Pro Glu Ile Glu Leu
                405                 410                 415

Ser Leu Arg Leu Lys Glu Tyr Ala Ala Thr Leu Lys Gly Arg Glu Gln
                420                 425                 430

Leu Ala Val Thr Lys Phe Ala Glu Ser Leu Glu Val Ile Pro Gln Thr
            435                 440                 445

Leu Ala Glu Asn Ala Gly Leu Asp Pro Ile Asp Met Leu Val Glu Met
        450                 455                 460

Arg Ser Gln His Glu Lys Gly Asn Lys Arg Ala Gly Leu Asn Val Tyr
465                 470                 475                 480

Lys Gly Lys Ile Glu Asp Met Phe Glu Asn Asn Val Val Glu Pro Leu
                485                 490                 495

Arg Ile Lys Thr Gln Ala Ile Asn Ala Ala Thr Glu Ala Ala Ile Met
                500                 505                 510

```
Val Leu Arg Ile Asp Asp Val Ile Ala Ser Thr Gly Gly Arg Ala
        515                 520                 525

Ala Pro Gly Gly Met Pro Gly Asp Met Glu Asp Met Met
    530                 535                 540

<210> SEQ ID NO 9
<211> LENGTH: 577
<212> TYPE: PRT
<213> ORGANISM: Arabodopsis thaliana
<220> FEATURE:
<221> NAME/KEY: MISC_FEATURE
<223> OTHER INFORMATION: Mitochondrial thaliana HSP60

<400> SEQUENCE: 9

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr Met Gly Pro Lys
    50                  55                  60

Gly Arg Asn Val Val Ile Glu Gln Ser Trp Gly Ala Pro Lys Val Thr
65                  70                  75                  80

Lys Asp Gly Val Thr Val Ala Lys Ser Ile Glu Phe Lys Asp Lys Ile
                85                  90                  95

Lys Asn Val Gly Ala Ser Leu Val Lys Gln Val Ala Asn Ala Thr Asn
            100                 105                 110

Asp Val Ala Gly Asp Gly Thr Thr Cys Ala Thr Val Leu Thr Arg Ala
        115                 120                 125

Ile Phe Ala Glu Gly Cys Lys Ser Val Ala Ala Gly Met Asn Ala Met
    130                 135                 140

Asp Leu Arg Arg Gly Ile Ser Met Ala Val Asp Ala Val Val Thr Asn
145                 150                 155                 160

Leu Lys Ser Lys Ala Arg Met Ile Ser Thr Ser Glu Glu Ile Ala Gln
                165                 170                 175

Val Gly Thr Ile Ser Ala Asn Gly Glu Arg Glu Ile Gly Glu Leu Ile
            180                 185                 190

Ala Lys Ala Met Glu Lys Val Gly Lys Glu Gly Val Ile Thr Ile Gln
        195                 200                 205

Asp Gly Lys Thr Leu Phe Asn Glu Leu Glu Val Val Glu Gly Met Lys
    210                 215                 220

Leu Asp Arg Gly Tyr Thr Ser Pro Tyr Phe Ile Thr Asn Gln Lys Thr
225                 230                 235                 240

Gln Lys Cys Glu Leu Asp Asp Pro Leu Ile Leu Ile His Glu Lys Lys
                245                 250                 255

Ile Ser Ser Ile Asn Ser Ile Val Lys Val Leu Glu Leu Ala Leu Lys
            260                 265                 270

Arg Gln Arg Pro Leu Leu Ile Val Ser Glu Asp Val Glu Ser Asp Ala
        275                 280                 285

Leu Ala Thr Leu Ile Leu Asn Lys Leu Arg Ala Gly Ile Lys Val Cys
    290                 295                 300

Ala Ile Lys Ala Pro Gly Phe Gly Glu Asn Arg Lys Ala Asn Leu Gln
305                 310                 315                 320

Asp Leu Ala Ala Leu Thr Gly Gly Glu Val Ile Thr Asp Glu Leu Gly
                325                 330                 335
```

-continued

```
Met Asn Leu Glu Lys Val Asp Leu Ser Met Leu Gly Thr Cys Lys Lys
            340                 345                 350

Val Thr Val Ser Lys Asp Asp Thr Val Ile Leu Asp Gly Ala Gly Asp
            355                 360                 365

Lys Lys Gly Ile Glu Glu Arg Cys Glu Gln Ile Arg Ser Ala Ile Glu
            370                 375                 380

Leu Ser Thr Ser Asp Tyr Asp Lys Glu Lys Leu Gln Glu Arg Leu Ala
385                 390                 395                 400

Lys Leu Ser Gly Gly Val Ala Val Leu Lys Ile Gly Gly Ala Ser Glu
                405                 410                 415

Ala Glu Val Gly Glu Lys Lys Asp Arg Val Thr Asp Ala Leu Asn Ala
            420                 425                 430

Thr Lys Ala Ala Val Glu Glu Gly Ile Leu Pro Gly Gly Gly Val Ala
            435                 440                 445

Leu Leu Tyr Ala Ala Arg Glu Leu Glu Lys Leu Pro Thr Ala Asn Phe
        450                 455                 460

Asp Gln Lys Ile Gly Val Gln Ile Ile Gln Asn Ala Leu Lys Thr Pro
465                 470                 475                 480

Val Tyr Thr Ile Ala Ser Asn Ala Gly Val Glu Gly Ala Val Ile Val
                485                 490                 495

Gly Lys Leu Leu Glu Gln Asp Asn Pro Asp Leu Gly Tyr Asp Ala Ala
            500                 505                 510

Lys Gly Glu Tyr Val Asp Met Val Lys Ala Gly Ile Ile Asp Pro Leu
            515                 520                 525

Lys Val Ile Arg Thr Ala Leu Val Asp Ala Ala Ser Val Ser Ser Leu
            530                 535                 540

Leu Thr Thr Thr Glu Ala Val Val Val Asp Leu Pro Lys Asp Glu Ser
545                 550                 555                 560

Glu Ser Gly Ala Ala Gly Ala Gly Met Gly Gly Met Gly Gly Met Asp
                565                 570                 575

Tyr
```

```
<210> SEQ ID NO 10
<211> LENGTH: 559
<212> TYPE: PRT
<213> ORGANISM: Saccharomyces sp
<220> FEATURE:
<221> NAME/KEY: MISC_FEATURE
<223> OTHER INFORMATION: TCP1 alpha subunit

<400> SEQUENCE: 10
```

```
Met Ser Gln Leu Phe Asn Asn Ser Arg Ser Asp Thr Leu Phe Leu Gly
1               5                   10                  15

Gly Glu Lys Ile Ser Gly Asp Asp Ile Arg Asn Gln Asn Val Leu Ala
            20                  25                  30

Thr Met Ala Val Ala Asn Val Val Lys Ser Ser Leu Gly Pro Val Gly
            35                  40                  45

Leu Asp Lys Met Leu Val Asp Asp Ile Gly Asp Phe Thr Val Thr Asn
        50                  55                  60

Asp Gly Ala Thr Ile Leu Ser Leu Leu Asp Val Gln His Pro Ala Gly
65              70                  75                  80

Lys Ile Leu Val Glu Leu Ala Gln Gln Gln Asp Arg Glu Ile Gly Asp
                85                  90                  95

Gly Thr Thr Ser Val Val Ile Ile Ala Ser Glu Leu Leu Lys Arg Ala
            100                 105                 110
```

-continued

Asn Glu Leu Val Lys Asn Lys Ile His Pro Thr Thr Ile Ile Thr Gly
            115                 120                 125

Phe Arg Val Ala Leu Arg Glu Ala Ile Arg Phe Ile Asn Glu Val Leu
        130                 135                 140

Ser Thr Ser Val Asp Thr Leu Gly Lys Glu Thr Leu Ile Asn Ile Ala
145                 150                 155                 160

Lys Thr Ser Met Ser Ser Lys Ile Ile Gly Ala Asp Ser Asp Phe Phe
                165                 170                 175

Ser Asn Met Val Val Asp Ala Leu Leu Ala Val Lys Thr Gln Asn Ser
            180                 185                 190

Lys Gly Glu Ile Lys Tyr Pro Val Lys Ala Val Asn Val Leu Lys Ala
        195                 200                 205

His Gly Lys Ser Ala Thr Glu Ser Leu Leu Val Pro Gly Tyr Ala Leu
    210                 215                 220

Asn Cys Thr Val Ala Ser Gln Ala Met Pro Lys Arg Ile Ala Gly Gly
225                 230                 235                 240

Asn Val Lys Ile Ala Cys Leu Asp Leu Asn Leu Gln Lys Ala Arg Met
                245                 250                 255

Ala Met Gly Val Gln Ile Asn Ile Asp Asp Pro Gln Leu Glu Gln
            260                 265                 270

Ile Arg Lys Arg Glu Ala Gly Ile Val Leu Glu Arg Val Lys Lys Ile
        275                 280                 285

Ile Asp Ala Gly Ala Gln Val Val Leu Thr Thr Lys Gly Ile Asp Asp
    290                 295                 300

Leu Cys Leu Lys Glu Phe Val Glu Ala Lys Ile Met Gly Val Arg Arg
305                 310                 315                 320

Cys Lys Lys Glu Asp Leu Arg Arg Ile Ala Arg Ala Thr Gly Ala Thr
                325                 330                 335

Leu Val Ser Ser Met Ser Asn Leu Glu Gly Glu Glu Thr Phe Glu Ser
            340                 345                 350

Ser Tyr Leu Gly Leu Cys Asp Glu Val Val Gln Ala Lys Phe Ser Asp
        355                 360                 365

Asp Glu Cys Ile Leu Ile Lys Gly Thr Ser Lys His Ser Ser Ser Ser
    370                 375                 380

Ile Ile Leu Arg Gly Ala Asn Asp Tyr Ser Leu Asp Glu Met Glu Arg
385                 390                 395                 400

Ser Leu His Asp Ser Leu Ser Val Val Lys Arg Thr Leu Glu Ser Gly
                405                 410                 415

Asn Val Val Pro Gly Gly Gly Cys Val Glu Ala Ala Leu Asn Ile Tyr
            420                 425                 430

Leu Asp Asn Phe Ala Thr Thr Val Gly Ser Arg Glu Gln Leu Ala Ile
        435                 440                 445

Ala Glu Phe Ala Ala Ala Leu Leu Ile Ile Pro Lys Thr Leu Ala Val
    450                 455                 460

Asn Ala Ala Lys Asp Ser Ser Glu Leu Val Ala Lys Leu Arg Ser Tyr
465                 470                 475                 480

His Ala Ala Ser Gln Met Ala Lys Pro Glu Asp Val Lys Arg Arg Ser
                485                 490                 495

Tyr Arg Asn Tyr Gly Leu Asp Leu Ile Arg Gly Lys Ile Val Asp Glu
            500                 505                 510

Ile His Ala Gly Val Leu Glu Pro Thr Ile Ser Lys Val Lys Ser Leu
        515                 520                 525

```
Lys Ser Ala Leu Glu Ala Cys Val Ala Ile Leu Arg Ile Asp Thr Met
    530                 535                 540

Ile Thr Val Asp Pro Glu Pro Pro Lys Glu Asp Pro His Asp His
545                 550                 555
```

<210> SEQ ID NO 11
<211> LENGTH: 485
<212> TYPE: PRT
<213> ORGANISM: Homo sapien
<220> FEATURE:
<221> NAME/KEY: MISC_FEATURE
<223> OTHER INFORMATION: Human mitochondrial HSP60

<400> SEQUENCE: 11

```
Met Pro Ser Lys Lys Met Pro Gly Lys Ser Asn His Gly Lys Asn Asn
1               5                   10                  15

Thr Phe Lys Leu Arg Ala Lys Phe Ser Phe Pro Ile Leu Ala Ala Asp
                20                  25                  30

Val Pro Ser Ala Phe Leu Tyr Gly Thr Ser His Ser Gly Gln Leu Ser
            35                  40                  45

Leu Pro Gly Ala Lys Arg Ser Tyr Gly Gln Leu Pro Pro Ser Leu Ala
        50                  55                  60

Leu Gln Asp Lys Tyr Lys Asn Thr Gly Ala Lys Leu Val Gln Asp Val
65                  70                  75                  80

Ala Asn Asn Thr Asn Glu Glu Ala Val Asp Gly Thr Thr Thr Val Thr
                85                  90                  95

Ala Leu Ala Arg Ser Ile Ala Lys Glu Gly Phe Glu Lys Ile Ser Lys
            100                 105                 110

Gly Ala Asn Pro Val Glu Ile Arg Arg Gly Val Met Leu Ala Val Asp
        115                 120                 125

Ala Ile Ile Ala Glu Pro Lys Lys Gln Ser Lys Pro Val Thr Thr Pro
130                 135                 140

Glu Glu Ile Ala Arg Val Ala Thr Ile Ser Ala Asn Gly Asp Lys Glu
145                 150                 155                 160

Ile Gly Asn Ile Ile Ser Asp Ala Met Lys Lys Val Gly Ser Lys Gly
                165                 170                 175

Ile Ile Thr Val Asn Asn Gly Lys Ser Gln Lys Cys Glu Phe Gln Asp
            180                 185                 190

Ala Tyr Val Leu Leu Ser Glu Lys Lys Ile Ser Ser Val Gln Ser Ile
        195                 200                 205

Ala Pro Ala Leu Glu Ile Ala Asn Ala Tyr Ser Leu Val Ile Ile Ala
210                 215                 220

Glu Asp Val Asn Gly Glu Ala Leu Ser Thr Leu Val Leu Asn Arg Leu
225                 230                 235                 240

Lys Val Gly Leu Gln Val Val Ala Val Lys Asp Pro Gly Phe Gly Asp
                245                 250                 255

Asn Arg Asn Asn Gln Leu Lys Asp Met Ala Ile Ala Thr Gly Gly Ala
            260                 265                 270

Val Phe Ala Glu Glu Gly Leu Thr Leu Asn Leu Glu Asp Val Gln Pro
        275                 280                 285

His Asp Leu Gly Lys Val Gly Glu Val Ile Val Thr Lys Asp Asp Ala
290                 295                 300

Met Leu Leu Lys Gly Lys Asp Gly Val Ala Val Leu Lys Val Gly Gly
305                 310                 315                 320

Thr Ser Asp Ala Glu Val Asn Glu Lys Gln Asp Arg Val Thr Asp Ala
                325                 330                 335
```

```
Leu Asn Ala Thr Arg Ala Ala Val Glu Glu Gly Ile Val Leu Arg Gly
            340                 345                 350

Gly Arg Ala Leu Leu Arg Cys Ile Pro Ala Leu Asp Ser Leu Thr Pro
            355                 360                 365

Val Asn Glu Asp His Asn Ile Gly Ile Glu Ile Ile Lys Lys Thr Leu
            370                 375                 380

Lys Phe Pro Ala Met Thr Ile Ala Lys Asn Ala Gly Val Glu Val Ser
385                 390                 395                 400

Leu Ile Val Glu Lys Ile Met Gln Ser Ser Glu Val Gly Tyr Asp
            405                 410                 415

Ala Met Gly Arg Asp Phe Val Asn Met Val Glu Lys Gly Ile Ile Asp
            420                 425                 430

Thr Thr Lys Phe Val Arg Thr Ala Leu Leu Asp Ala Ser Gly Val Ala
            435                 440                 445

Ser Leu Leu Thr Thr Ala Glu Val Leu Val Thr Glu Ile Pro Lys Glu
            450                 455                 460

Glu Lys Asp Pro Gly Met Gly Ala Met Asp Gly Met Gly Gly Met
465                 470                 475                 480

Gly Gly Gly Met Phe
            485

<210> SEQ ID NO 12
<211> LENGTH: 573
<212> TYPE: PRT
<213> ORGANISM: Mus sp
<220> FEATURE:
<221> NAME/KEY: MISC_FEATURE
<223> OTHER INFORMATION: Mouse mitochondrial HSP60

<400> SEQUENCE: 12

Met Leu Arg Leu Pro Thr Val Leu Arg Gln Met Arg Pro Val Ser Arg
1               5                   10                  15

Ala Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
            50                  55                  60

Glu Gln Ser Trp Gly Ser Pro Lys Val Thr Lys Asp Gly Val Thr Val
65              70                  75                  80

Ala Lys Ser Ile Asp Leu Lys Asp Lys Tyr Lys Asn Ile Gly Ala Lys
            85                  90                  95

Leu Val Gln Asp Val Ala Asn Asn Thr Asn Glu Glu Ala Gly Asp Gly
            100                 105                 110

Thr Thr Thr Ser Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
            130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
            165                 170                 175

Asn Gly Asp Lys Asp Ile Gly Asn Ile Ile Ser Asp Ala Met Lys Lys
            180                 185                 190

Val Gly Arg Lys Gly Val Ile Thr Val Lys Asp Gly Lys Thr Leu Asn
```

-continued

```
              195                 200                 205
Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Val Gln Ser
                245                 250                 255

Ile Val Pro Thr Leu Glu Ile Ala Asn Ala His Arg Lys Pro Leu Val
            260                 265                 270

Ile Ile Ala Glu Asp Val Asp Gly Glu Ala Leu Ser Thr Met Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Asn Leu Asn Leu Glu Asp
                325                 330                 335

Val Gln Ala His Asp Leu Gly Lys Val Gly Glu Val Ile Val Thr Lys
            340                 345                 350

Asp Asp Ala Met Leu Leu Lys Gly Lys Gly Asp Lys Ala His Ile Glu
        355                 360                 365

Lys Arg Ile Gln Glu Ile Thr Glu Gln Leu Asp Ile Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
        435                 440                 445

Pro Ala Leu Asp Ser Leu Lys Pro Ala Asn Glu Asp Gln Lys Ile Gly
    450                 455                 460

Ile Glu Ile Ile Lys Arg Ala Leu Lys Ile Pro Ala Met Thr Ile Ala
465                 470                 475                 480

Lys Asn Ala Gly Val Glu Gly Ser Leu Ile Val Glu Lys Ile Leu Gln
                485                 490                 495

Ser Ser Ser Glu Val Gly Tyr Asp Ala Arg Leu Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Ala
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Ser Met Leu
                565                 570

<210> SEQ ID NO 13
<211> LENGTH: 556
<212> TYPE: PRT
<213> ORGANISM: Homo sapien
<220> FEATURE:
<221> NAME/KEY: MISC_FEATURE
<223> OTHER INFORMATION: Human TCP1
```

<400> SEQUENCE: 13

```
Met Glu Gly Pro Leu Ser Val Phe Gly Asp Arg Ser Thr Gly Glu Thr
1               5                   10                  15

Ile Arg Ser Gln Asn Val Met Ala Ala Ser Ile Ala Asn Ile Val
            20                  25                  30

Lys Ser Ser Leu Gly Pro Val Gly Leu Asp Lys Met Leu Val Asp Asp
        35                  40                  45

Ile Gly Asp Val Thr Ile Thr Asn Asp Gly Ala Thr Ile Leu Lys Leu
50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Val Asn Thr Asp Glu Leu Gly
    130                 135                 140

Arg Asp Cys Leu Ile Asn Ala Ala Lys Thr Ser Met Ser Ser Lys Ile
145                 150                 155                 160

Ile Gly Ile Asn Gly Asp Phe Phe Ala Asn Met Val Val Asp Ala Val
                165                 170                 175

Leu Ala Ile Lys Tyr Thr Asp Ile Arg Gly Gln Pro Arg Tyr Pro Val
            180                 185                 190

Asn Ser Val Asn Ile Leu Lys Ala His Gly Arg Ser Gln Met Glu Ser
        195                 200                 205

Met Leu Ile Ser Gly Tyr Ala Leu Asn Cys Val Val Gly Ser Gln Gly
    210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Val Ile Thr Asp
                245                 250                 255

Pro Glu Lys Leu Asp Gln Ile Arg Gln Arg Glu Ser Asp Ile Thr Lys
            260                 265                 270

Glu Arg Ile Gln Lys Ile Leu Ala Thr Gly Ala Asn Val Ile Leu Thr
        275                 280                 285

Thr Gly Gly Ile Asp Asp Met Cys Leu Lys Tyr Phe Val Glu Ala Gly
    290                 295                 300

Ala Met Ala Val Arg Arg Val Leu Lys Arg Asp Leu Lys Arg Ile Ala
305                 310                 315                 320

Lys Ala Ser Gly Ala Thr Ile Leu Ser Thr Leu Ala Asn Leu Glu Gly
                325                 330                 335

Glu Glu Thr Phe Glu Ala Ala Met Leu Gly Gln Ala Glu Glu Val Val
            340                 345                 350

Gln Glu Arg Ile Cys Asp Asp Glu Leu Ile Leu Ile Lys Asn Thr Lys
        355                 360                 365

Ala Arg Thr Ser Ala Ser Ile Ile Leu Arg Gly Ala Asn Asp Phe Met
    370                 375                 380

Cys Asp Glu Met Glu Arg Ser Leu His Asp Ala Leu Cys Val Val Lys
385                 390                 395                 400

Arg Val Leu Glu Ser Lys Ser Val Val Pro Gly Gly Gly Ala Val Glu
```

-continued

```
                      405                 410                 415
Ala Ala Leu Ser Ile Tyr Leu Glu Asn Tyr Ala Thr Ser Met Gly Ser
            420                 425                 430

Arg Glu Gln Leu Ala Ile Ala Glu Phe Ala Arg Ser Leu Leu Val Ile
        435                 440                 445

Pro Asn Thr Leu Ala Val Asn Ala Ala Gln Asp Ser Thr Asp Leu Val
    450                 455                 460

Ala Lys Leu Arg Ala Phe His Asn Glu Ala Gln Val Asn Pro Glu Arg
465                 470                 475                 480

Lys Asn Leu Lys Trp Ile Gly Leu Asp Leu Ser Asn Gly Lys Pro Arg
                485                 490                 495

Asp Asn Lys Gln Ala Gly Val Phe Glu Pro Thr Ile Val Lys Val Lys
            500                 505                 510

Ser Leu Lys Phe Ala Thr Glu Ala Ala Ile Thr Ile Leu Arg Ile Asp
        515                 520                 525

Asp Leu Ile Lys Leu His Pro Glu Ser Lys Asp Asp Lys His Gly Ser
    530                 535                 540

Tyr Glu Asp Ala Val His Ser Gly Ala Leu Asn Asp
545                 550                 555

<210> SEQ ID NO 14
<211> LENGTH: 556
<212> TYPE: PRT
<213> ORGANISM: Mus sp
<220> FEATURE:
<221> NAME/KEY: MISC_FEATURE
<223> OTHER INFORMATION: Mouse TCP1

<400> SEQUENCE: 14

Met Glu Gly Pro Leu Ser Val Phe Gly Asp Arg Ser Thr Gly Glu Ala
1               5                   10                  15

Val Arg Ser Gln Asn Val Met Ala Ala Ala Ser Ile Ala Asn Ile Val
            20                  25                  30

Lys Ser Ser Phe Gly Pro Val Gly Leu Asp Lys Met Leu Val Asp Asp
        35                  40                  45

Ile Gly Asp Val Thr Ile Thr Asn Asp Gly Ala Thr Ile Leu Lys Leu
    50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Ile Asn Thr Asp Glu Leu Gly
    130                 135                 140

Arg Asp Cys Leu Ile Asn Ala Ala Lys Thr Ser Met Ser Ser Lys Ile
145                 150                 155                 160

Ile Gly Ile Asn Gly Asp Tyr Phe Ala Asn Met Val Val Asp Ala Val
                165                 170                 175

Leu Ala Val Lys Tyr Thr Asp Ala Arg Gly Gln Pro Arg Tyr Pro Val
            180                 185                 190

Asn Ser Val Asn Ile Leu Lys Ala His Gly Arg Ser Gln Ile Glu Ser
        195                 200                 205
```

```
Met Leu Ile Asn Gly Tyr Ala Leu Asn Cys Val Val Gly Ser Gln Gly
210                 215                 220
Met Pro Lys Arg Ile Val Asn Ala Lys Ile Ala Cys Leu Asp Phe Ser
225                 230                 235                 240
Leu Gln Lys Thr Lys Met Lys Leu Gly Val Gln Val Val Ile Thr Asp
                245                 250                 255
Pro Glu Lys Leu Asp Gln Ile Arg Gln Arg Glu Ser Asp Ile Thr Lys
            260                 265                 270
Glu Arg Ile Gln Lys Ile Leu Ala Thr Gly Ala Asn Val Ile Leu Thr
        275                 280                 285
Thr Gly Gly Ile Asp Asp Met Tyr Leu Lys Tyr Phe Val Glu Ala Gly
290                 295                 300
Ala Met Ala Val Arg Arg Val Leu Lys Arg Asp Leu Lys His Val Ala
305                 310                 315                 320
Lys Ala Ser Gly Ala Ser Ile Leu Ser Thr Leu Ala Asn Leu Glu Gly
                325                 330                 335
Glu Glu Thr Phe Glu Val Thr Met Leu Gly Gln Ala Glu Glu Val Val
            340                 345                 350
Gln Glu Arg Ile Cys Asp Glu Leu Ile Leu Ile Lys Asn Thr Lys
        355                 360                 365
Ala Arg Thr Ser Ala Ser Ile Ile Leu Arg Gly Ala Asn Asp Phe Met
370                 375                 380
Cys Asp Glu Met Glu Arg Ser Leu His Asp Ala Leu Cys Val Val Lys
385                 390                 395                 400
Arg Val Leu Glu Leu Lys Ser Val Val Pro Gly Gly Gly Ala Val Glu
                405                 410                 415
Ala Ala Leu Ser Ile Tyr Leu Glu Asn Tyr Ala Thr Ser Met Gly Ser
            420                 425                 430
Arg Glu Gln Leu Ala Ile Ala Glu Phe Ala Arg Ser Leu Leu Val Ile
        435                 440                 445
Pro Asn Thr Leu Ala Val Asn Ala Ala Gln Asp Ser Thr Asp Leu Val
450                 455                 460
Ala Lys Leu Arg Ala Phe His Asn Glu Ala Gln Val Asn Pro Glu Arg
465                 470                 475                 480
Lys Asn Leu Lys Trp Ile Gly Leu Asp Leu Val His Gly Lys Pro Arg
                485                 490                 495
Asp Asn Lys Gln Ala Gly Val Phe Glu Pro Thr Ile Val Lys Val Lys
            500                 505                 510
Ser Leu Lys Phe Ala Thr Glu Ala Ala Ile Thr Ile Leu Arg Ile Asp
        515                 520                 525
Asp Leu Ile Lys Leu His Pro Glu Ser Lys Asp Lys His Gly Ser
530                 535                 540
Tyr Glu Asn Ala Val His Ser Gly Ala Leu Asp Asp
545                 550                 555

<210> SEQ ID NO 15
<211> LENGTH: 606
<212> TYPE: PRT
<213> ORGANISM: Artificial
<220> FEATURE:
<223> OTHER INFORMATION: alignment consensus sequence

<400> SEQUENCE: 15

Glx Glx Glx Glx Glx Glx Glx Glx Glx Glx Glx Glx Glx Glx Glx Glx
1               5                   10                  15
```

```
Glx Glx Glx Glx Glx Glx Glx Glx Glx Pro Ile Glx Ile Glx Glu
            20                  25                  30

Ala Glx Glx Arg Glx Phe Gly Glx Asp Ala Arg Glx Glx Asn Ile Glx
        35                  40                  45

Ala Ala Glx Ala Leu Ala Glu Ala Val Lys Ser Thr Leu Gly Pro Lys
    50                  55                  60

Gly Leu Asp Lys Met Leu Val Asp Ser Trp Gly Asp Ile Thr Ile Thr
65                  70                  75                  80

Asn Asp Gly Glx Thr Ile Leu Lys Glu Ile Glu Leu Glu His Pro Glx
                85                  90                  95

Glx Glx Glx Gly Ala Lys Leu Leu Glx Glu Val Ala Glx Glx Gln Asp
            100                 105                 110

Asp Glu Glx Gly Asp Gly Thr Thr Thr Ala Val Val Leu Ala Glx Ala
            115                 120                 125

Leu Leu Lys Glx Ala Glx Glu Leu Val Glx Glx Gly Ile His Pro Thr
        130                 135                 140

Glx Glx Ile Glx Gly Tyr Glx Leu Ala Val Glu Glx Ala Val Arg Glx
145                 150                 155                 160

Ile Glx Glx Glx Ala Glx Glx Glx Glx Val Glx Glx Glx Glu Glx
                165                 170                 175

Ile Glx Gln Val Ala Glx Thr Ser Ala Glx Ser Lys Glx Glx Glx Gly
            180                 185                 190

Glx Glx Glx Ala Asp Ala Met Glx Glx Val Gly Val Glu Ala Val Ile
        195                 200                 205

Thr Val Glx Glu Glx Lys Glx Gly Glx Glx Glx Glx Glx Glx Val Glu
    210                 215                 220

Glx Val Lys Ile Asp Lys Gly Tyr Gly Glx Ser Glx Glx Asp Ser Glx
225                 230                 235                 240

Leu Ile Glx Gly Glx Glx Glx Glx Val Glx Glu Glx Glx Gly Met
            245                 250                 255

Pro Lys Lys Ile Glx Glx Glx Ala Lys Ile Glx Leu Leu Asp Glx
        260                 265                 270

Glx Leu Glx Glx Lys Pro Glx Leu Glx Ile Glx Ile Glx Ile Glu
    275                 280                 285

Glx Glx Ala Leu Ser Glx Leu Val Leu Asn Arg Glu Arg Glx Ile Leu
    290                 295                 300

Lys Glu Val Ala Glx Lys Ile Glx Gly Glx Gly Ala Asn Val Val Glx
305                 310                 315                 320

Glx Lys Gly Ile Asp Asp Leu Glx Glx Glx Glx Leu Ile Glx Glx
            325                 330                 335

Glx Glx Glx Glx Leu Ala Leu Arg Arg Val Lys Lys Glx Asp Leu Glx
        340                 345                 350

Lys Leu Ala Lys Ala Thr Gly Ala Lys Ile Val Thr Thr Ile Glx Glu
        355                 360                 365

Leu Glx Gly Glu Glx Glx Glx Glx Glx Glx Glx Glx Glx Leu Gly
    370                 375                 380

Glx Ala Glx Glu Val Glx Glx Lys Glx Glx Glx Asp Lys Leu Glx
385                 390                 395                 400

Glx Ile Glx Ala Glx Lys Ala Glx Gly Val Ala Ser Ile Leu Leu Arg
        405                 410                 415

Gly Ala Thr Glu Glx Glx Val Asp Glu Glx Glu Arg Ser Leu Glx Asp
            420                 425                 430

Ala Leu Glx Val Lys Ala Ala Leu Glu Glx Glu Gly Glx Val Val Gly
```

```
                435                 440                 445
Gly Gly Gly Ala Leu Glu Glx Leu Ala Glx Leu Leu Glx Glx Tyr
            450                 455                 460

Ala Glx Thr Val Glx Gly Arg Glu Gln Leu Ala Ile Glx Glx Phe Ala
465                 470                 475                 480

Glx Ala Leu Glu Glx Ile Pro Glx Thr Leu Ala Glx Asn Ala Gly Leu
                485                 490                 495

Asp Glx Glx Asp Ile Val Glx Lys Leu Arg Ser Glx His Glx Glx Glx
            500                 505                 510

Glx Glx Glx Glx Glx Glx Glx Glx Glx Glx Glx Glx Glx Glx Glx
            515                 520                 525

Gly Leu Asp Leu Glx Glx Glx Glx Gly Glx Asp Met Val Glx Glx
            530                 535                 540

Gly Val Ile Asp Pro Glx Lys Val Lys Arg Glx Ala Leu Glx Glx Ala
545                 550                 555                 560

Thr Glu Ala Ala Glx Leu Ile Leu Arg Ile Asp Asp Val Val Glx Glx
                565                 570                 575

Glx Pro Glx Glx Glx Glx Asp Glx Glx Glx Ala Glx Glx Glx Glx
            580                 585                 590

Glx Glx Glx Met Gly Glx Glx Glx Glx Glx Glx Glx Glx
        595                 600                 605
```

<210> SEQ ID NO 16
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 16

```
Val Thr Ser Pro Asp Ser Thr Thr Gly Ala Met Ala
1               5                   10
```

<210> SEQ ID NO 17
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 17

```
Ala Ala Ser Pro Thr Gln Ser Met Ser Gln Ala Pro
1               5                   10
```

<210> SEQ ID NO 18
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 18

```
Ala Gln Asn Pro Ser Asp Asn Asn Thr His Thr His
1               5                   10
```

<210> SEQ ID NO 19
<211> LENGTH: 12
<212> TYPE: PRT
<213> ORGANISM: Artificial
<220> FEATURE:
<223> OTHER INFORMATION: metal binding peptide - GaAs or InP -continued

```
<400> SEQUENCE: 19

Ala Ser Ser Ser Arg Ser His Phe Gly Gln Thr Asp
1               5                   10

<210> SEQ ID NO 20
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 20

Trp Ala His Ala Pro Gln Leu Ala Ser Ser Ser Thr
1               5                   10

<210> SEQ ID NO 21
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 21

Ala Arg Tyr Asp Leu Ser Ile Pro Ser Ser Glu Ser
1               5                   10

<210> SEQ ID NO 22
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 22

Thr Pro Pro Arg Pro Ile Gln Tyr Asn His Thr Ser
1               5                   10

<210> SEQ ID NO 23
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 23

Ser Ser Leu Gln Leu Pro Glu Asn Ser Phe Pro His
1               5                   10

<210> SEQ ID NO 24
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 24

Gly Thr Leu Ala Asn Gln Gln Ile Phe Leu Ser Ser
1               5                   10

<210> SEQ ID NO 25
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 25
```

```
His Gly Asn Pro Leu Pro Met Thr Pro Phe Pro Gly
1               5                   10

<210> SEQ ID NO 26
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 26

Arg Leu Glu Leu Ala Ile Pro Leu Gln Gly Ser Gly
1               5                   10

<210> SEQ ID NO 27
<211> LENGTH: 9
<212> TYPE: PRT
<213> ORGANISM: Artificial
<220> FEATURE:
<223> OTHER INFORMATION: metal binding peptide - ZnS

<400> SEQUENCE: 27

Cys Asn Asn Pro Met His Gln Asn Cys
1               5

<210> SEQ ID NO 28
<211> LENGTH: 12
<212> TYPE: PRT
<213> ORGANISM: Artificial
<220> FEATURE:
<223> OTHER INFORMATION: metal binding peptide - Ag

<400> SEQUENCE: 28

Ala Tyr Ser Ser Gly Ala Pro Pro Met Pro Pro Phe
1               5                   10

<210> SEQ ID NO 29
<211> LENGTH: 12
<212> TYPE: PRT
<213> ORGANISM: Artificial
<220> FEATURE:
<223> OTHER INFORMATION: metal binding peptide - Ag

<400> SEQUENCE: 29

Asn Pro Ser Ser Leu Phe Arg Tyr Leu Pro Ser Asp
1               5                   10

<210> SEQ ID NO 30
<211> LENGTH: 12
<212> TYPE: PRT
<213> ORGANISM: Artificial
<220> FEATURE:
<223> OTHER INFORMATION: metal binding peptide - Ag

<400> SEQUENCE: 30

Ser Leu Ala Thr Gln Pro Pro Arg Thr Pro Pro Val
1               5                   10

<210> SEQ ID NO 31
<211> LENGTH: 14
<212> TYPE: PRT
<213> ORGANISM: Artificial
<220> FEATURE:
<223> OTHER INFORMATION: metal binding peptide - Au

<400> SEQUENCE: 31
```

```
Met His Gly Lys Thr Gln Ala Thr Ser Gly Thr Ile Gln Ser
1               5                   10
```

<210> SEQ ID NO 32
<211> LENGTH: 14
<212> TYPE: PRT
<213> ORGANISM: Artificial
<220> FEATURE:
<223> OTHER INFORMATION: metal binding peptide - Au

<400> SEQUENCE: 32

```
Ala Leu Val Pro Thr Ala His Arg Leu Asp Gly Asn Met His
1               5                   10
```

<210> SEQ ID NO 33
<211> LENGTH: 21
<212> TYPE: DNA
<213> ORGANISM: Artificial
<220> FEATURE:
<223> OTHER INFORMATION: PCR primer - gamma gene

<400> SEQUENCE: 33
atgaacttag agccttccta t                                              21

<210> SEQ ID NO 34
<211> LENGTH: 21
<212> TYPE: DNA
<213> ORGANISM: Artificial
<220> FEATURE:
<223> OTHER INFORMATION: PCR primer - P2 gamma gene

<400> SEQUENCE: 34
ttaactccat aagaaacttg t                                              21

<210> SEQ ID NO 35
<211> LENGTH: 40
<212> TYPE: DNA
<213> ORGANISM: Artificial
<220> FEATURE:
<223> OTHER INFORMATION: PCR primer - P1 primer

<400> SEQUENCE: 35
gaaagaacat atggcctatt tattaagaga aggaacacag                          40

<210> SEQ ID NO 36
<211> LENGTH: 43
<212> TYPE: DNA
<213> ORGANISM: Artificial
<220> FEATURE:
<223> OTHER INFORMATION: PCR primer - P2 primer

<400> SEQUENCE: 36
taaagtactc gagaaaacct aaataaaata atcatatctt aac                      43

<210> SEQ ID NO 37
<211> LENGTH: 1607
<212> TYPE: DNA
<213> ORGANISM: Sulfolobus shibatae
<220> FEATURE:
<221> NAME/KEY: misc_feature
<223> OTHER INFORMATION: TF55 gamma subunit

<400> SEQUENCE: 37
atggcctatt tattaagaga aggaacacag agatctactg gaaacgaggt aatactaaac    60
aacatagctg tagccaaaat attactggaa atgctaaagt caagcctagg tcctaagggt   120

-continued

```
ttagacaaga tgttagttga ggggcaagac attacaataa ctaatgacgg tgcgacaata    180
gttaaaaaca tggaagtgca gcatcctact gcaaaattac tcattgaaac cgctaaaact    240
gttgataccg aggtaggaga tgggacaact tcagtagtcg ttcttgccgg gttactatta    300
gaaaaagctg aggatttgct gaatcagaag atccatccaa ctgtcataat agaaggttat    360
aggaaggctc taagttcatc attagaattg ttaaaaagta ttgcagataa gattagtcca    420
gaagatagga agatagttca cgatctagta tatactactc tatcgagtaa gttcttctca    480
acagagcata ctctagagaa gataataaat ctagttattg aagcttcatt ggcggtattg    540
gataaaagag atggaaccta tgatctggat attaagaata taagattgt aaaagtcaat    600
ggtggggaat ttgatgatag tgagcttgta aatgggatcg ttgtagataa ggagcccacc    660
aatgagaata tgccgaaaag gcggaaaaac gttaaggtaa tgttagctga cttcccatta    720
aaacttgaaa aaacggaaat tagcatgaag ctgggaataa gtgaccccac tcagataaag    780
ggatacttgg atgaacaaac ggcatatgtt aagcaaatgg tggataagat aaaggctatg    840
ggcgttaaat tgtttattac acaaaaggac attgatgaag tcgcttcata tttaatggga    900
aaaagtggga taatagcgtt aaagaacgta agaggagtg acatagagtt actgagtaga    960
gctactggtg cgaaaattgc aagtagcatg aaagacgcta atgagagtga tttaggggaa   1020
gctaaattag tggaggttag aaatttagga aagaacaaat acctcttcat tcaatctgat   1080
aaagctaaag cggtgactgt aatcataaag ggctcgaata acatggtaac tgatgaagca   1140
gaaaggagtt taaatgacgc ctttaactcc ataagaaact tgttactaga accctatatt   1200
gtggctggtg gtggtgctgt agaggaggag ttggctaaga ggttaaggga aacgctgga    1260
aaagttcccg gaaaggagca attggcattt aatgcatttg cggatgcttt ggaggagtac   1320
gtttcaatac tatcagaaac tgctggcatg gatcccataa gtgcgttaac cgaaataaga   1380
cataaacatg caaacgggtt aaagaatgct gggattgaca tagttaaggc tagaatttac   1440
gataacatgc ttgagcttaa agtaatcgat tctctaaagg ttaaggaaca agttttaaag   1500
agcgccacag aagccgctac tgcgatttta aagatcgacg acatgatagc agcagctcct   1560
gcaaagcaac aacctcaacc acaacagcca atccatact taggtta               1607
```

<210> SEQ ID NO 38
<211> LENGTH: 535
<212> TYPE: PRT
<213> ORGANISM: Sulfolobus shibatae
<220> FEATURE:
<221> NAME/KEY: MISC_FEATURE
<223> OTHER INFORMATION: TF55 gamma subunit

<400> SEQUENCE: 38

```
Met Ala Tyr Leu Leu Arg Glu Gly Thr Gln Arg Ser Thr Gly Asn Glu
1               5                   10                  15

Val Ile Leu Asn Asn Ile Ala Val Ala Lys Ile Leu Leu Glu Met Leu
            20                  25                  30

Lys Ser Ser Leu Gly Pro Lys Gly Leu Asp Lys Met Leu Val Glu Gly
        35                  40                  45

Gln Asp Ile Thr Ile Thr Asn Asp Gly Ala Thr Ile Val Lys Asn Met
    50                  55                  60

Glu Val Gln His Pro Thr Ala Lys Leu Leu Ile Glu Thr Ala Lys Thr
65                  70                  75                  80

Val Asp Thr Glu Val Gly Asp Gly Thr Thr Ser Val Val Val Leu Ala
                85                  90                  95
```

-continued

```
Gly Leu Leu Leu Glu Lys Ala Glu Asp Leu Leu Asn Gln Lys Ile His
            100                 105                 110
Pro Thr Val Ile Ile Glu Gly Tyr Arg Lys Ala Leu Ser Ser Ser Leu
        115                 120                 125
Glu Leu Leu Lys Ser Ile Ala Asp Lys Ile Ser Pro Glu Asp Arg Lys
    130                 135                 140
Ile Val His Asp Leu Val Tyr Thr Thr Leu Ser Ser Lys Phe Phe Ser
145                 150                 155                 160
Thr Glu His Thr Leu Glu Lys Ile Ile Asn Leu Val Ile Glu Ala Ser
                165                 170                 175
Leu Ala Val Leu Asp Lys Arg Asp Gly Thr Tyr Asp Leu Asp Ile Lys
            180                 185                 190
Asn Ile Lys Ile Val Lys Val Asn Gly Gly Glu Phe Asp Asp Ser Glu
        195                 200                 205
Leu Val Asn Gly Ile Val Val Asp Lys Glu Pro Thr Asn Glu Asn Met
    210                 215                 220
Pro Lys Arg Ala Glu Asn Val Lys Val Met Leu Ala Asp Phe Pro Leu
225                 230                 235                 240
Lys Leu Glu Lys Thr Glu Ile Ser Met Lys Leu Gly Ile Ser Asp Pro
                245                 250                 255
Thr Gln Ile Lys Gly Tyr Leu Asp Glu Gln Thr Ala Tyr Val Lys Gln
            260                 265                 270
Met Val Asp Lys Ile Lys Ala Met Gly Val Lys Leu Phe Ile Thr Gln
        275                 280                 285
Lys Asp Ile Asp Glu Val Ala Ser Tyr Leu Met Gly Lys Ser Gly Ile
    290                 295                 300
Ile Ala Leu Lys Asn Val Lys Arg Ser Asp Ile Glu Leu Leu Ser Arg
305                 310                 315                 320
Ala Thr Gly Ala Lys Ile Ala Ser Ser Met Lys Asp Ala Asn Glu Ser
                325                 330                 335
Asp Leu Gly Glu Ala Lys Leu Val Glu Val Arg Asn Leu Gly Lys Asn
            340                 345                 350
Lys Tyr Leu Phe Ile Gln Ser Asp Lys Ala Lys Ala Val Thr Val Ile
        355                 360                 365
Ile Lys Gly Ser Asn Asn Met Val Thr Asp Glu Ala Glu Arg Ser Leu
    370                 375                 380
Asn Asp Ala Phe Asn Ser Ile Arg Asn Leu Leu Glu Pro Tyr Ile
385                 390                 395                 400
Val Ala Gly Gly Gly Ala Val Glu Glu Leu Ala Lys Arg Leu Arg
                405                 410                 415
Glu Asn Ala Gly Lys Val Pro Gly Lys Glu Gln Leu Ala Phe Asn Ala
            420                 425                 430
Phe Ala Asp Ala Leu Glu Glu Tyr Val Ser Ile Leu Ser Glu Thr Ala
        435                 440                 445
Gly Met Asp Pro Ile Ser Ala Leu Thr Glu Ile Arg His Lys His Ala
    450                 455                 460
Asn Gly Leu Lys Asn Ala Gly Ile Asp Ile Lys Ala Arg Ile Tyr
465                 470                 475                 480
Asp Asn Met Leu Glu Leu Lys Val Ile Asp Ser Leu Lys Val Lys Glu
                485                 490                 495
Gln Val Leu Lys Ser Ala Thr Glu Ala Ala Thr Ala Ile Leu Lys Ile
            500                 505                 510
Asp Asp Met Ile Ala Ala Ala Pro Ala Lys Gln Gln Pro Gln Pro Gln
```

```
                515                 520                 525

Gln Pro Asn Pro Tyr Leu Gly
    530                 535

<210> SEQ ID NO 39
<211> LENGTH: 560
<212> TYPE: PRT
<213> ORGANISM: Sulfolobus shibatae
<220> FEATURE:
<221> NAME/KEY: MISC_FEATURE
<223> OTHER INFORMATION: TF55 alpha subunit

<400> SEQUENCE: 39

Met Ala Ser Pro Val Leu Leu Lys Glu Gly Thr Ser Arg Thr Thr
1               5                   10                  15

Gly Arg Asp Ala Leu Arg Asn Asn Ile Leu Ala Ala Lys Thr Leu Ala
                20                  25                  30

Glu Met Leu Arg Ser Ser Leu Gly Pro Lys Gly Leu Asp Lys Met Leu
            35                  40                  45

Ile Asp Ser Phe Gly Asp Val Thr Ile Thr Asn Asp Gly Ala Thr Ile
        50                  55                  60

Val Lys Asp Met Glu Ile Gln His Pro Ala Ala Lys Leu Leu Val Glu
65                  70                  75                  80

Ala Ala Lys Ala Gln Asp Ala Glu Val Gly Asp Gly Thr Thr Ser Ala
                85                  90                  95

Val Val Leu Ala Gly Ala Leu Leu Glu Lys Ala Glu Ser Leu Leu Asp
            100                 105                 110

Gln Asn Ile His Pro Thr Ile Ile Glu Gly Tyr Lys Lys Ala Tyr
        115                 120                 125

Thr Lys Ala Leu Glu Leu Leu Pro Gln Leu Gly Thr Arg Ile Asp Ile
    130                 135                 140

Arg Asp Leu Asn Ser Ser Val Ala Arg Asp Thr Leu Arg Lys Ile Ala
145                 150                 155                 160

Phe Thr Thr Leu Ala Ser Lys Phe Ile Ala Glu Gly Ala Glu Leu Asn
                165                 170                 175

Lys Ile Ile Asp Met Val Ile Asp Ala Ile Asn Val Ala Glu Pro
            180                 185                 190

Leu Pro Asn Gly Gly Tyr Asn Val Ser Leu Asp Leu Ile Lys Ile Asp
        195                 200                 205

Lys Lys Lys Gly Gly Ser Ile Glu Asp Ser Val Leu Val Lys Gly Leu
    210                 215                 220

Val Leu Asp Lys Glu Val Val His Pro Gly Met Pro Arg Arg Val Thr
225                 230                 235                 240

Lys Ala Lys Ile Ala Val Leu Asp Ala Ala Leu Glu Val Glu Lys Pro
                245                 250                 255

Glu Ile Ser Ala Lys Ile Ser Ile Thr Ser Pro Glu Gln Ile Lys Ala
            260                 265                 270

Phe Leu Asp Glu Glu Ser Lys Tyr Leu Lys Asp Met Val Asp Lys Leu
        275                 280                 285

Ala Ser Ile Gly Ala Asn Val Val Ile Cys Gln Lys Gly Ile Asp Asp
    290                 295                 300

Ile Ala Gln His Phe Leu Ala Lys Lys Gly Ile Leu Ala Val Arg Arg
305                 310                 315                 320

Val Lys Arg Ser Asp Ile Glu Lys Leu Glu Lys Ala Leu Gly Ala Arg
                325                 330                 335
```

```
Ile Ile Ser Ser Ile Lys Asp Ala Thr Pro Asp Asp Leu Gly Tyr Ala
                340                 345                 350
Glu Leu Val Glu Glu Arg Arg Val Gly Asn Asp Lys Met Val Phe Ile
            355                 360                 365
Glu Gly Ala Lys Asn Leu Lys Ala Val Asn Ile Leu Leu Arg Gly Ser
        370                 375                 380
Asn Asp Met Ala Leu Asp Glu Ala Glu Arg Ser Ile Asn Asp Ala Leu
385                 390                 395                 400
His Ala Leu Arg Asn Ile Leu Leu Glu Pro Val Ile Leu Pro Gly Gly
                405                 410                 415
Gly Ala Ile Glu Leu Glu Leu Ala Met Lys Leu Arg Glu Tyr Ala Arg
            420                 425                 430
Ser Val Gly Gly Lys Glu Gln Leu Ala Ile Glu Ala Phe Ala Asp Ala
        435                 440                 445
Leu Glu Glu Ile Pro Thr Ile Leu Ala Glu Thr Ala Gly Leu Glu Ala
    450                 455                 460
Ile Ser Ala Leu Met Asp Leu Arg Ala Arg His Ala Lys Gly Leu Thr
465                 470                 475                 480
Asn Thr Gly Val Asp Val Ile Gly Gly Lys Ile Val Asp Asp Val Tyr
                485                 490                 495
Ala Leu Asn Ile Ile Glu Pro Ile Arg Val Lys Ala Gln Val Leu Lys
            500                 505                 510
Ser Ala Thr Glu Ala Ala Thr Ala Ile Leu Lys Ile Asp Asp Leu Ile
        515                 520                 525
Ala Ala Ala Pro Leu Lys Ser Glu Lys Lys Gly Gly Glu Gly Ser Lys
    530                 535                 540
Glu Glu Ser Gly Gly Glu Gly Gly Ala Gly Thr Pro Ser Leu Gly Asp
545                 550                 555                 560

<210> SEQ ID NO 40
<211> LENGTH: 28
<212> TYPE: PRT
<213> ORGANISM: Artificial Sequence
<220> FEATURE:
<223> OTHER INFORMATION: metal binding peptide - Au

<400> SEQUENCE: 40

Pro Gly Met Lys Ala Ser Lys Ser Met Arg Asn Gln Ala Thr Pro Gly
1               5                   10                  15
Met Pro Ser Ser Leu Asp Leu Thr Trp Gln Ala Thr
            20                  25

<210> SEQ ID NO 41
<211> LENGTH: 28
<212> TYPE: PRT
<213> ORGANISM: Artificial Sequence
<220> FEATURE:
<223> OTHER INFORMATION: metal binding peptide - Au

<400> SEQUENCE: 41

Pro Gly Met Lys Met Arg Leu Ser Gly Ala Lys Glu Ala Thr Pro Gly
1               5                   10                  15
Met Ser Thr Thr Val Ala Gly Leu Leu Gln Ala Thr
            20                  25

<210> SEQ ID NO 42
<211> LENGTH: 28
<212> TYPE: PRT
<213> ORGANISM: Artificial Sequence
```

-continued

```
<220> FEATURE:
<223> OTHER INFORMATION: metal binding peptide - Au

<400> SEQUENCE: 42

Pro Gly Met Ile His Val Gln Lys Thr Ala Val Gln Ala Thr Pro Gly
1               5                   10                  15

Met Val Asn Leu Thr Ser Pro Val Lys Gln Ala Thr
            20                  25

<210> SEQ ID NO 43
<211> LENGTH: 14
<212> TYPE: PRT
<213> ORGANISM: Artificial Sequence
<220> FEATURE:
<223> OTHER INFORMATION: metal binding peptide - Au

<400> SEQUENCE: 43

Ala Leu Asp Ser Pro Ala Gly Cys Leu Ser Phe Ser Met His
1               5                   10
```

ORDERED BIOLOGICAL NANOSTRUCTURES FORMED FROM CHAPERONIN POLYPEPTIDES

This application claims benefit of prior U.S. provisional application Ser. No. 60/340,538, titled "Ordered Biological Nanostructures Formed From Extremophillic Heat-Shock Proteins," filed on Nov. 8, 2001, which is hereby incorporated by reference in its entirety, including drawings.

ORIGIN OF THE INVENTION

The invention described herein was made by an employee(s) of the United States Government and may be manufactured and used by or for the Government for governmental purposes without payment of the royalties thereon or therefor.

1. FIELD OF THE INVENTION

The following application relates to nanotemplates, nanostructures, nanoarrays and nanodevices formed from wild-type and mutated chaperonin polypeptides, methods of producing such compositions, methods of using such compositions and particular chaperonin polypeptides that can be utilized in producing such compositions.

2. BACKGROUND OF THE INVENTION

The controlled organization of inorganic materials into multi-dimensional addressable arrays is the foundation for both logic and memory devices, as well as other nonlinear optical and sensing devices (Zhirnov et al., 2001, *Computer* 34, 34-43, Xia et al., 2000, *Adv. Mater.* 12, 693-713). Many of these devices are currently fabricated using lithographic patterning processes that have progressively developed toward greater integration densities and smaller sizes. At submicron scales, however, conventional lithographic processes are approaching their practical and theoretical limits. At scales below 100 nm, ion and electron beam lithography becomes prohibitively expensive and time consuming, and more importantly, at these scales quantum effects fundamentally change the properties of devices (Sato et al., 1997, *J. Appl. Phys.* 82, 696).

Nanoscale templates for constrained synthesis, in situ deposition, or direct patterning of nanometer scale inorganic arrays are being developed using both artificial and natural materials. Artificial materials such as microphase separated block copolymers (Park et al., 2001, *Appl. Phys. Lett.* 79, 257-259) and hexagonally close-packed spheres (Hulteen et al., 1995, *J. Vac. Sci. Technol. A,* 1553-1558) have been used for nanoscale fabrication. Natural materials such as DNA (Richter et al., 2000, *Adv. Mater.* 12, 507-510; Keren et al., 2002, *Science* 297, 72-75), bacterial and archaeal surface layer proteins (S-layer proteins) (Sleytr et al., 1999, *Angew. Chem. Int. Ed.* 38, 1034-1054; Douglas et al., *Appl. Phys. Lett.* 48, 676-678; Hall et al., 2001, *CHEMPHYSCHEM* 3, 184-186), virus capsids (Shenton et al., 1999, *Adv. Mater.* 11, 253-256; Douglas et al., 1999, *Adv. Mater.,* 679-681; Douglas et al., *Nature* 393, 152-155; Wang et al., 2002, *Angew. Chem. Int. Ed.* 41, 459-462), phage (Lee et al., 2002, *Science* 296, 892-895), and some globular proteins (Yamashita, I., 2001, *Thin Solid Films* 393, 12-18) have been used as templates and in other nanoscale applications.

Various nanometer scale objects, including arrays of nanoparticles formed by non-conventional methods are being explored for use as viable alternatives to standard lithographically patterned devices. Individual nanoparticles, also known as quantum dots (QDs), have been shown to behave as isolated device components such as single electron transistors (Likharev, K. K., 1999, *Proc. IEEE* 87, 606-632; Thelander et al., 2001, *Appl. Phys. Lett.* 79, 2106-2108). Theoreticians have postulated that two-dimensional arrays of QDs with nanoscale resolution could form the basis of future generations of electronic and photonic devices. The function of these devices will be based on phenomena such as coulomb charging, inter-dot quantum tunneling and other coherent properties derived from the electronic consequences of confinement and nanoparticle surface area to volume ratios (Maier, S. A. et al., 2001, *Adv. Mater.* 13, 1501-1505; Maier et al., *Phys. Rev. B* 65, 193408; Zrenner, A. et al., 2002, *Nature* 418, 612-614; Berven et al., 2001, *Adv. Mater.* 13, 109-113).

Traditional techniques for patterning ordered arrays of materials onto inorganic substrates and manufacturing devices currently used are ion beam lithography and molecular beam epitaxy. These techniques possess inherent limitations due to the use of polymeric light masks for pattern formation, however, there is a theoretical limitation of patterning that could ultimately limit the processes in the hundreds of nanometers.

While there are strong incentives to develop nanoscale architectures, these developments require alternate fabrication methods and new insights into the behavior of materials on nanometer scales (Nalwa, H. S., 2000, *Handbook of materials and nanotechnology*, Academic Press, San Diego).

3. SUMMARY OF THE INVENTION

The invention provides a method of forming higher order structures comprising at least one mutated chaperonin polypeptide. Such higher order structures include nanotemplates, nanostructures, nanoarrays and nanodevices.

The invention provides a nanotemplate comprising chaperonin polypeptides, wherein at least one polypeptide is a mutated polypeptide. The invention also provides higher order structures comprising at least one mutated chaperonin polypeptide and at least one nanoparticle or quantum dot, including nanostructures, nanoarrays and nanodevices. A nanoarray comprises an ordered array of the nanostructures. A nanodevice comprises at least one nanotemplate, at least one nanostructure, at least one nanoarray or some combination thereof.

The invention also provides a method of forming the nanostructures, nanoarrays and nanodevices. The steps include (a) adding one or more nanounits to a surface, where such nanounits include either nanotemplates or a mixture of nanotemplates and wild-type chaperonins, and (b) adding or synthesizing in situ one or more nanounits comprising (i) at least one nanoparticle, (ii) at least one quantum dot, or (iii) a combination of (i) and (ii) to said surface and (c) if necessary, removing any unbound nanounits. The steps are repeated any number of times in any sequence to form the nanostructures, nanoarrays and nanodevices.

The invention provides variants of chaperonin polypeptide subunits through selective mutation of the chaperonin polypeptide sequence. The mutant chaperonin comprises one more mutated chaperonin polypeptide sequences. The invention provides chaperonin polypeptide variants with one or more point mutations. The invention provides chaperonin polypeptide variants with one or more residues or sequence of residues inserted or deleted. The polypeptide sequences inserted are designed to bind nanoscale materials such as nanoparticles and quantum dots, or to bind only to specific surfaces. The invention also provides for mutations to the N- and C-termini, including deletion of the terminus or insertion of a sequence. In a specific embodiment, the chaperonin polypeptides are HSP60 heat shock proteins.

The invention also provides a method for forming a mutated chaperonin. The steps include modifying at least one protein residue of a chaperonin polypeptide by positioning a mutation to form one or more mutated chaperonin polypeptides, and assembling the one or more mutated chaperonin polypeptides to form a mutated chaperonin.

By genetically engineering a polypeptide that self-assembles into regular double-ring structures known as chaperonins, the present invention teaches methods of directing the organization of nanoparticles, e.g., preformed metal and semiconductor nanoparticles, and quantum dots (QDs), into nanostructures, nanoarrays and nanodevices. The present invention teaches methods of assembling mutated chaperonin polypeptides into structures that function, for example, as nano-vessels, nano-wires, nanotemplates, nano-fabrics, and nanoarrays, e.g., DNA, RNA and/or peptide or polypeptide nanoarrays.

The present invention further provides methods for manufacturing nanodevices, e.g., microelectronics, using chaperonins, in particular, mutant chaperonins comprising at least one mutated chaperonin polypeptide. In one embodiment, the mutant chaperonins comprise at least one mutant extremophillic HSP60 (heat-shock protein).

4. BRIEF DESCRIPTION OF THE DRAWINGS

FIG. 1 illustrates an end and side view of a HSP60 chaperonin at 2.3 Å resolution. The outlined region of the side view shows a single subunit of HSP60.

FIGS. 2A-2R show the protein sequence alignment of *S. shibatae* TF55 beta subunit (SEQ ID NO: 1), bacterial *E. coli* GroEL (SEQ ID NO:2), thermosome *T. acidophilum* beta subunit (SEQ ID NO:3), cyanobacterial synechococcus HSP60 (SEQ ID NO:4), *M. acetivorans* HSP60-4 (SEQ ID NO:5), *M. tuberculosis* HSP65 (SEQ ID NO:6), thermosome *A. pernix* alpha subunit (SEQ ID NO:7), thermosome *M. mazei* alpha subunit (SEQ ID NO:8), mitochondrial *A. thaliana* HSP60 (SEQ ID NO:9), yeast TCP1 alpha subunit (SEQ ID NO:10), human mitochondrial HSP60 (SEQ ID NO:11), mouse mitochondrial HSP60 (SEQ ID NO:12), human TCP1 alpha subunit (SEQ ID NO:13), mouse TCP1 alpha subunit (SEQ ID NO:14), and the consensus (SEQ ID NO:15). Identical residues are enclosed in a dot-dashed box, blocks of similar residues are enclosed in a solid box, and conservative matches are enclosed in a dashed box.

FIGS. 5A-D shows individual HSP60 (heat-shock protein) chaperonins and filaments as observed in the electron microscope.

Figure 6A:
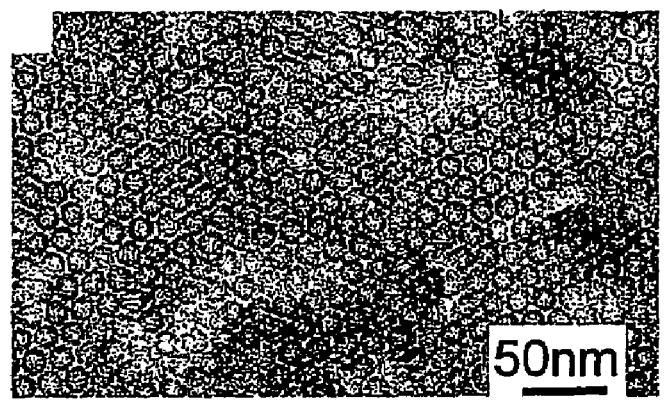
Figure 6B:
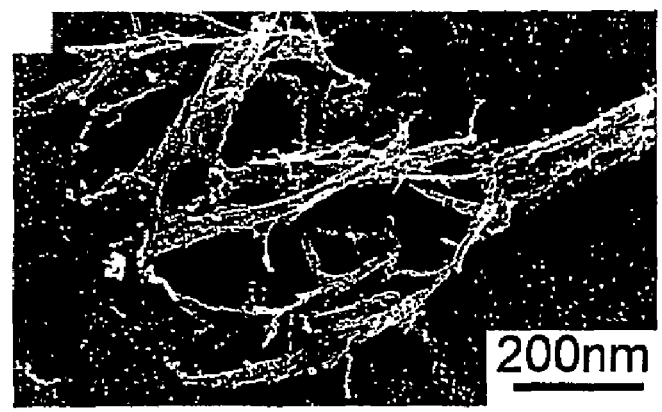

FIGS. 6A and 6B show the organization of HSP60 rings into 2-dimensional crystals on a metal grid coated with lipid (6A) and filament bundles arranged on a bed of rings (visible as spots in background) (6B).

FIGS. 7A-E show the assembly of engineered HSP60s (heat-shock proteins) into nanotemplates for the production of nanoarrays comprising nanoscale materials such as nanoparticle templates.

FIGS. 8A-D show gold nanoparticles binding to engineered chaperonins and chaperonin nanotemplates.

FIGS. 9A-D show semiconductor QD nanoarrays.

Figure 10A:
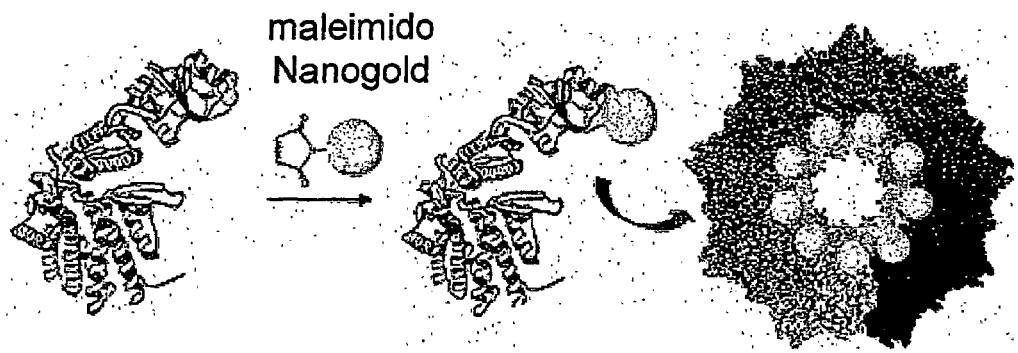
Figure 10B:
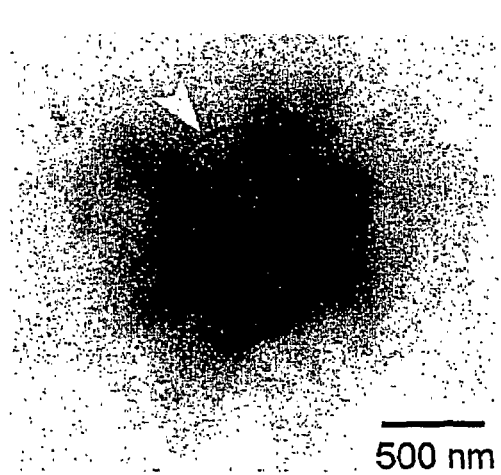
Figure 10C:
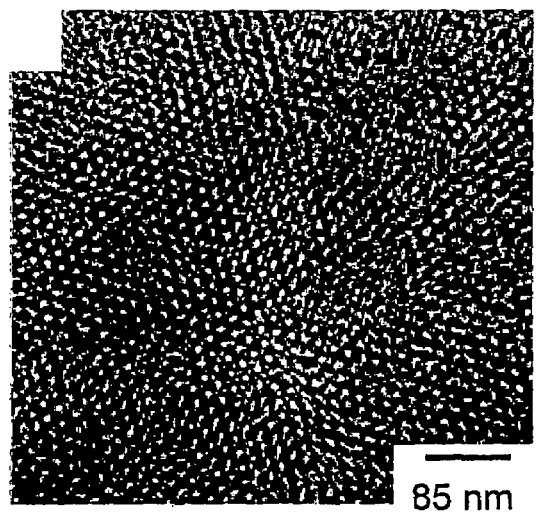
Figure 10D:
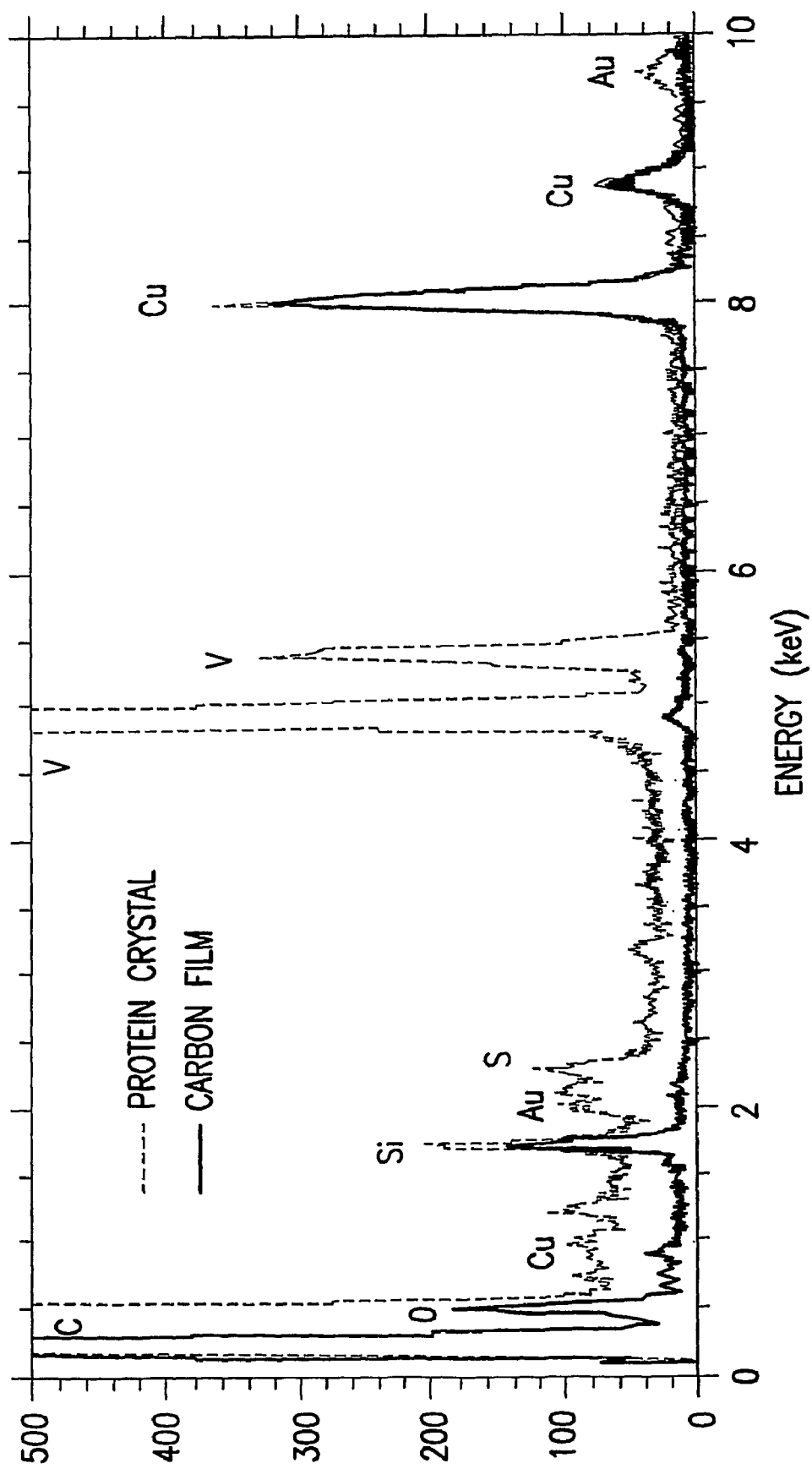

FIGS. 10A-D show the formation of a nanoarray of gold nanoparticles. FIG. 10(D) shows XEDS spectra of bare carbon film (solid line) and the gold nanoparticle nanoarray (dashed line) from the probed area outlined by a circle in FIG. 10(B), as indicated by the arrow.

Figure 11A:
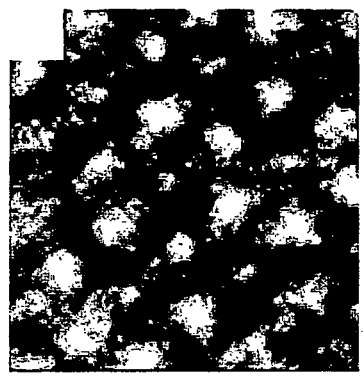
Figure 11B:
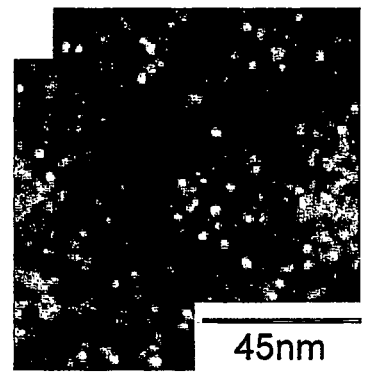
Figure 11C:
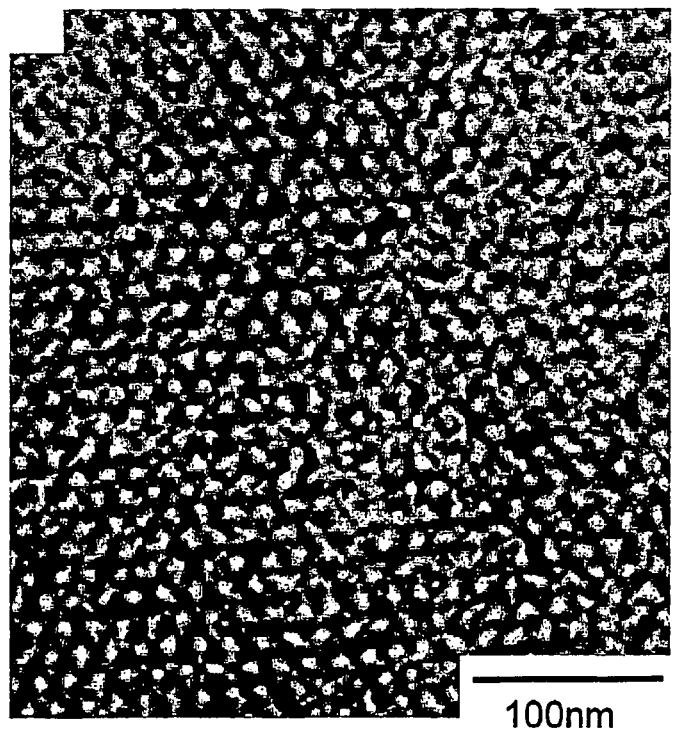

FIGS. 11A-C show HAADF STEM imaging of a nanogold array.

Figure 12:
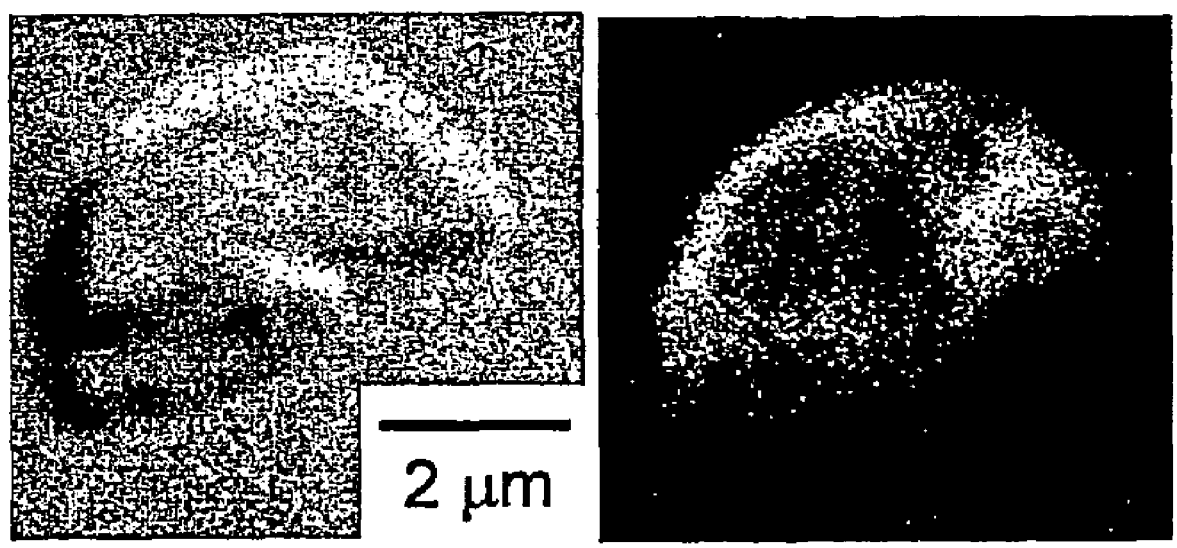

FIG. 12 shows a control experiment showing DIC (left) and fluorescent (right) images of non-cys-mutated chaperonin crystals after incubation with CdSe—ZnS QDs.

Figure 13:
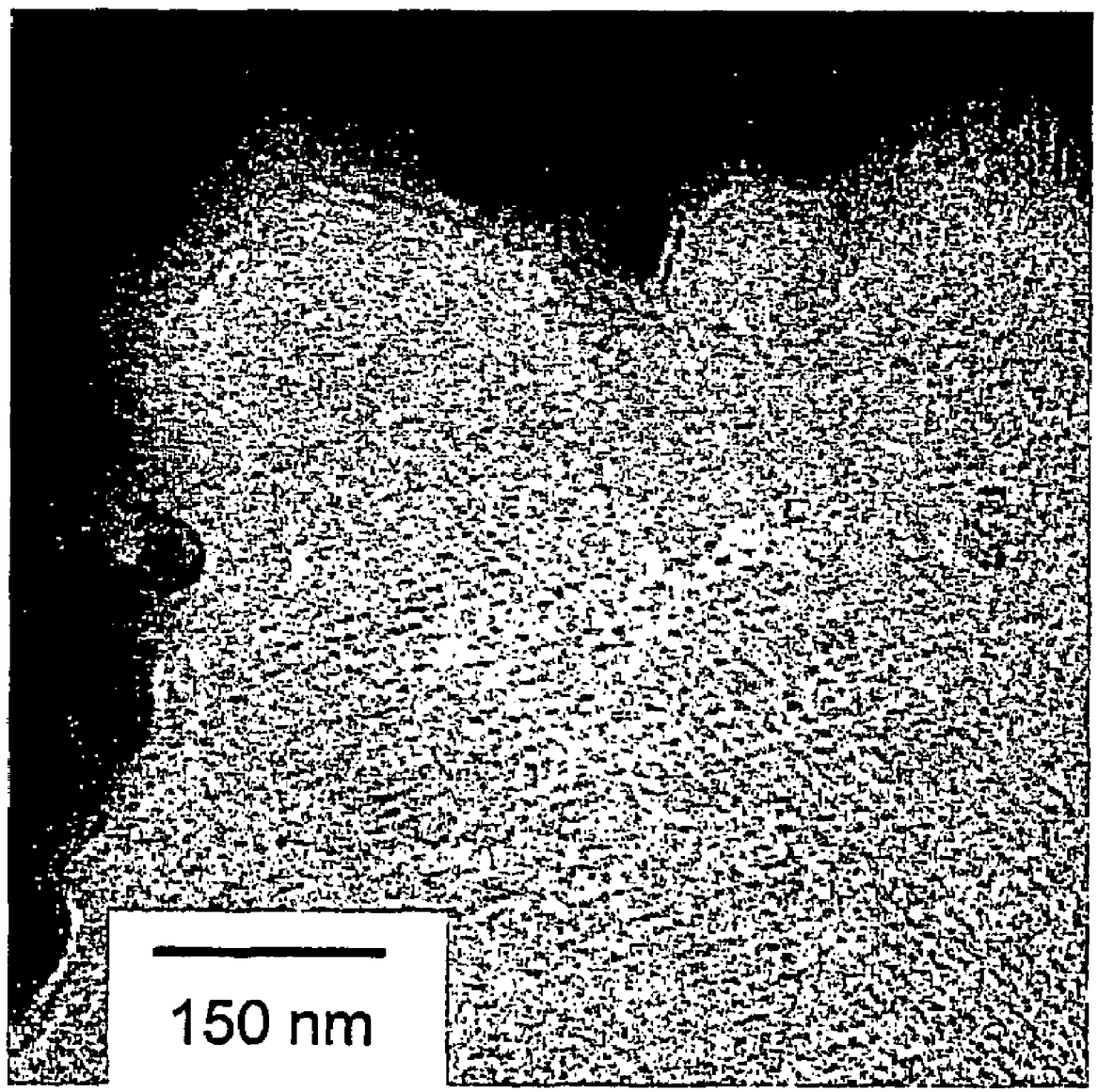

FIG. 13 shows an Energy Filtered TEM thickness map of a typical 2D protein crystal.

Figure 14:
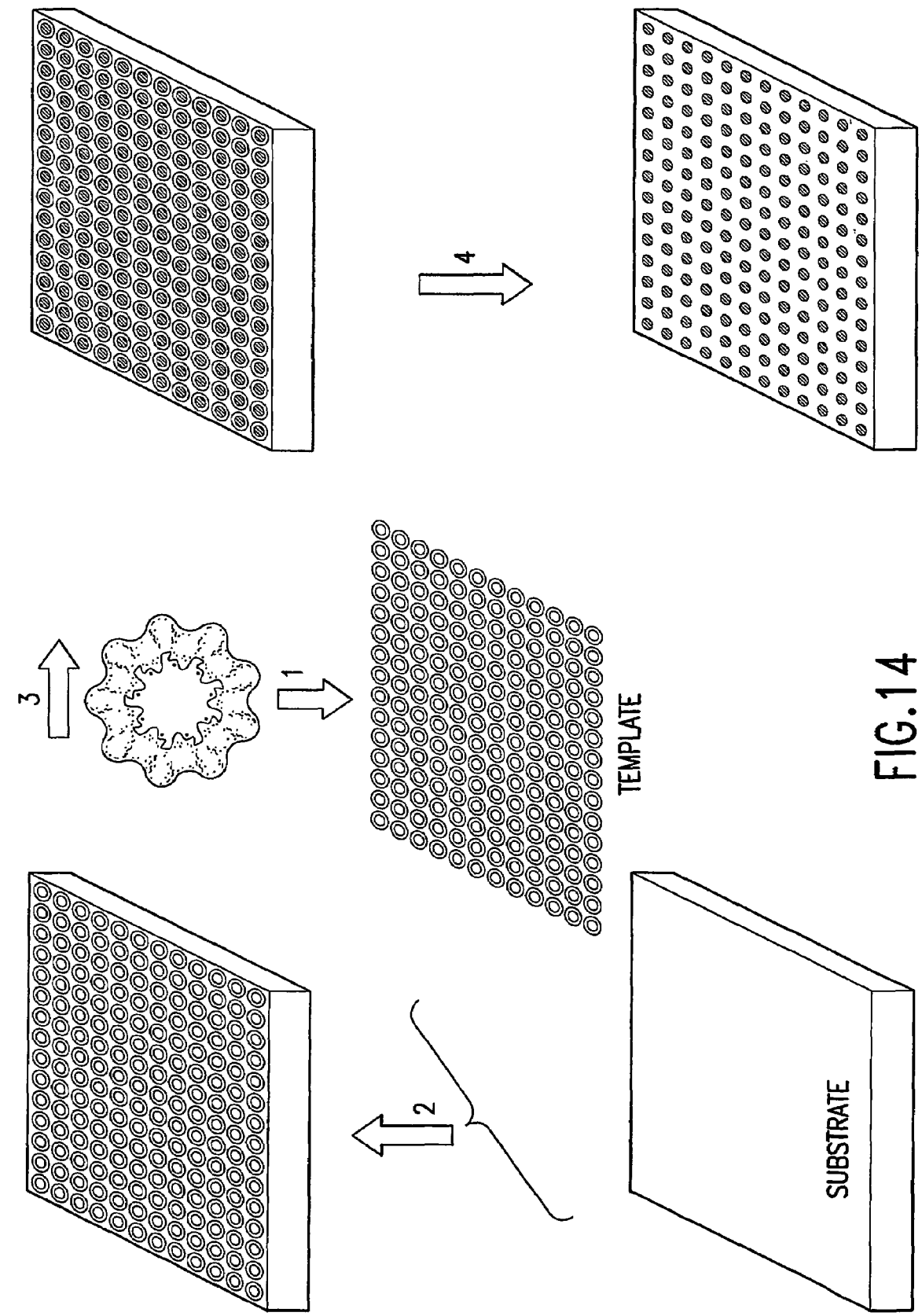

FIG. 14 illustrates steps in the formation of an ordered nanoarray of nanoparticles on a substrate.

FIG. 15 shows the protein sequence alignment of *S. shibatae* TF55 alpha subunit (SEQ ID NO: 39), beta subunit (SEQ ID NO: 1) and gamma subunit (SEQ ID NO: 38).

FIGS. 16A and 16B show the DNA sequence (SEQ ID NO: 37) and amino-acid sequence for *S. shibatae* gamma subunit (SEQ ID NO: 38).

5. DETAILED DESCRIPTION OF THE INVENTION

All patents cited in the specification are hereby incorporated by reference in their entirety. In the case of inconsistencies, the present disclosure, including definitions and terminology, will prevail.

5.1 Terminology

The term "nanotemplate" as used herein, unless otherwise indicated, refers to a composition comprising one or more chaperoning, wherein at least one chaperonin is a mutant chaperonin comprising at least one mutated chaperonin polypeptide. In one embodiment, a nanotemplate is a composite of both wild-type and mutant chaperoning. It is noted that the terms "chaperonin polypeptide" "chaperonin subunit" and "chaperonin polypeptide subunit," are utilized herein interchangeably.

The term "nanostructure" as used herein, unless otherwise indicated, refers to a composition comprising one or more nanotemplates and one or more nanoscale materials, such as nanoparticles and/or quantum dots.

The term "nanoarray" as used herein, unless otherwise indicated, refers an ordered arrangement of nanotemplates and/or nanostructures.

Exemplary devices of nanotemplates include, but are not limited to, electronic, semiconductor, mechanical, nanoelectromechanical, magnetic, photonic, optical, optoelectronic or biomedical devices.

The term "nanounit" as used herein, unless otherwise indicated, refers any of the components or "basic building blocks" of a nanostructure, including, for example, a nanoscale object, such as a nanoparticle or a quantum dot, a nanotemplate, and a wild-type chaperonin or chaperonin polypeptide, or a mutant chaperonin or chaperonin polypeptide.

5.2 Detailed Description of the Preferred Embodiments

The following application relates to nanotemplates, nanostructures, nanoarrays and nanodevices formed from wild-type and mutated chaperonin polypeptides, methods of producing such compositions, methods of using such compositions and particular chaperonin polypeptides that can be utilized in producing such compositions.

Chaperonins

The compositions and devices of the invention, e.g., the nanotemplates, nanostructures, nanoarrays and nanodevices of the invention, comprise, unless otherwise indicated, at least one mutant chaperonin, which comprises at least one mutant chaperonin polypeptide. In many embodiments, the compositions can further comprise chaperonins that do not contain mutant chaperonins. Moreover, in many embodiments, the mutant chaperonins can further comprise non-mutant, that is, wild-type chaperonins. Non-limiting examples of chaperonins and chaperonin polypeptides that can be utilized as part of the methods and compositions of the present invention are described herein. Non-limiting examples of mutant chaperonins and mutant chaperonin polypeptides that can be utilized as part of the methods and compositions of the present invention are described hereinbelow, in the following section.

Figure 1:
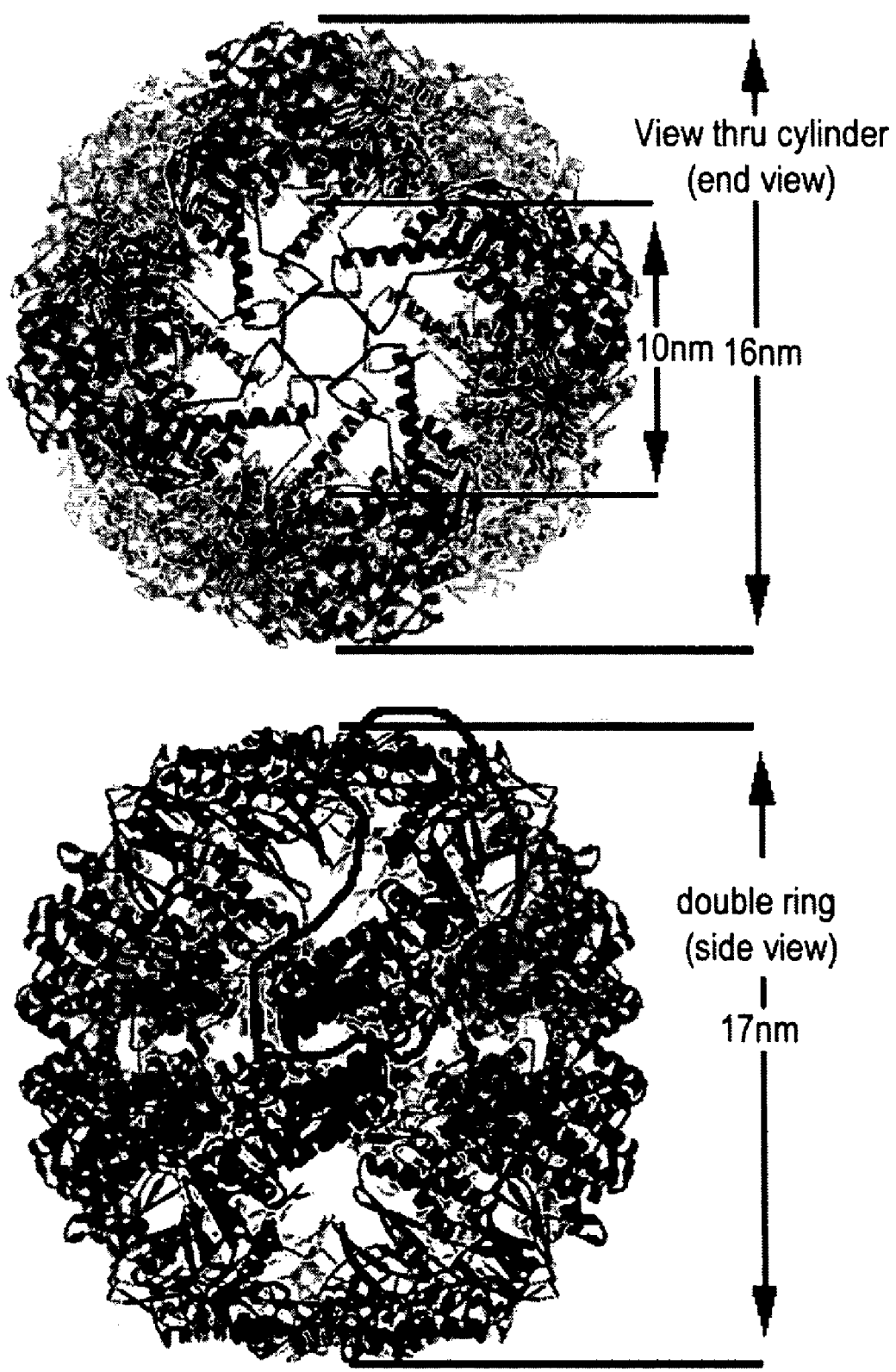

Chaperonins (also referred to herein as "cpn60s") are double-ringed structures comprising approximately 60 kDa (+5 kDa) proteins (see, e.g., Hartl et al., 2002, *Science* 295, 1852-8). In nature, chaperonins are ubiquitous and essential subcellular structures comprising 14, 16, or 18 protein subunits, arranged as two stacked rings approximately 16 to 18 nm tall by approximately 15 to 17 nm wide, depending on their species of origin. FIG. 1 illustrates an end and side view of a chaperonin that comprises 16 subunits, i.e., eight subunits per ring.

The sequence and three dimensional structural similarities between chaperonins and chaperonin polypeptides allows any chaperonin polypeptides and chaperonins to routinely be utilized as part of the compositions and devices of the present invention. In addition, such similarities allow any chaperonin polypeptides to routinely be able to used to derive the mutant chaperonin polypeptides that comprise the compositions and devices of the invention. The sequence and three dimensional structural similarity of the subunits among the different types of chaperonins, which is illustrated by the sequence alignment depicted in FIGS. 2A-2R and the structural overlap as illustrated in a representative comparison depicted in FIG. 3, provides the basis for the formation of the nanotemplates, nanostructures, nanoarrays and nanodevices of the invention.

Chaperonins have been classified into two groups, Group I and Group II, based on sequence and structural comparisons. (See, e.g., Trent et al., 1991, *Nature* 354, 490-493; Horwich et al., 1993, *Phil. Trans R. Soc. Lond.* 339, 313-326). Group I or Group II chaperonins or chaperonin polypeptides, or mutant chaperonins comprising at least one mutant Group I or Group II chaperonin polypeptide, can be utilized as part of the compositions and devices of the present invention. In one embodiment, the chaperonins or mutant chaperonins comprise Group I chaperonin polypeptides and/or mutant chaperonin polypeptides. In another embodiment, the chaperonins and/or mutant chaperonins comprise Group II chaperonin polypeptides and/or mutant chaperonin polypeptides. In yet another embodiment, the chaperonins or mutant chaperonins comprise Group I and Group II chaperonin polypeptides and/or mutant chaperonin polypeptides.

Group I chaperonins are from bacteria and the bacterial-derived organelles of Eukarya (mitochondria and chloroplasts), while group II chaperonins are from Archaea and eukaryotic cytosol. See, e.g., U.S. Pat. No. 5,428,131 to Trent et al. that describes the expression of endogenous, wilde-type TF55 *S. shibatae*, and provides a comparison of a group I chaperonin (GroEL) to the group II chaperonin TF55.

Wild-type Group I chaperonins are composed of seven subunits in each of the two rings of the double-ring structure. The wild-type cpn60 proteins, which comprise about 550 to about 580 amino acid residues, have been described by different names in different species, including, but not limited to *Escherichia coli* GroEL protein, Cyanobacterial groEL analogues, *Mycobacterium tuberculosis* and *leprae* 65 Kd antigen, *Coxiella burnetti* heat shock protein B (gene htpB), *Rickettsia tsutsugamushi* major antigen 58, Chlamydial 57 Kd hypersensitivity antigen (gene hypB), Chloroplast RuBisCO subunit binding-protein alpha and beta chains, Mammalian mitochondrial matrix protein P1 (mitonin or P60), and Yeast HSP60 protein. Any of these chaperonins, or mutants thereof, can, for example, be utilized as part of the compositions and devices of the present invention.

In one embodiment, e.g., when utilizing Group I chaperoning, chaperonin polypeptides, and/or mutant chaperonins and/or mutant chaperonin polypeptides, a cochaperonin can be utilized in forming the higher order structures of the invention. As such, in one example of such an embodiment, a composition or device of the invention further comprises a cochaperonin. Cochaperonins are well known to those of skill in the art. See, e.g., Harris et al., 1995, *J Structural Biol.* 115, 68-77). In another, non-limiting example of such an embodiment, a cochapreonin can be utilized in producing nanofilaments. For example, the cpn60 in the bacterium *E. coli* (GroEL) in nature is associated with a single ring structure composed of 10 kDa proteins (co-chaperonin or cpn10) called "GroES." As such, a GroES polypeptide represents an exemplary, non-limiting species of cochaperonin that can be utilized in conjunction with Group I chaperoning, e.g., GroEL or GroEL-derived chaperoning, chaperonin polypeptides, and/or mutant chaperonins or chaperonin polypeptides. In different embodiments of the invention, the compositions, e.g., nanotemplates or nanostructures, are formed from one or more chaperonins with the cochaperonin on one or both ends of the chaperonin.

Group II chaperonins are composed of identical or diverse subunits arranged in rings of eight or nine subunits, depending on the organism. In the yeast *Saccharomyces cerevisiae*, for example, there is evidence for eight different subunits in each ring (Lin et al., 1997, *Proc. Natl. Acad. Sci. USA* 94, 10780-10785). Among the Archaea some thermophilic methanogens (e.g., *Methanopyrus kandleri*, *Methanococcus jannaschii*, *Methanococcus thermolithotrophicus*) have chaperonins with identical subunits (Furutani et al., 1998, *J. Biol. Chem.* 273, 28399-28407), while in the mesophilic methanogen *Methanosarcina acetivorans* there are five different subunits (Galagan et al., 2002, *Genome Research* 12, 532-542). Of the 50 archaeal chaperonin sequences in the databases most have >40% amino acid sequence identity. Any of these chaperoning, or mutants thereof, can, for example, be utilized as part of the compositions and devices of the present invention.

The majority of group II chaperonins in Archaea have eight subunits per ring and are referred to as "thermosomes" (Klumpp, M., and Baumeister, W., 1998, *FEBS Letters* 430, 73-77), but the chaperonins in the thermoacidophilic Archaea in the family Sulfolobales have nine subunits per ring (Trent et al., 1991, *Nature* 354, 490-493; Marco et al., 1994, *FEBS* 341, 152-155). These *Sulfolobus octadecameric* chaperonins are referred to as "rosettasomes" (Kagawa et al., 1995, *J. Mol. Biol.* 253, 712-725) to distinguish them from thermosomes. Other examples of thermosomes include chaperonins from *Pyrodictium occultum*, *Thermoplasma acidophilum* and *Methanopyrus kandleri* (Ellis et al., 1998, *J. Struc. Biol.* 123, 30-36). It has previously been reported that rosettasomes are composed of two types of HSP60s known as TF55 α and β, that TF55 α and β are among the most abundant proteins in *S. shibatae* grown at optimal temperatures (75-83° C.), and that their synthesis increases at heat-shock temperatures (85-88° C.) (Kagawa et al., 1995, *J. Mol. Biol.* 253, 712-725). A third related subunit of *S. shibatae*, has also been identified by sequence analyses (Archibald et al., 1999, *Current Biology* 9, 1053-1056). Sequence information from *S. solfataricus* (Charlebois et al., 1998, *Current Opinion in Microbiology* 1, 584-588) allowed TF55 alpha, beta, and gamma expression to be predicted based on codon usage (Karlin et al., 2001, *J. Bacteriol.* 183, 5025-5040). Chaperonins from eukaryotic cytosol are referred to as "TCP1," which identifies one of the proteins comprising the ring structure, "TriC" which means TCP1 ring chaperonin, or "CCT" which means chaperonin containing TCP1. Any of these chaperonins, or mutants thereof, can, for example, be utilized as part of the compositions and devices of the present invention.

In one embodiment, the chaperonins comprise HSP60s (heat shock proteins), which are proteins induced by heat stress.

Figure 2A:
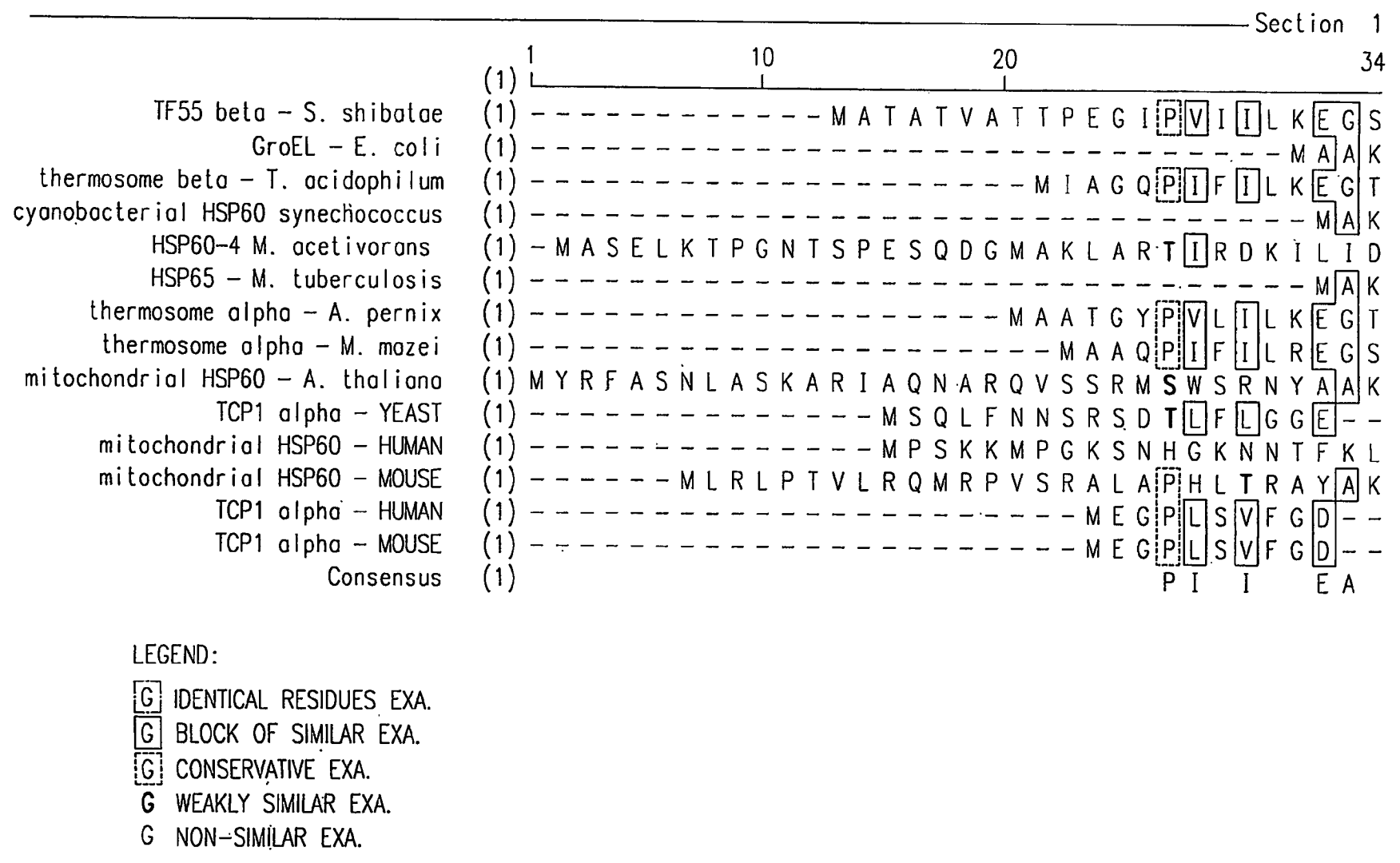
Figure 2C:
Figure 2E:
Figure 21:
Figure 2J:
Figure 20:
Figure 3:
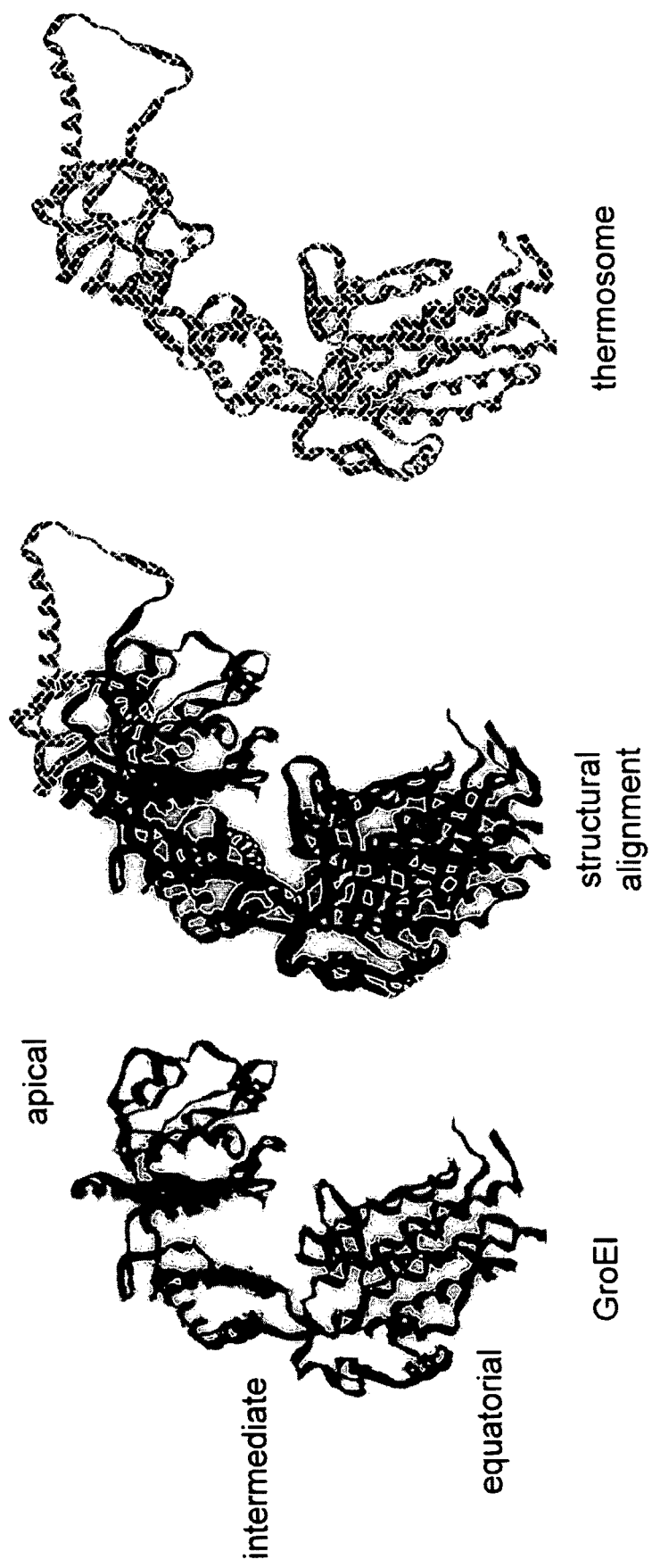
FIG. 3 shows a structural alignment of the archaeal chaperonin (thermosome) and the bacterial chaperonin (GroEL), indicating the structural similarities between group I and group II chaperonins. The black areas of the structural alignment indicate where the features of the two chaperonin subunits overlap.
Figure 2B:
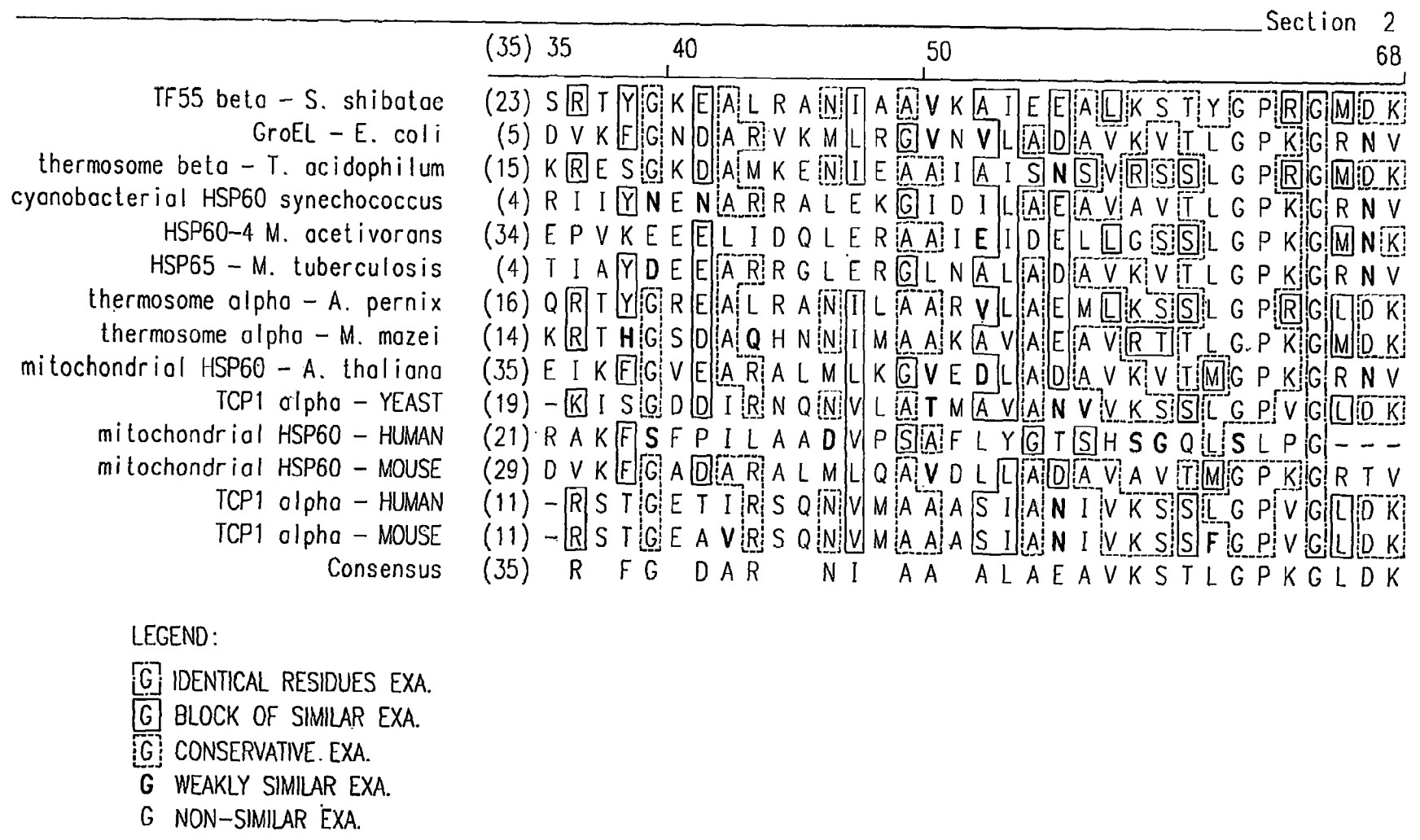
Figure 2D:
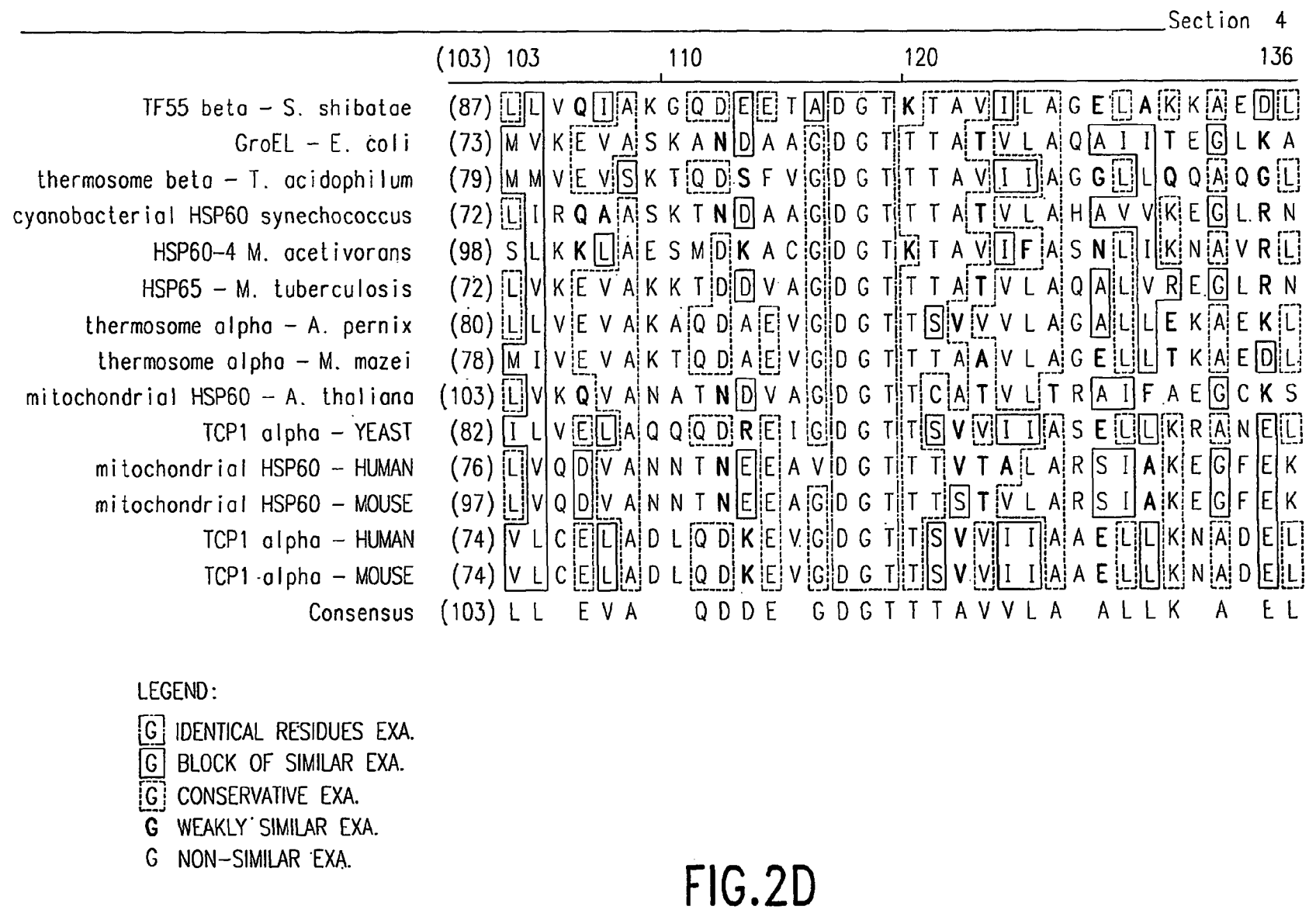
Figure 2F:
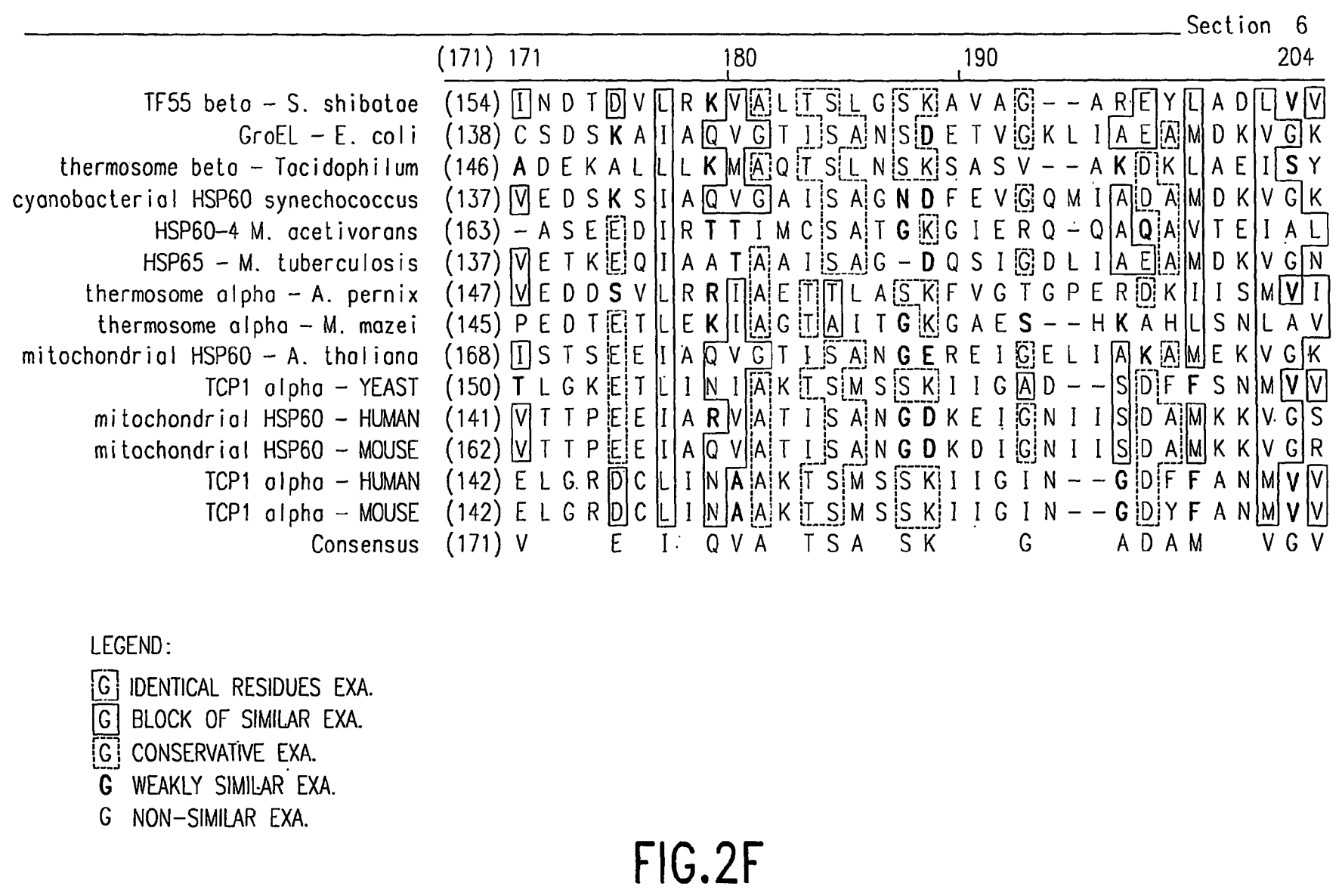
Figure 2G:
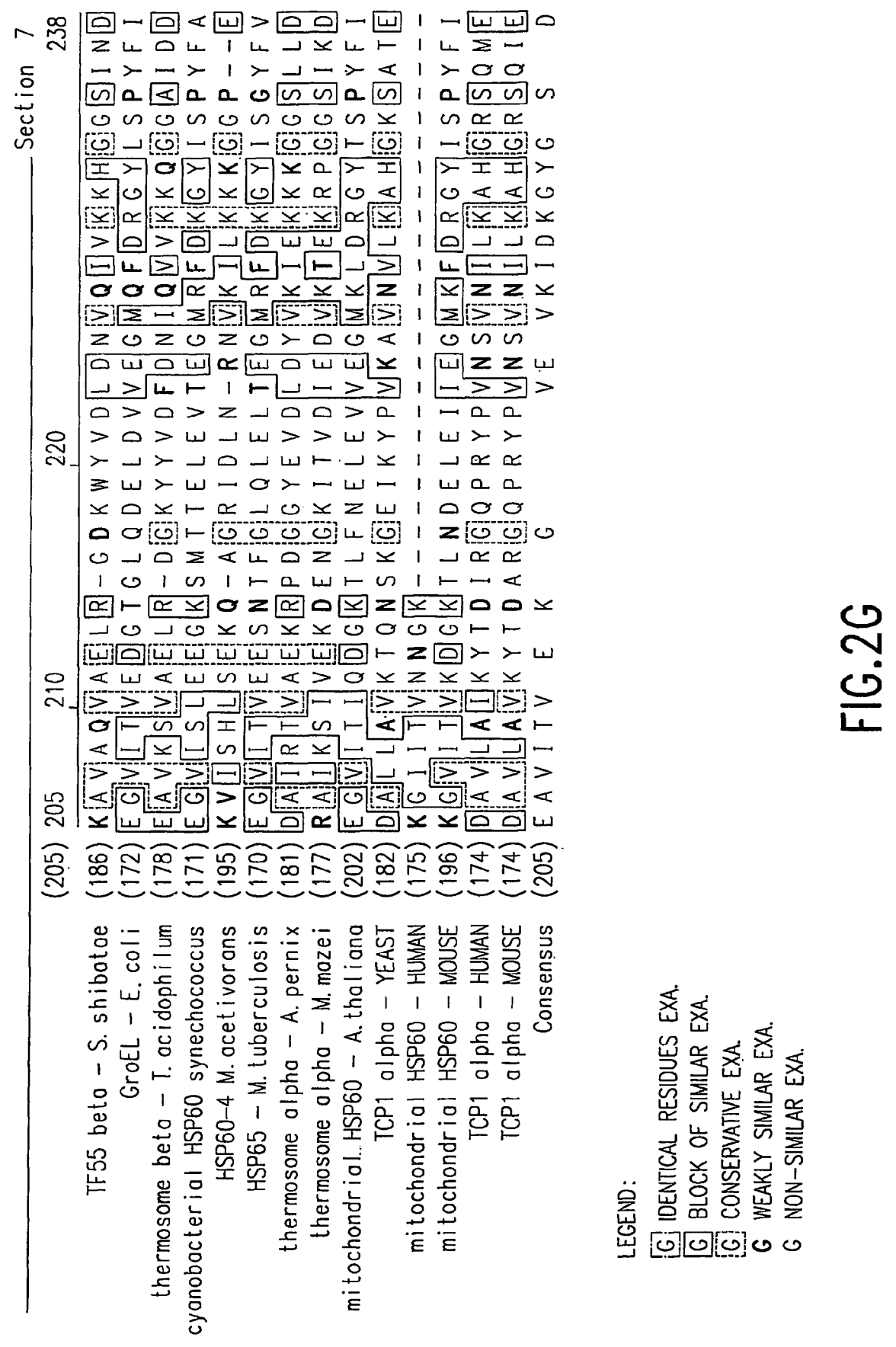
Figure 2H:
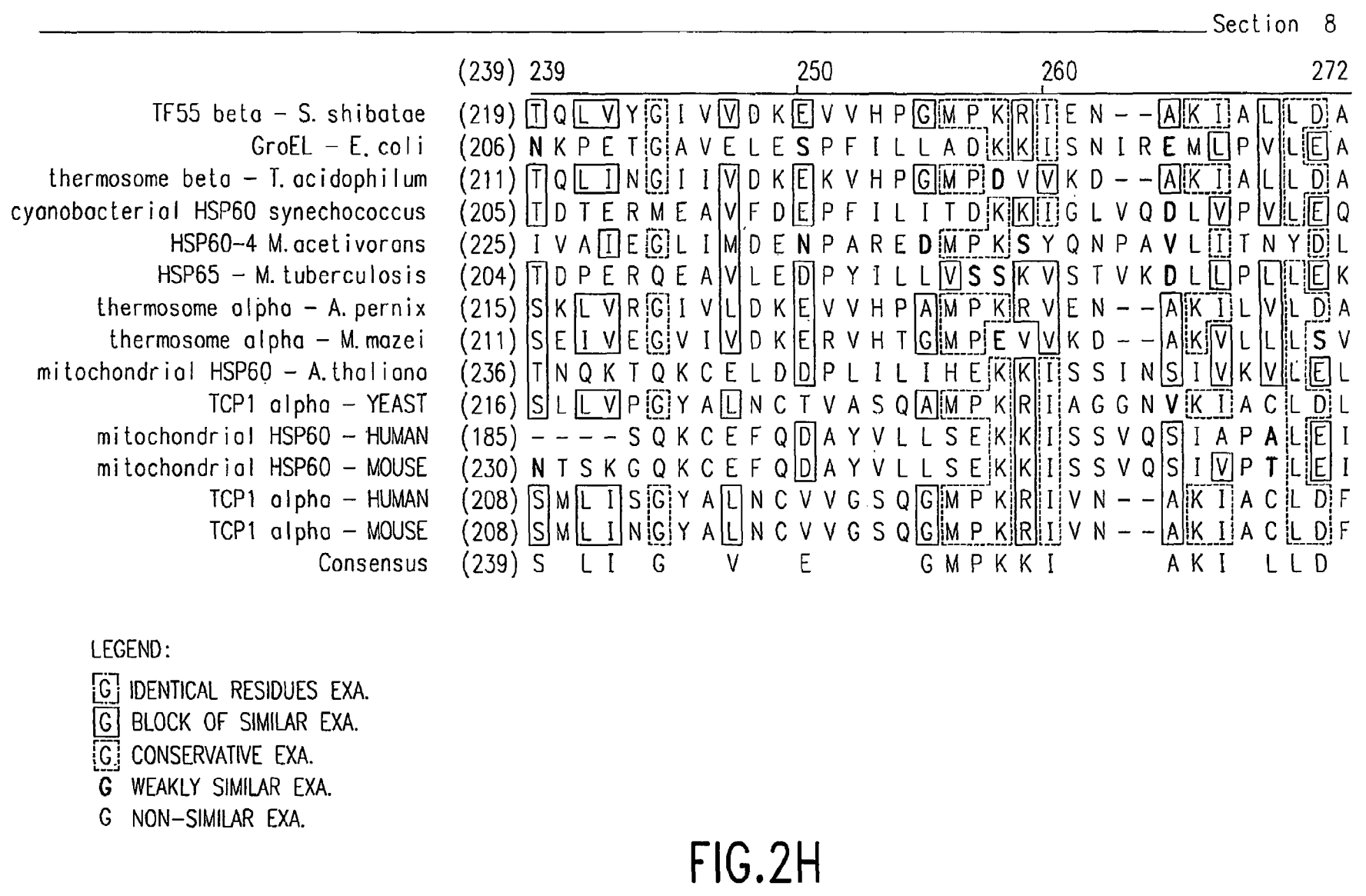

FIGS. 2A-2R show protein sequence alignments covering a representative set of Groups I (bacteria) and Group II (archaea and eukarya) chaperonins. The protein sequence are sequences for *S. shibatae* TF55 beta subunit (SEQ ID NO: 1), bacterial *E. coli* GroEL (SEQ ID NO:2), thermosome *T. acidophilum* beta subunit (SEQ ID NO:3), cyanobacterial synechococcus HSP60 (SEQ ID NO:4), *M. acetivorans* HSP60-4 (SEQ ID NO:5), *M. tuberculosis* HSP65 (SEQ ID NO:6), thermosome *A. pernix* alpha subunit (SEQ ID NO:7), thermosome *M. mazei* alpha subunit (SEQ ID NO:8), mitochondrial *A. thaliana* HSP60 (SEQ ID NO:9), yeast TCP1 alpha subunit (SEQ ID NO:10), human mitochondrial HSP60 (SEQ ID NO:11), mouse mitochondrial HSP60 (SEQ ID NO:12), human TCP1 alpha subunit (SEQ ID NO:13), mouse TCP1 alpha subunit (SEQ ID NO:14), and the consensus (SEQ ID NO:15). White letters on a black background, solid lines, and dashed lines surround the regions of the sequence alignment containing identical residues, a block of similar residues, and conservative matches, respectively.

For purposes of wild-type chaperonins and chaperonin polypeptides, such sequence similarity serves to illustrate that fact that any chaperonin or chaperonin polypeptide routinely can be utilized as part of the compositions and devices of the present invention, either alone or combination. For purposes of mutant chaperonins and chaperonin polypeptides, as discussed in detail in the next section, such sequence similarity serves to provide teaching that allows for routine manipulation of sequences in producing and modifying mutant chaperonin polypeptides that can become part of mutant chaperonins in the compositions and devices of the present invention.

While group I chaperonins can have greater than 50% sequence identity, sequence identity among Group II chaperonins can be on the order of less than 33%. Despite the sequence variations among the cpn60 subunits from the different species, however, group I and group II cpn60 subunits share significant structural similarity. FIG. 3 shows a structural comparison between a subunit of the archaeal (*Thermoplasma acidophilum*) thermosome and the bacterial (*E. coli*) GroEL chaperonins. The alignment was performed using an algorithm based on the iterative dynamic programming approach as outlined Gerstein, M. & Levitt, M., Protein Science 7, 445-456, 1998; and Gerrstein, M. & Levitt, M, Proc. of ISMB-96, pp. 59-67, 1996.

For purposes of wild-type chaperonins and chaperonin polypeptides, such three dimensional structural similarity serves to illustrate that fact that any chaperonin or chaperonin polypeptide routinely can be utilized as part of the compositions and devices of the present invention, either alone or combination. For purposes of mutant chaperonins and chaperonin polypeptides, as discussed in detail in the next section, such sequence similarity serves to provide teaching that allows for routine manipulation of sequences in producing and modifying mutant chaperonin polypeptides that can become part of mutant chaperonins in the compositions and devices of the present invention.

The two subunits exhibit very similar structures, in that both possess an equitorial, an intermediate and an apical region. Even though these two examples of cpn60 subunits are farther apart by sequence than most cpn60 subunits, as evidenced by the very little similarity in their sequence alignments (see FIGS. 2A-2R), the crystal structures for each reveal that they share considerable structural identity—most all helical, sheet, and random coil regions correspond, as shown in black in the center panel. Variations in structure are tolerated in the apical domain, as evidenced by the loop of the thermosome, while the equitorial domains adopt similar conserved folding motifs.

It is noted that, while the chaperonins observed to date comprise seven, eight or nine subunits per ring, the present invention provides methods and compositions of exploiting chaperonins with any number of subunits per ring for the compositions, e.g., nanotemplates, nanostructures, and nanoarrays, and nanodevices of the invention.

Chaperonins from the different species can comprise only a single type of subunit or they can have different types of subunits (e.g., archeal chaperonins comprising alpha, beta, gamma, etc.). These subunits are called alpha subunits, beta subunits, or gamma subunits, due to some differences in the protein sequences of the subunits of a given species. As is known to one of ordinary skill in the art, in some species yet more varieties of subunits exist. The structure of chaperonins Ellis et al., 1998, *J. Struc. Biol.* 123, 30-36 describes a chaperonin from *Sulfolubus solfataricus* with a 2:1 ratio of alpha:beta subunit composition of the nine-membered ring (rosettasomes). The present invention provides means of assembling chaperonins from only a single type of wild-type or mutated chaperonin polypeptide, or from various proportions of the different wild-type or mutated chaperonin polypeptides.

In a specific embodiment, HSP60s (heat-shock proteins) in organisms living at high temperatures, called "thermophiles," are the source of the wild-type and mutated chaperonin polypeptides of the present invention. These proteins are present in all organisms and are among the most abundant proteins in extreme thermophiles, e.g., in one of the highest temperature thermophiles *Pyrodictium occultum*, they reportedly account for 73% of total protein (Phipps et al., 1991, *The EMBO Journal* 10(7), 1711-1722).

Chaperonin and mutant chaperonin polypeptides can routinely be expressed using standard techniques well known to those of skill in the art. For example, sequences encoding the chaperonin polypeptide and/or mutant chaperonin polypeptide can be introduced into a host cell, e.g., a prokaryotic, for example, an *E. coli* or *Salmonella* host cell, eukaryotic, for example, a yeast or mammalian host cell, and expressed and isolated using standard recombinant techniques.

In a non-limiting example, a sequence encoding a thermostable chaperonin, e.g. a thermostable HSP60, can be transferred into *E. coli* and grown at temperatures standard for the cell. The expressed polypeptide can then be easily purified from *E. coli* proteins by heating and centrifugation. The thermolabile *E. coli* proteins precipitate leaving the thermostable polypeptide greater than 90% pure after a centrifugation. Another advantage is that HSP60 nanotemplate structures such as rings, tubes, and filaments (to be described in detail below) bind to DNA and RNA using the method of "gel shift" to proteins by the method of autoradiography, and to liposomes and lipid monolayers.

Mutant Chaperonins

The present invention provides methods for forming variants of chaperonin polypeptides through selective mutation of the polypeptide, and then exploiting the ability of these variants to self-assemble into higher-order structures under various conditions for forming the compositions and devices, e.g., nanotemplates, nanostructures, nanoarrays and nanodevices, of the invention.

The compositions and devices of the invention, e.g., the nanotemplates, nanostructures, nanoarrays and nanodevices of the invention, comprise, unless otherwise indicated, at least one mutant chaperonin, which comprises at least one mutant chaperonin polypeptide. Non-limiting examples of mutant chaperonins and mutant chaperonin polypeptides that can be utilized as part of the methods and compositions of the present invention are described herein.

In referring to mutant chaperonins and mutant chaperonin polypeptides, the term "mutant" refers to a difference relative to what is considered a wild-type sequence. Representative, non-limiting examples of wild-type chapernin polypeptide sequences are presented in FIGS. 2A-2R. In addition, in one embodiment, a mutant chaperonin polypeptide is one that, when present in a cell or organism, yields an observable phenotype that differs from the phenotype observed in its absence, that is, when only a corresponding wild-type sequence is present. Generally, a mutant chaperonin sequence refers to a sequence that does not occur in nature at a greater than 10% (+/−10%) allelic frequency, as measured by standard methods and available data. For example, an example of a mutant *S. shibatae* chaperonin polypeptide is one that is expressed by an allele that is present in the organism at no greater than 10% (+/−10%) alleic frequency.

As discussed above, the sequence and three dimensional structural similarities between chaperonins and chaperonin polypeptides allows any chaperonin polypeptides and chaperonins to routinely be utilized as part of the compositions and devices of the present invention. Moreover, such similarities allow any chaperonin polypeptides to routinely be able to used to derive the mutant chaperonin polypeptides that comprise the compositions and devices of the invention. The sequence and three dimensional structural similarity of the subunits among the different types of chaperoning, which is illustrated by the sequence alignment depicted in FIGS. 2A-2R and the structural overlap as illustrated in a representative comparison depicted in FIG. 3, provides the basis for the formation of the nanotemplates, nanostructures, nanoarrays and nanodevices of the invention.

Further, the details of the structure of chaperonins can be solved at atomic-resolution (2.3-2.8 Å) (See, e.g., Figure; 1 and Xu, Z. et al., 1997, *Nature* 388, 741-750; and Ditzel, L., J. Lowe, et al., 1998, *Cell* 93, 125-138). This provides detailed information about the location of every atom of every amino acid in the double ring structure (e.g., FIG. 4), and can be used to routinely choose chaperonin sites for modification and can routinely assess the properties of chaperoning, in particular, mutant chaperoning.

Utilizing the sequence and three dimensional structural similarities among chaperonins and chaperonin polypeptides, as well as the ability to solve at atomic-resolution the structure of particular chaperonins and chaperonin polypeptides, the structure of the chaperonin polypeptides can be manipulated to influence, for example, their assembly, strength, and binding properties, as well as the assembly, strength and binding properties of the resulting chaperonins and, in turn, compositions and devices comprising the chaperoning.

Such structural similarities can be utilized in a number of different ways in choosing appropriate mutants. For example, a mutant in one species that exhibits a desirable characteristic can be introduced into a corresponding position in another chaperonin by utilizing the sequence similarity and/or the three dimensional structural similarity between the chaperoning. In one such embodiment, for example, the mutant *S. shibate* sequences successfully utilized in the examples presented below can routinely be introduced into other chaperonin polypeptides by these techniques, and the resulting mutant chaperonin polypeptides can be used in the compositions and devices of the invention.

Standard methods well known in the art which allow changing specific amino acids in chaperonin polypeptides, such as the method of site-directed mutagenesis, regions of the subunits can be modified, and the resulting chaperonin polypeptides can routinely be tested for their ability to produce chaperonins and, for example, nanotemplates, nanostructures, nanoarrays and nanodevices, e.g., their ability to assemble into tubes and filaments can be tested. In one embodiment, for example, amino acid tails can be attached to chaperonin polypeptide subunits that do not inhibit their ability to assemble into rings and tubes, and that allow the binding of various nanoscale materials, such as metals, at various locations of the chaperoning, including inside the chaperonin structure. In one embodiment, one of the three HSP60 subunits (beta) from *Sulfolobus shibatae*, an organism that lives in geothermal hot-springs and grows at temperatures of up to 85° C./pH 2.0 is used to form mutant chaperoning. The chaperonins in *S. shibatae* are octadecameric with nine subunits per ring. FIG. 15 shows the protein sequence alignment of *S. shibatae* TF55 alpha subunit (SEQ ID NO: 39), beta subunit (SEQ ID NO: 1) and gamma subunit (SEQ ID NO: 38). The beta subunit can be chosen for a particular application based on such factors as its thermostability, which makes it easy to purify as a recombinant protein, and the availability of sequence and structural information, which can guide the genetic manipulations.

Figure 4:
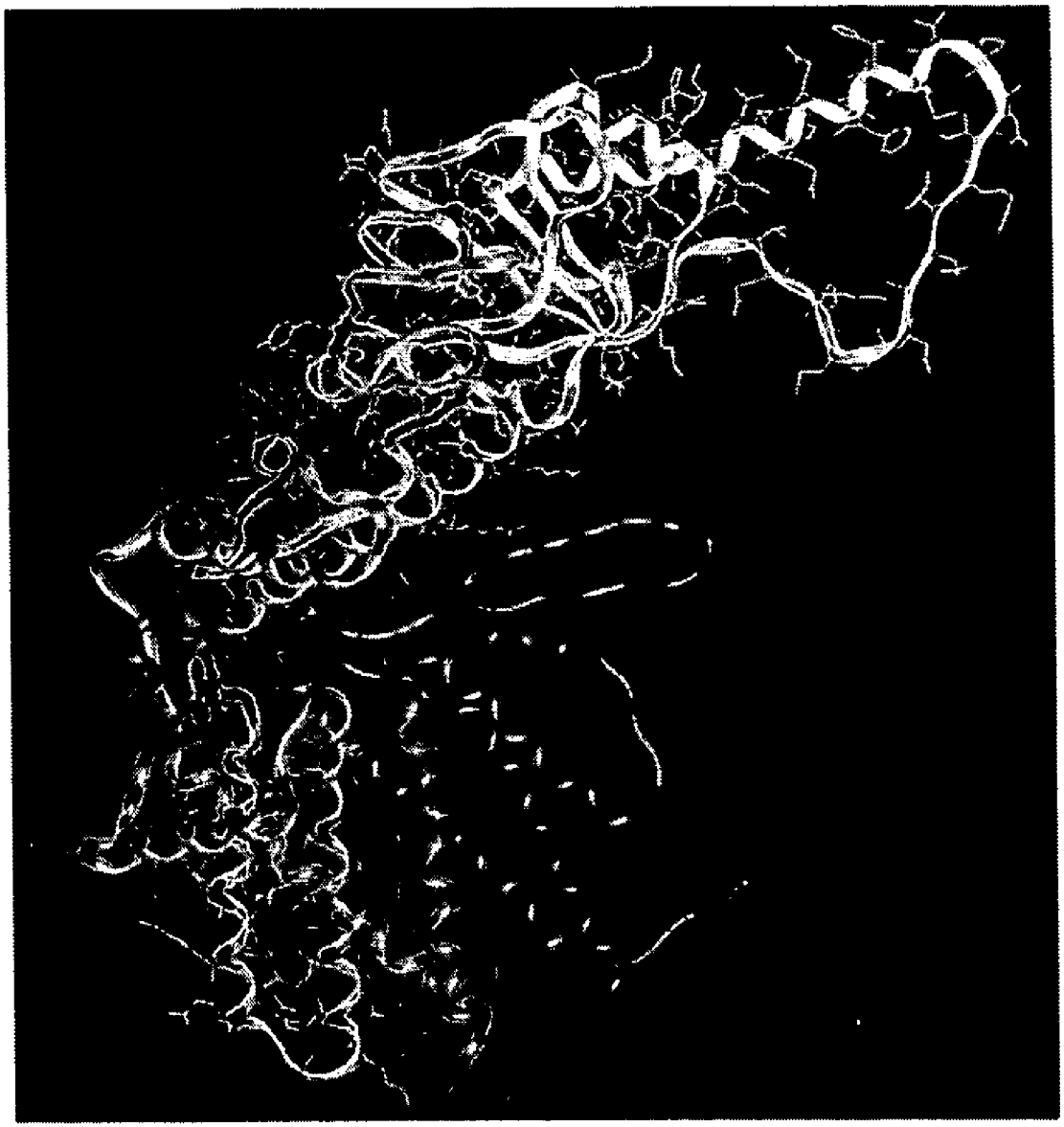
FIG. 4 shows the detailed structure of a Group II chaperonin subunit.
Figure 5A:
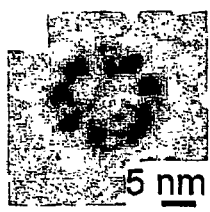
Figure 5B:
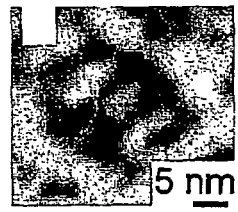
Figure 5C:
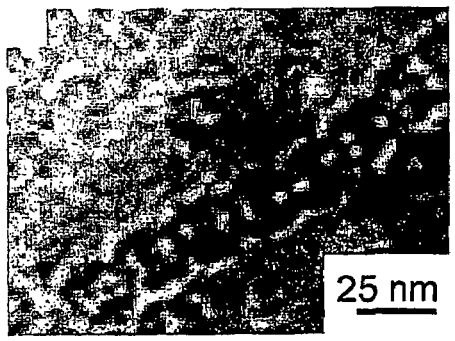
Figure 5D:
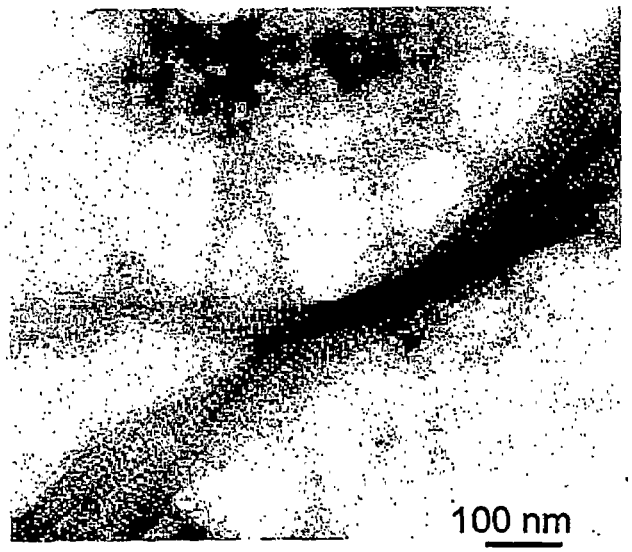

In general, the chaperonin subunits have many regions that can accommodate additions or deletions in each of their three domains-equatorial, intermediate, and apical domains, as illustrated in FIG. 3. FIG. 4 shows the detailed structure of a Group II chaperonin subunit that can be used in making a choice of mutations. The mutations can be performed to engineer one or more specific binding sites at different locations on a chaperonin for the attachment of a quantum dot or a nanoparticle, as is described in greater detail below, or for the attachment of different types of molecules or polypeptides. The mutations can modify the dimensions of the resulting chaperonin, such as length, inner pore diameter, outer diameter, etc., or it can be performed to present specific binding sites on the apical, intermediate or equitorial regions of the chaperonin. The choice of mutation depends on the desired structure for the different applications of the present invention, including the formation of nanotemplates, nanostructures, nanoarrays and nanodevices.

The choice of mutations to make depends on the desired structure of the resulting chaperonin, and can routinely be ascertained. In a specific embodiment, the mutated chaperonin polypeptide subunits include ones that assemble into higher order structures with less than seven subunits per ring or more than nine subunits per ring. Mutations can be made to the subunit sequence such that the resulting subunit variants assemble into a structure with any number of subunits per ring. Mutations introduced that change in number of subunits per ring can, for example, be used to modify the diameter of a resulting ring nanostructure.

Factors that affect the choice of which chaperonin polypeptides to manipulate (e.g., from what species, which subunit (s), etc.), and what mutations are to be made to them, include the desired dimensions, i.e., length, pore diameter, and outer diameter, of the resulting chaperonin product, or introduction of a selective binding site anywhere on the polypeptide. The subunits of both group I and group II chaperonins will tolerate a point mutation at any position. When sequence alignments are used in determining mutation positions, mutations at similar, non-identical residues, as determined by sequence alignment, being preferred, and non-conserved positions, as determined by sequence alignment being more preferred. When three dimensional structural alignments are used in determining mutation positions, a structural alignment of chaperonin subunits, such as that of FIG. 3, can serve as a guide in deciding where on the subunit to perform the mutation. The loops and turns from the two structures that do not directly superimpose can be choices of points to perform mutations, including deletions and insertions. In addition, the N- and/or C-termini of the polypeptides are generally amenable to manipulation.

In one embodiment, a choice of deletion of the amino acid loop at the apical domain of a group II chaperonin is made through comparison of the structural alignment of FIG. 3, and with the observation that the loopless group I chaperonin subunit assembles into the double-ring structure of the chaperonin. In another embodiment, the N- or C-terminus is removed. In yet another embodiment, the N- or C-terminus is modified by inserting a sequence. The sequence can be inserted for binding specificity, such as by introducing cysteine or tyrosine which can be modified chemically.

In a specific embodiment, the mutant chaperonin comprises one more mutated chaperonin polypeptide sequences with one or more point mutations. An exemplary point mutation in TF55-beta from *Sulfolobus shibatae* results from residue 299 being changed from cysteine to alanine and residue 270 changed from glutamine to cysteine. In another embodiment, the mutant chaperonin comprises one more mutated chaperonin polypeptide sequences with one or more sequences deleted. An exemplary deletion in TF55-beta results from *Sulfolobus shibatae* with residues 254 to 281 deleted. In another embodiment, the mutant chaperonin comprises one or more mutated chaperonin polypeptide sequences with one or more polypeptide sequences inserted. An exemplary insertion in TF55-beta results from *Sulfolobus shibatae* with peptides that possess binding specificity inserted. As discussed above, corresponding mutations can be routinely introduced into any other chaperonin polypeptide.

In another embodiment, the peptides are designed to bind nanoscale materials such as nanoparticles and quantum dots. In yet another embodiment, the peptides are designed to bind only to specific surfaces. Still other modifications can also be made in the equatorial domains that include deletions, substitutions and additions to the N- and C-termini with little effect on the formation of chaperonins or nanotemplates such as filaments. For example, up to about 5, 10, 15, 20, 25, or 30 amino acids of the N- and/or C-terminus of the chaperonin polypeptide can be modified, e.g., deleted. For example, GroEL can be modified by removing up to about 27 amino acids from the C-terminus without impairing its ability to assemble into double rings.

Additional references that describe possible mutations of specific residues of the polypeptides are contained in the review article Fenton et al., 1997, *Protein Science* 6, 743-760.

The sequence alignment of FIGS. 2A-2R indicates that the regions that have been manipulated in *S. shibatae* also exist in other species. Whatever mutations have been successfully made in one species may be successfully others species, whether bacterial, other archea or eukarya. The corresponding regions of the sequence alignments can therefore serve as a guide in choice of manipulations to produce variants in other species, combined with the knowledge of the region of the chaperonin subunit that the given mutated sequence is located. A successful mutation of the chaperonin polypeptide from any given species is indicated if the mutated chaperonin polypeptide retains its ability to assemble into the higher order structures of the invention, including the nanotemplates, nanostructures, nanoarrays and nanodevices.

Figure 7A:
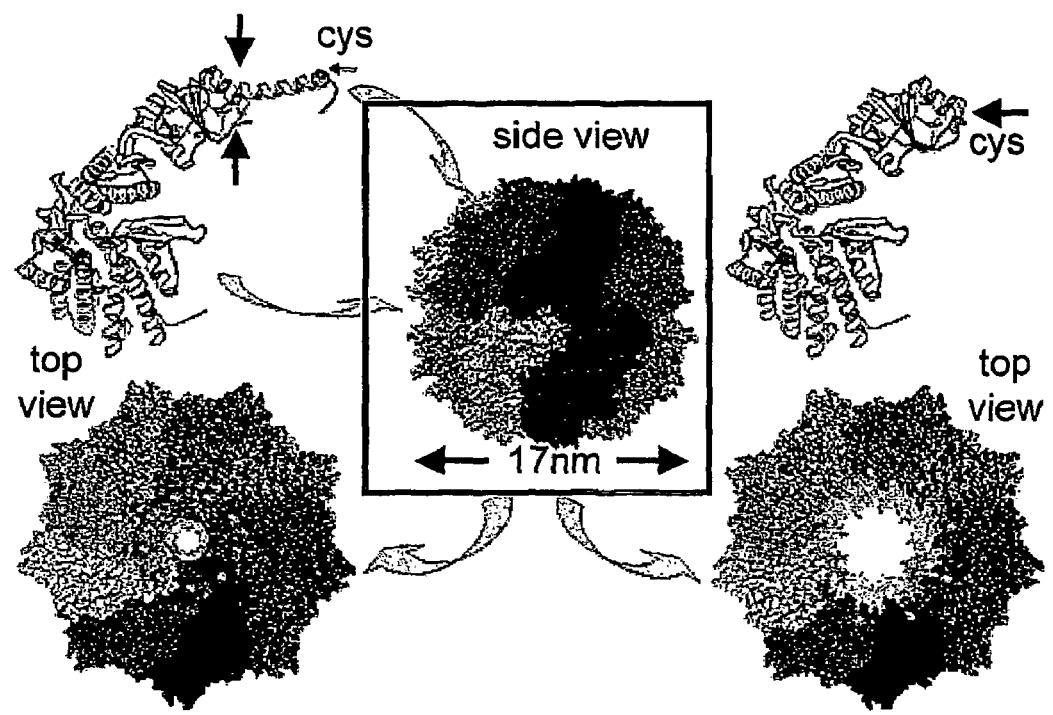
Figure 7B:
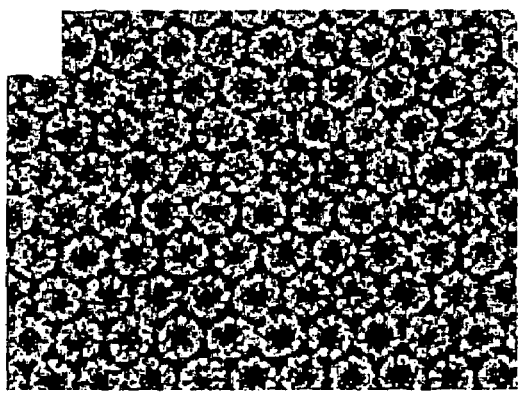
Figure 7C:
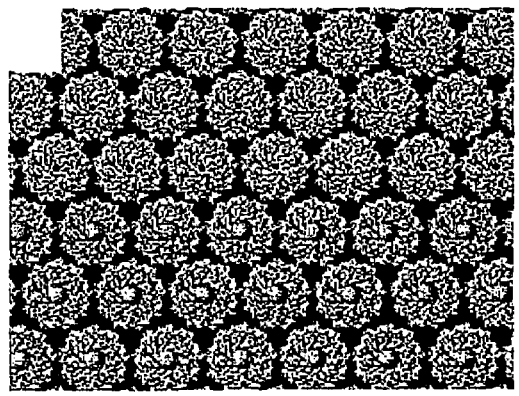
Figure 7D:
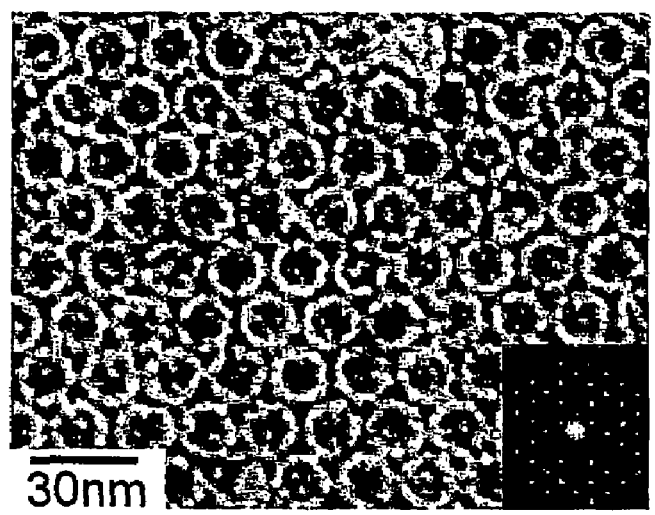

In a specific embodiment, guided by structural information, the beta subunit of *Sulfolobus shibatae* is genetically modified to add chemically reactive sites without destroying its ability to assemble into chaperonins and 2D crystals. While a detailed three-dimensional structure of *S. shibatae* beta is not known, X-ray structures for homologous chaperonin subunits are known (See, e.g., Xu et al. And Diztel et al., supra.). Detailed transmission electron microscopic (TEM) analyses of *S. shibatae* chaperonins have also been reported (Trent et al., 1997, *Proc. Nat. Acad. Sci.* 94, 5383-5388). Using X-ray structures of homologous subunits and TEM analyses of *Sulfolobus* chaperonins, a hypothetical three-dimensional model for the beta chaperon can be produced, and used to guide genetic manipulations (See, e.g., Peitsch, M. C., 1995, *Bio/Technology* 13, 658; Guex, N., Peitsch, M. C., 1997, *Electrophoresis* 18, 2714; Guex, N., Diemand, A., Peitsch, M. C., 1999, *TiBS* 24, 364). At least two classes of beta mutants can be created using site-directed mutagenesis, many of which retain their ability to assemble into chaperonins that form 2D crystals (FIGS. 7B and 7D).

Figure 7E:
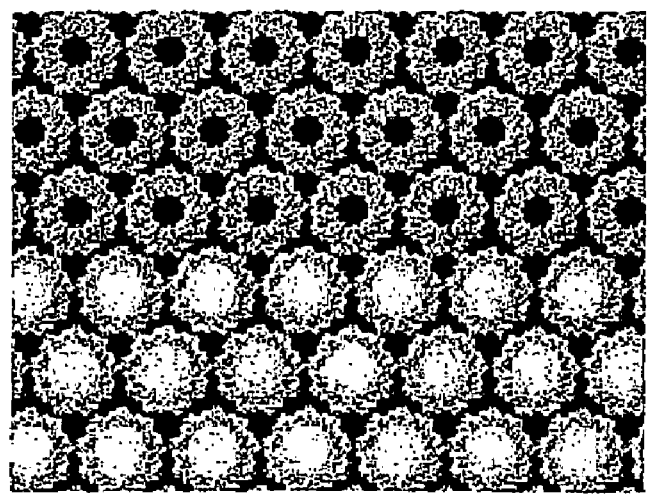
Figure 8A:
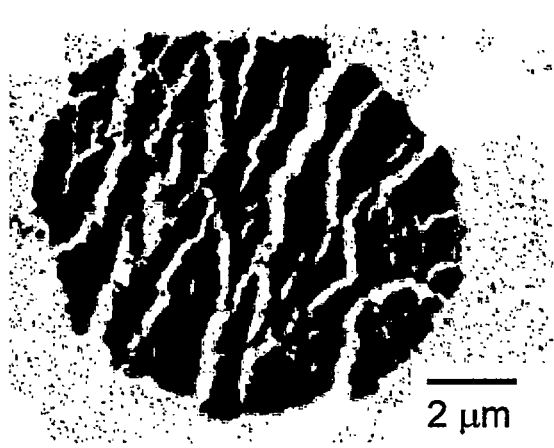
Figure 8B:
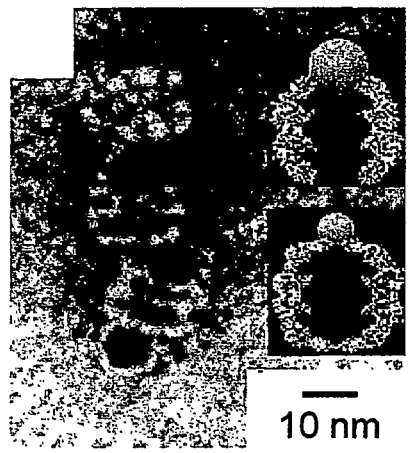
Figure 8C:
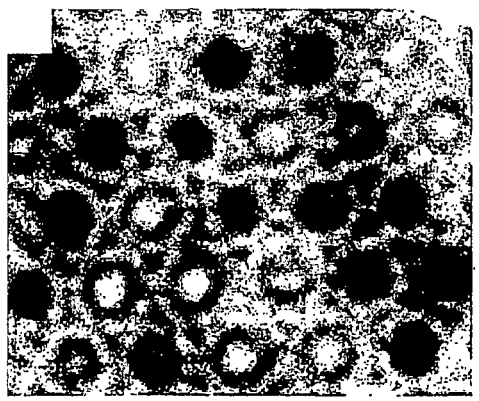
Figure 8D:
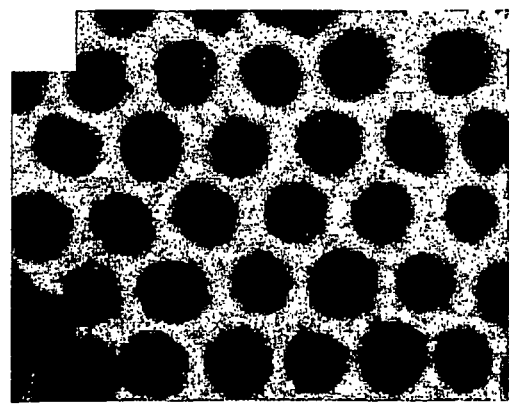

In two classes of beta mutants of *S. shibatae*, the single native cysteine residue in beta can be changed to a nonreactive residue, for example, an alanine residue, e.g., to prevent potential issues with folding and with assembly of mutant subunits. A cysteine can then placed at different solvent-exposed sites. The thiols of these cysteines can provide binding sites for soft metals including gold and zinc, as described in greater detail below. In one class of beta mutants of *S. shibatae*, the exposed cysteine is placed near the tip of a 28 amino acid loop on the apical domain of beta, which in the assembled chaperonin protrudes into the central cavity. This mutant chaperonin has a ring of reactive thiols with a diameter of approximately 3 nm on both ends (FIG. 7A). In the other class of beta mutants of *S. shibatae*, the protruding 28 amino acid loop was removed and placed the exposed cysteine on the apical domain itself. The mutant chaperonin assembled from this subunit has a ring of reactive thiols with a diameter of approximately 9 nm and an open pore into its central cavity (FIGS. 7D, 7E).

The beta subunit of *S. shibatae* proves to have sufficient structural plasticity in its apical domain to accommodate both the amino acid substitutions and deletions can be made without loss of its ability to form chaperonins and 2D crystals. Under reducing conditions both classes of beta mutants formed chaperonins that assembled into disk-shaped, hexagonally packed 2D crystals up to 20 μm in diameter (FIGS. 7B and 7D), the crystalline lattice ordering of which is confirmed by fast Fourier transformation (FFT) of the TEM images (FIG. 7D, inset).

Figure 2K:
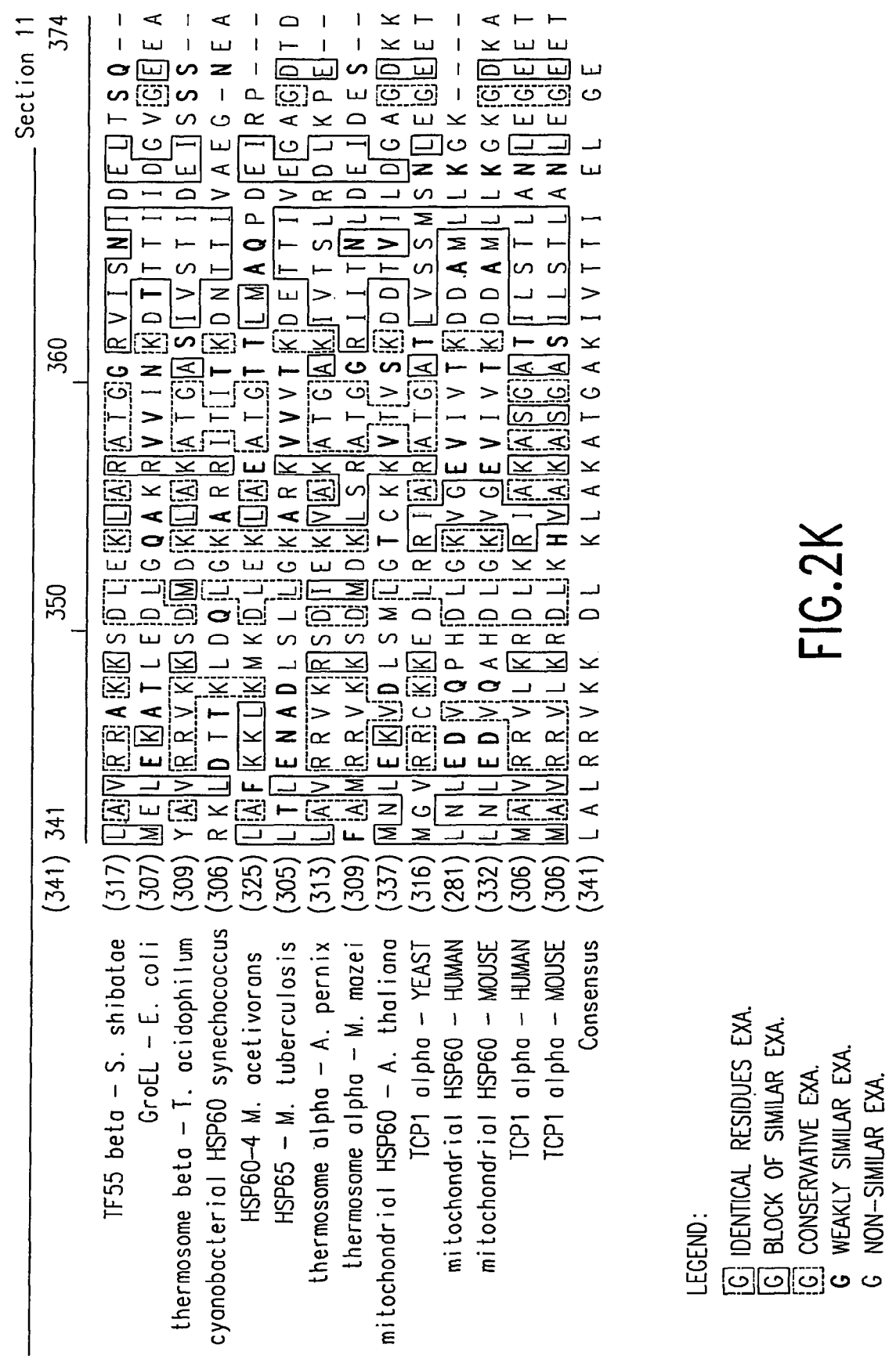
Figure 2L:
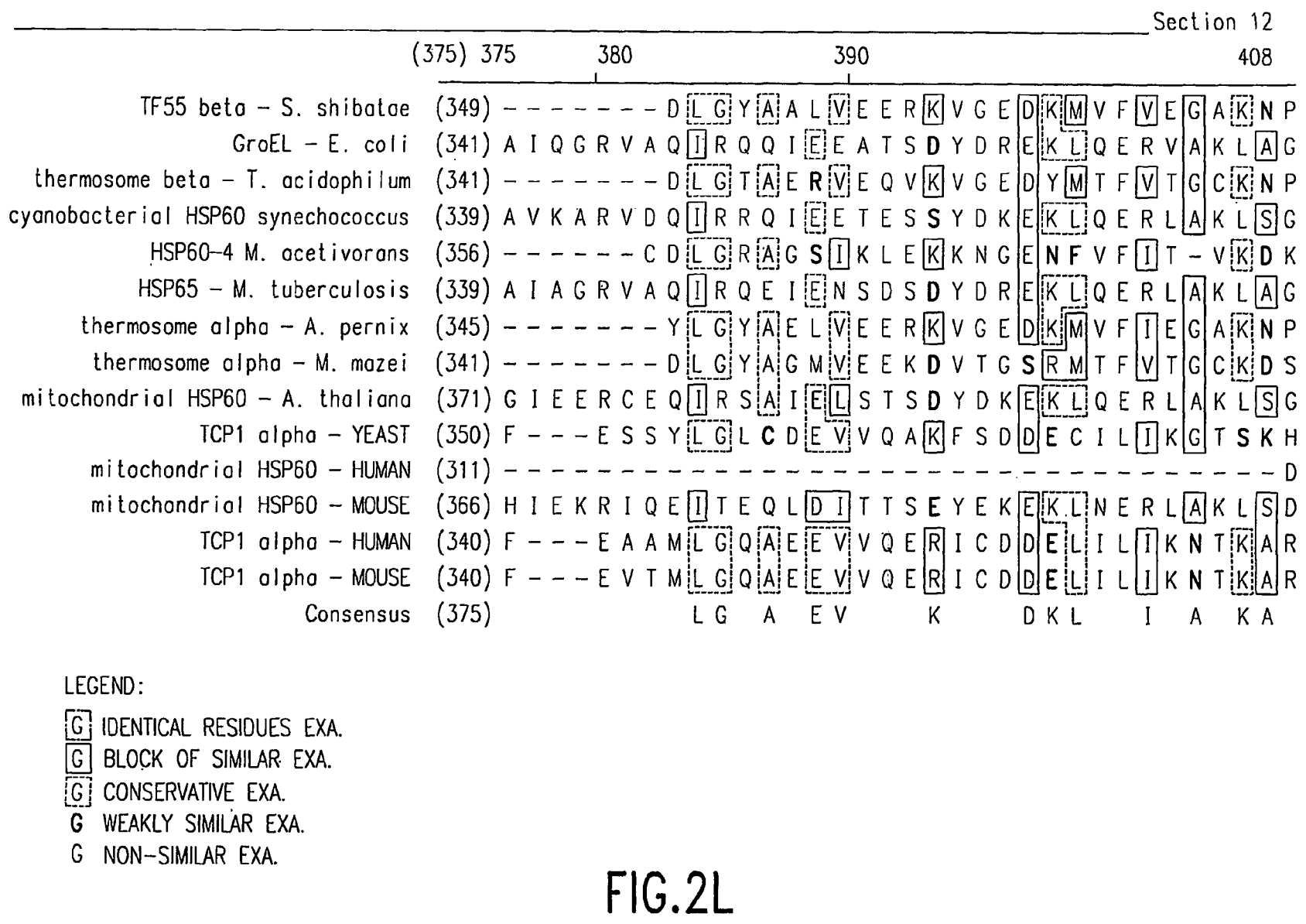
Figure 2M:
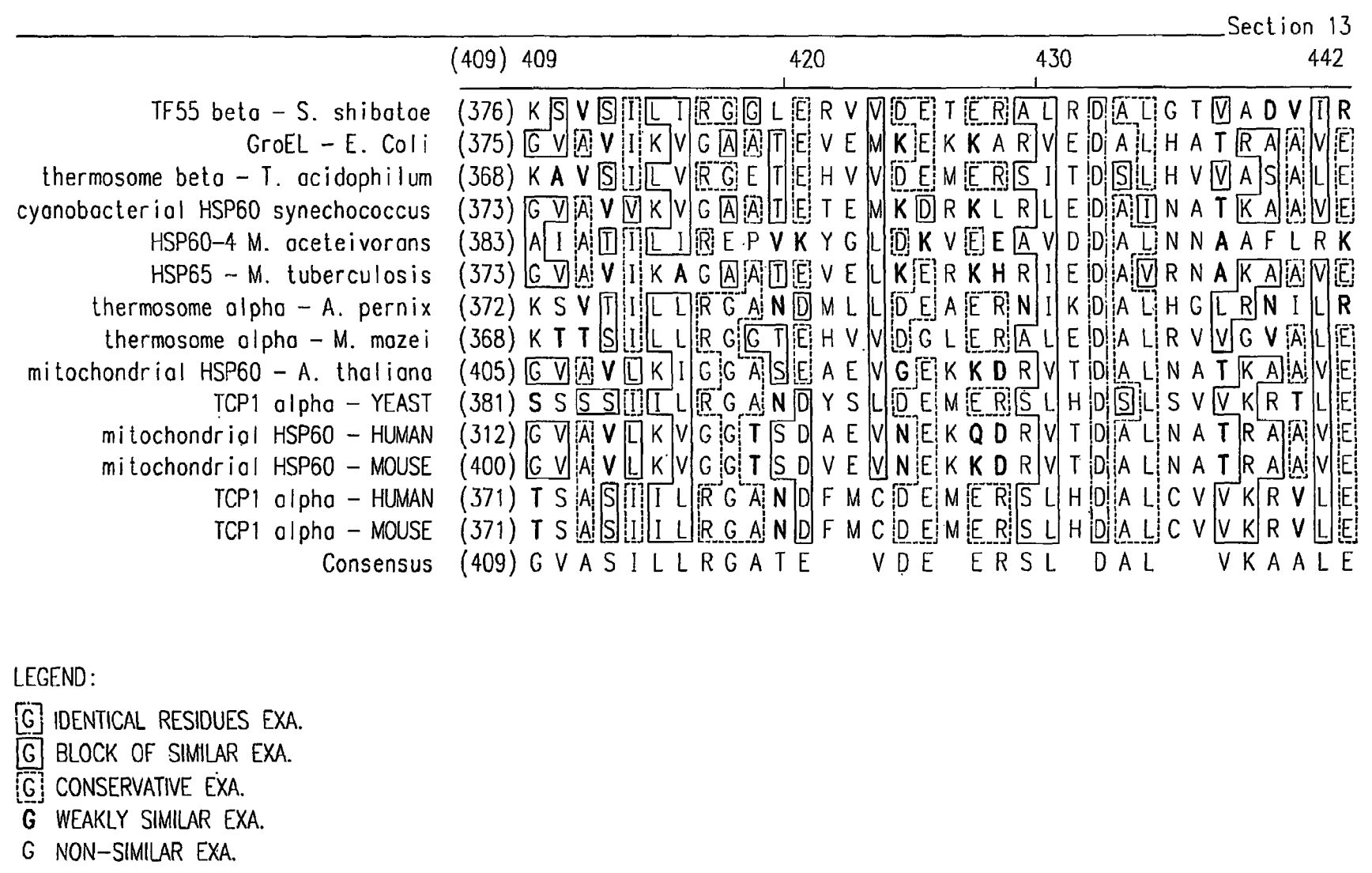
Figure 2N:
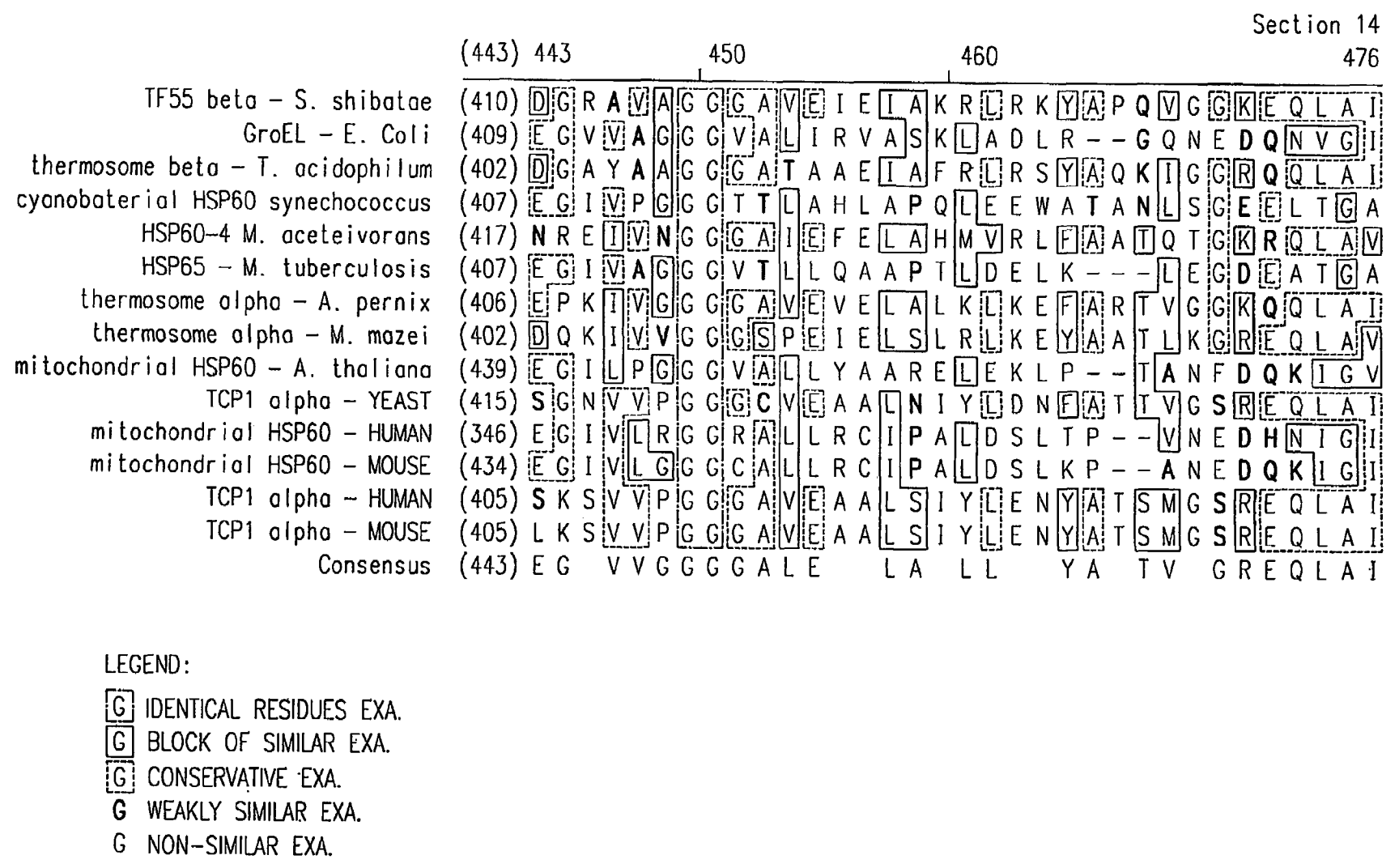
Figure 2P:
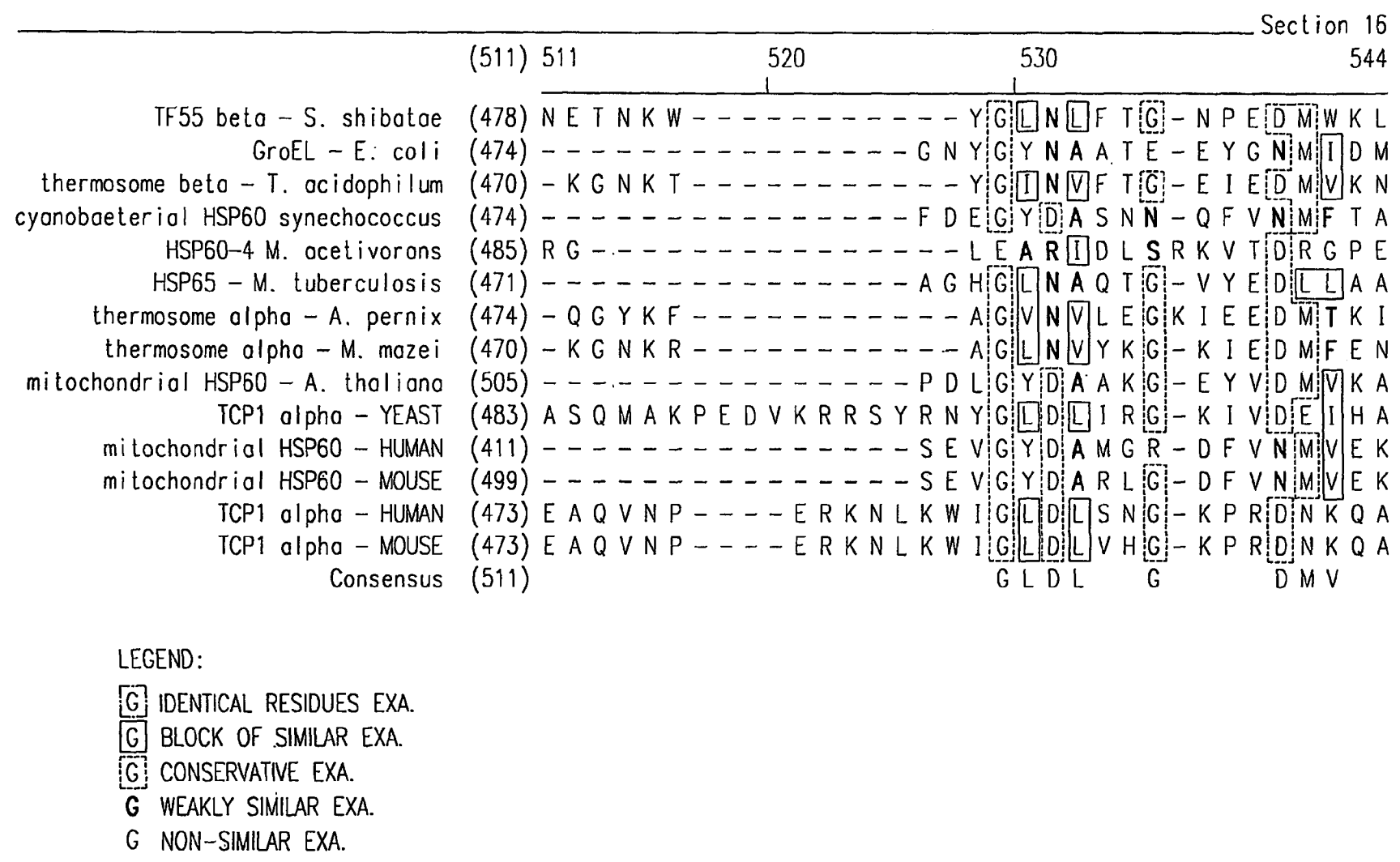
Figure 2Q:
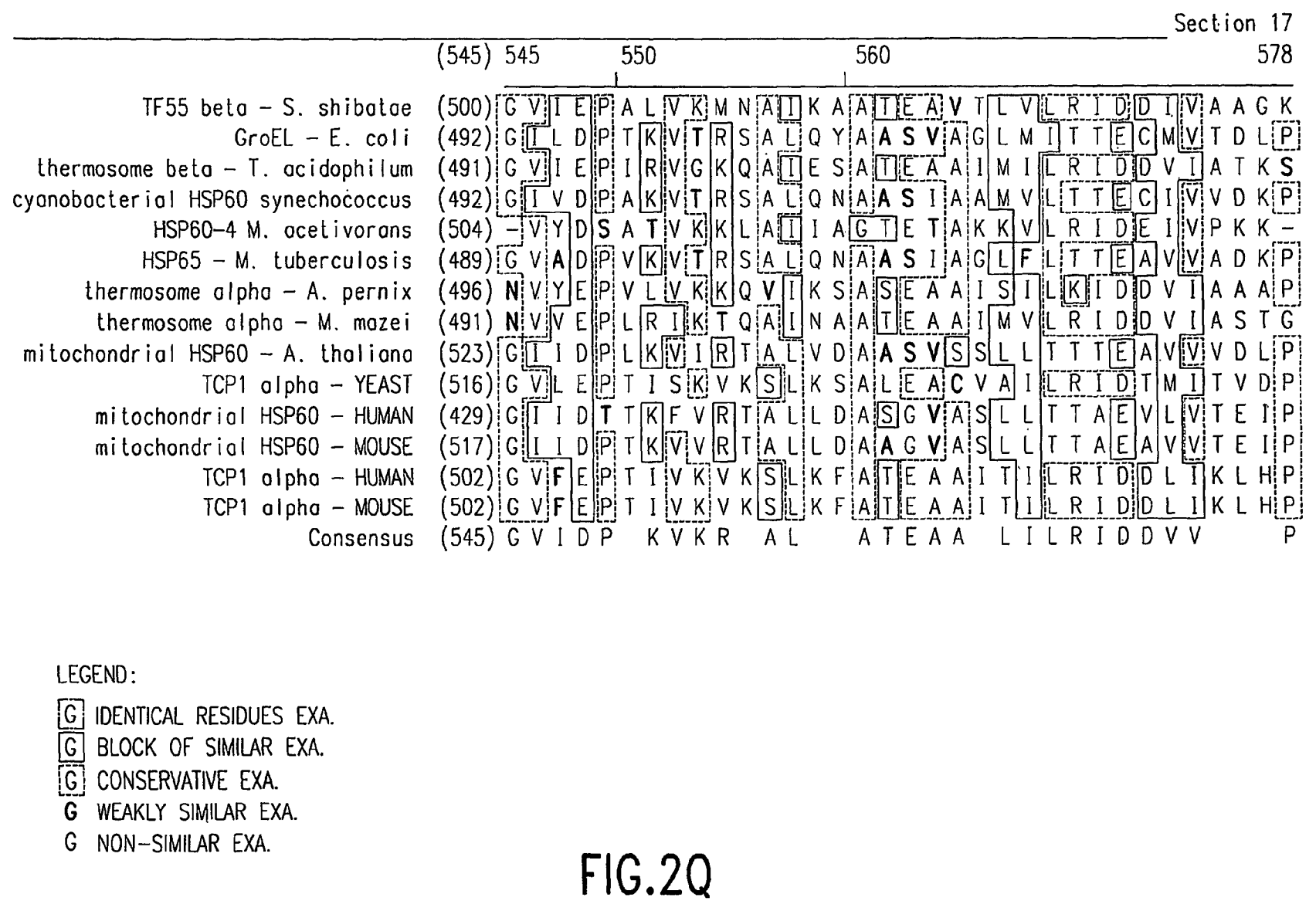

With knowledge of the sequences of the group I or group II chaperonin polypeptide, any number of mutations can be judiciously placed at one or more areas of the apical, intermediate and/or equitorial domains of the chaperonin polypeptide. As evidenced by the sequence alignment of FIGS. 2A-2B, the regions that have been manipulated in *S. shibatae* also exist in other species. Whatever mutations work in one species can be made to work in others. These corresponding regions of the sequence alignments can therefore serve as a guide in choice of manipulations to produce variants in other species. Thus, the many different varieties of binding sites that can be placed at different locations on a chaperonin can be exploited in the formation of the nanotemplates, nanostructures, nanoarrays and nanodevices of the present invention.

Formation of Chaperonins

The chaperonin polypeptide subunits are used to form the compositions and devices, e.g., nanotemplates, nanostructures, nanoarrays and nanodevices, of the present invention. Sources of chaperonin genes include but are not limited to bacterial chaperonin genes encoding such proteins as Gro ES/Gro EL; archaeal chaperonin genes encoding such proteins as TF55, TF56, alpha, beta, gamma, and cpn60s; mammalian chaperonins such as Hsp60, Hsp10, TCP-1, cpn60 and the homologues of these chaperonin genes in other species (J. G. Wall and A. Pluckthun, Current Biology, 6:507-516 (1995); Hartl, Nature, 381:571-580 (1996)). Additionally, heterologous genomic or cDNA libraries can be used as libraries to select or screen for chaperonins.

The sequences encoding the chaperonin polypeptides of interest (wild-type or mutated polypeptides) are incorporated into DNA expression vectors that are well known in the art. These circular plasmids typically contain selectable marker genes (usually conferring antibiotic resistance to transformed bacteria), sequences that allow replication of the plasmid to high copy number in *E. coli*, and a multiple cloning site immediately downstream of an inducible promoter and ribosome binding site. Examples of commercially available vectors include the pET system (Novagen, Inc., Madison, Wis.) and Superlinker vectors pSE280 and pSE380 (Invitrogen, San Diego, Calif.).

The steps in the self assembly of the chaperonins of the present invention can be achieved by methods that are well known in the art of recombinant DNA technology and protein expression in bacteria. First, the gene of interest is constructed and cloned into the multiple cloning site. In some cases, additional genes are also cloned into the same plasmid, for example, when the other polypeptide sequences are to be inserted. For example, restriction enzyme cleavage at multiple sites, followed by ligation of fragments, is used to construct deletions in the polypeptide sequences as listed above. Alternatively, a single or multiple restriction enzyme cleavage, followed by exonuclease digestion (EXO-SIZE, New England Biolabs, Beverly, Mass.), is used to delete DNA sequences in one or both directions from the initial cleavage site; when combined with a subsequent ligation step, this procedure produces a nested set of deletions of increasing sizes. Similarly, standard methods are used to recombine DNA segments from different chaperonin polypeptide genes, to produce genes for mutated chaperonin polypeptides. In general, these methods are also used to modify the N- or C-termini. Thus novel mutant polypeptides and combinations of polypeptides can be created to enable the formation of novel chaperonin polypeptide-based structures.

*E. coli* can serve as an efficient and convenient factory for the synthesis of the protein subunits from a variety of sources, including *E. coli* itself. In the next step, *E. coli* cells are transformed with the recombinant plasmid and the expression of the cloned gene is induced. The preferred hosts for production of the polypeptide is *E. coli* strain BL21 (DE3) and BL21 (DE3/pLysS) (available commercially from Novagen, Madison, Wis.), although other compatible recA strains, such as HMS174(DE3) and HMS174(DE3/pLysS) can be used. Transformation with the recombinant plasmid (Step 2) is accomplished by standard methods (Sambrook, J., *Molecular Cloning*, Cold Spring Harbor Laboratories, Cold Spring Harbor, N.Y.; this is also the source for standard recombinant DNA methods used in this invention.) Transformed bacteria are selected by virtue of their resistance to antibiotics e.g., ampicillin or kanamycin. The method by which expression of the cloned chaperonin polypeptide is induced (Step 3) depends upon the particular promoter used. A preferred promoter is plac (with a laci$^q$ on the vector to reduce background expression), which can be regulated by the addition of isopropylthiogalactoside (IPTG). A second preferred promoter is pT7N10, which is specific to T7 RNA polymerase and is not recognized by *E. coli* RNA polymerase. T7 RNA polymerase, which is resistant to rifamycin, is encoded on the defective lambda DE lysogen in the *E. coli* BL21 chromosome. T7 polymerase in BL21 (DE3) is super-repressed by the laci$^q$ gene in the plasmid and is induced and regulated by IPTG.

Typically, a culture of transformed bacteria is incubated with the inducer for a period of hours, during which the synthesis of the protein of interest is monitored. In the present instance, extracts of the bacterial cells are prepared, and the chaperonin polypeptides are detected, for example, by SDS-polyacrylamide gel electrophoresis. After the *E. Coli* have been given sufficient time to produce enough protein, the protein is isolated and purified.

The expression of the chaperonin polypeptides in *E. coli* allows for synthesis of large quantities of the proteins and also allows for the expression and in some cases the assembly of different components in the same cells. The methods for scale-up of recombinant protein production are straightforward and widely known in the art, and many standard protocols can be used to recover the wild-type and mutated chaperonin polypeptides from a bacterial culture.

Purification of the chaperonin subunits can be using standard methods. In one non-limiting example, a purification procedure comprises, either alone or in combination: 1) chromatography on molecular sieve, ion-exchange, and/or hydrophobic matrices; 2) preparative ultracentrifugation; and 3) affinity chromatography.

In an embodiment where the chaperonin polypeptides are thermostable extremophiles, the cell extracts can be heated for easier purification of the subunits. For example, the purification of the chaperonin beta subunit of *Sulfolobus* shibatae expressed in *E. coli* involves heating total cell extracts to 85° C. for 30 minutes, which precipitates most *E. coli* proteins, but the thermostable beta remains soluble. Therefore, heating and centrifuging cell extracts separates the beta subunit from most *E. coli* proteins, which simplifies further purification using ion exchange chromatography (Kagawa, H. K. et al., 1995, The 60 kDa heat shock proteins in the hyperthermophilic archaeon *Sulfolobus shibatae*. *J Mol Biol* 253, 712-25).

In one embodiment, several different types of chaperonin polypeptides components can be co-expressed in the same bacterial cells. Some assemblies of the polypeptides into chaperonins or higher order structures from purified wild-type or genetically modified subunits are extracted subsequent to limited in vivo assembly, using the methods enumerated above. An example of a higher order structure is a nanotemplate.

For forming the double-ringed structures of the chaperonins (and as seen later, the nanotemplates) of the present invention, the purified subunits are combined in vitro with $Mg^{2+}$ and ATP, ADP, AMP-PNP, GTP or ATPγS. In an alternate embodiment, purified chaperonins are assembled in vitro with $Mg^{2+}$ and ATP, ADP, AMP-PNP, GTP or ATPγS into the nanotemplates. In yet another embodiment, mixtures of purified subunits and purified chaperonins are combined in vitro with $Mg^{2+}$ and ATP, ADP, AMP-PNP, GTP or ATPγS to form the nanotemplates. The temperature or pH for formation will depend on the type and thermostability of the chaperonin polypeptides or chaperonins. For example, for the thermostable chaperonin beta subunit of *S. shibatae*, the temperature can be 75EC-85EC, while it may be lower for other types of polypeptides (e.g., less than 40EC). For a given chaperonin polypeptide, or nanotemplate, optimal conditions for assembly (i.e., concentration and proportion of $Mg^{2+}$ to ATP, ADP, AMP-PNP, GTP or ATPγS) are easily determined by routine experimentation, such as by changing each variable individually and monitoring formation of the appropriate products. For formation of the chaperonins and/or nanotemplates, any of $Mg^{2+}$, ATP, ADP, AMP-PNP, GTP or ATPγS can be present in an amount ranging from 1 mM, up to 10 mM, 20 mM, 30 mM or higher. See, e.g., Yoai et al., 1998, *Archives of Biochemistry and Biophysics* 356, 55-62, where filaments are formed in 5 mM Hepes buffer with 25 mM $MgCl_2$ and 1 mM ATP (total volume 300 µl). While it has been shown that the formation of chaperonins and/or nanotemplates from α and β subunits of *S. shibatae* does not depend on the presence of $K^+$, formation of the higher order structures from the subunits of other organisms may require the presence of $K^+$.

In yet another embodiment, the chaperonins or nanotemplates are formed in the absence of introduction of any of $Mg^{2+}$, ATP, ADP, AMP-PNP, GTP or ATPγS. At sufficiently high concentrations of the chaperonins, e.g., at concentrations of 2-5 mg/ml, or up to 30 mg/ml or more, some of the higher order structures, such as the nanotemplates, can spontaneously assemble (Quaite-Randall et al., 1995, *J. Biol. Chem.* 270, 28818-28823). The concentration of the chaperonins or chaperonin polypeptides in different embodiments is 0.1 mg/ml, 0.5 mg/ml, 1 mg/ml, 2, mg/ml, 5 mg/ml, 10 mg/ml, 30 mg/ml, 50 mg/ml or higher.

Alternatively, one or more extracts, for example crude bacterial extracts, containing the chaperonin polypeptides may be prepared, mixed, and assembly reactions allowed to proceed prior to purification.

In specific embodiments, some combination of both group I and group II chaperonins and/or chaperonin polypeptide subunits can be mixed and allowed to assemble in vivo or in vitro.

In another embodiment, the product of the expression of the chaperonin polypeptide and the resulting chaperonin is substantially free of other (non-chaperonin) proteins.

The methods and formulation conditions described herein for the formation of chaperonins can also be applied for the formation of the compositions and devices, e.g., the nanotemplates, nanostructures, nanodevices and nanoarrays, of the invention due to the ability of the chaperonin and chaperonin polypeptides to self-assemble under such conditions into the higher order structures.

Nanotemplates

The present invention provides methods for exploiting the subunits of chaperonins to form nanotemplates. A nanotemplate comprises one or more chaperonins, wherein at least one chaperonin is a mutant chaperonin comprising at least one mutated polypeptide. As such, a nanotemplate can comprise any number of chaperoning, in any proportion of mutant and wild-type chaperonins. In a non-limiting embodiment, the nanotemplate is a composite of only mutant chaperoning. The chaperonins comprising the nanotemplate can be group I chaperoning, group II chaperoning, or some combination thereof. In different embodiments, the nanotemplate comprises eukaryotic TCP-1, thermal factor 55, thermal factor 56 or GroEL chaperoning. In a preferred embodiment, the nanotemplate comprises HSP60s and variants. The choice of chaperonins to comprise the nanotemplate can be made depending on factors such as operating conditions. In a specific embodiment, if the nanotemplate is to experience high operating temperatures, the one or more chaperonins can be formed from extremophiles. The one or more chaperonins forming the nanotemplate can comprise 7, 8 or 9 subunits per ring, corresponding to seven-fold, eight-fold or nine-fold symmetric chaperoning, respectively. The chaperonins can comprise different types of subunits, for example, alpha subunits, beta subunits, gamma subunits or any combination thereof.

In one embodiment, the nanotemplates of the present invention are formed from chaperonin subunits and/or chaperonins combined in vitro with $Mg^{2+}$ and ATP, ADP, AMP-PNP, GTP or ATPγS. In an embodiment, assembly may require the presence of $K^+$. In an alternate embodiment, the nanotemplates spontaneously self-assemble, and are formed from chaperonin subunits and/or chaperonins combined in vitro in the absence of introduction of any of $K^+$, $Mg^{2+}$, ATP, ADP, AMP-PNP, GTP or ATPγS. At sufficiently high concentrations of the chaperoning, e.g., at concentrations of 2-5 mg/ml, or up to 30 mg/ml or more, some of the higher order structures, such as the nanotemplates, can spontaneously assemble (Quaite-Randall et al., 1995, *J. Biol. Chem.* 270, 28818-28823). The nanotemplate can be formed from chaperonins or chaperonin polypeptides at a concentration of 0.1 mg/ml, 1 mg/ml, 2 mg/ml, 5 mg/ml, 20 mg/ml or higher.

The length of filaments, one type of nanotemplate, can be manipulated according to whether ATP, ADP, AMP-PNP, GTP or ATPγS is used in forming the filament. Use of ATP, for example, can result in an extensive network of filaments, while using ADP, AMP-PNP, GTP or ATPγS can result in the formation of shorter. For example, with respect to formation of nanotemplates comprising mutant and/or mutant and wild-type TF55 α and β subunits of *S. shibatae*, chaperonins can be formed at concentrations of approximately 0.1 mg/ml, while at approximately 0.5 mg/ml, filaments are formed. Longer aligned filaments can be formed at concentrations of approximately 1.0 mg/ml. See, also, for example, Yaoi et al., 1998, Archives of Biochemistry and Biophysics 356, 55-62, and Trent et al., 1997, *Proc. Natl. Acad. Sci* 94, 5383-5388 for exemplary conditions that can be used to form structures like filaments of differing average lengths or two-dimensional arrays. Thus, the length of filaments can be controlled through manipulation and choice of formation conditions, with exact concentrations necessary for particular structures being routinely attainable.

The nanotemplates can have different architectural symmetries, which can be dictated through varying the formation conditions, or through directed binding or arrangement of the chaperonins relative to each other. As a result, the nanotemplate can have one-, two-, three-, four-, five-, six-, seven-fold architectural symmetry. Chaperonins of the invention can, for example, be used own to form nanofilaments (a nanotemplate with one-dimensional architectural symmetry) in the presence of Mg$^{2+}$ and nucleotides. These nanofilaments can cluster to form bundles of filaments that are microns in length and with bundle diameters of up to microns in thickness.

FIG. 5 shows that in the electron microscope individual HSP60s in the double-rings appear as black "blobs" (A, end view) or alternating dark and light bands (B, side view). These double-rings self-assemble into chains or porous tubes (C) and the tubes associate into filaments (D). FIG. 6 shows the organization of HSP60 rings into 2-dimensional crystals on a metal grid coated with lipid (A) and filament bundles arranged on a bed of rings (visible as spots in background) (B). In general, the choice of proportion of ATP to Mg$^{2+}$ affects the structure of the resulting chaperonin and nanotemplate, in terms of whether it forms a filament or an array. The nanotemplate can have long range two- or three-dimensional ordering as in an array with trigonal or hexagonal close packed architectural arrangement of the chaperonins through self-assembly (FIG. 6), as described in greater detail below.

The various architectural symmetries can also be dictated through directed arrangement of the chaperonins onto a substrate either through a masking technique or by directed binding (Whaley et al., 2000, *Nature* 405, 665-668, which describes peptides that bind to selectively to specific faces gallium arsenide, silicon or indium phosphide). An exemplary, non-limiting list of partial amino-acid sequences from clones that bind to different surfaces of GaAs and/or InP (Whaley et al., 2000, *Nature* 405, 665-668) includes:

| | |
|---|---|
| VTSPDSTTGAMA | (SEQ ID NO:16) |
| AASPTQSMSQAP | (SEQ ID NO:17) |
| AQNPSDNNTHTH | (SEQ ID NO:18) |
| ASSSRSHFGQTD | (SEQ ID NO:19) |
| WAHAPQLASSST | (SEQ ID NO:20) |
| ARYDLSIPSSES | (SEQ ID NO:21) |
| TPPRPIQYNHTS | (SEQ ID NO:22) |
| SSLQLPENSFPH | (SEQ ID NO:23) |
| GTLANQQIFLSS | (SEQ ID NO:24) |
| HGNPLPMTPFPG | (SEQ ID NO:25) |
| RLELAIPLQGSG | (SEQ ID NO:26) |

Whaley et al. also describes amino-acid sequences that bind silicon and not silicon dioxide. An example of an amino-acid sequence that binds to ZnS (102) (Lee et al., 2002, *Science* 296, 892-895) is:

| | |
|---|---|
| CNNPMHQNC | (SEQ ID No:27) |

A list of partial amino-acid sequences from clones that bind to Ag (Naik et al., 2002, *Nature Materials* 1, 169-172) includes:

| | |
|---|---|
| AYSSGAPPMPPF | (SEQ ID NO:28) |
| NPSSLFYRLPSD | (SEQ ID NO:29) |
| SLATQPPRTPPV | (SEQ ID NO:30) |

A list of partial amino-acid sequences from clones that bind to Au (Brown et al., 2000, *J. Mol. Biol.* 299, 725-735; Brown, S, 1997, *Nature Biotechnol.* 15, 269-272) includes:

| | |
|---|---|
| MHGKTQATSGTIQS | (SEQ ID NO:31) |
| ALVPTAHRLDGNMH | (SEQ ID NO:32) |
| PGMKASKSMRNQATPGMPSSLDLTWQAT | (SEQ ID NO:40) |
| PGMKMRLSGAKEATPGMSTTVAGLLQAT | (SEQ ID NO:41) |
| PGMIHVQKTAVQATPGMVNLTSPVKQAT | (SEQ ID NO:42) |
| ALDSPAGCLSFSMH | (SEQ ID NO:43) |

Other nanotemplates possessing shorter-range ordering include nanorings with rectangular, pentagonal, hexagonal or heptagonal architectural arrangements of chaperoning.

In a specific embodiment, the nanotemplate can comprise one or more wild-type and/or mutant chaperonins which serve as "spacers" in the nanotemplates. The spacer chaperonins can be confined to specific regions of the nanotemplate, and would not present specific binding sites for any of polypeptides, nanoscale materials or linker molecules. The spacers can therefore serve a similar function as a mask in semiconductor fabrication.

The generation of several different mutations of a given subunit can result in differences in dimension of the resulting chaperonins that comprise the nanotemplate. For example, a variant produced through the removal of a 28 amino acid loop at the apical end from the β subunit of *S. shibatae* resulted in a chaperonin with an expanded internal pore diameter of from 2.5 nm to 9 nm (see FIGS. 7B-D). This can be exploited in forming a nanotemplate with different mixtures of chaperonin subunit variants to present pores with different pore diameters for the binding of nanoscale objects such as nanoparticles and/or quantum dots.

The chaperonins and/or nanotemplates can differ according to the types of subunits and also the combinations of types of subunits used in formation. For example, in vitro alpha and beta subunits of *S. shibatae* form homo-oligomeric rosettasomes, while mixtures of alpha, beta, and gamma form hetero-oligomeric. It has also been found that beta homo-oligomeric rosettasomes and all hetero-oligomeric rosettasomes of *S. shibatae* associate into filaments. FIG. 15 shows the protein sequence alignment of *S. shibatae* TF55 alpha subunit (SEQ ID NO: 39), beta subunit (SEQ ID NO: 1) and gamma subunit (SEQ ID NO: 38). In vivo rosettasomes are hetero-oligomeric with an average subunit-ratio of 1α:1β:0.1γ in cultures grown at 75° C., a ratio of 1α:3β:1γ in cultures grown at 60° C., and a ratio of 2α:3β:0γ after 86° C. heat shock. Additionally, it has been observed that rosettasomes containing gamma were relatively less stable than those with alpha and/or beta subunits. A protein sequence alignment of the alpha, beta, gamma subunits of *S. shibatae* (see Figure), also provides useful information for positioning mutations on the chaperonin polypeptides. FIGS. 16A and 16B provide the DNA and amino-acid sequences of isolated *S. shibatae* TF55-γ.

The isolated chaperonin polypeptide subunits from a given organism can assemble into different types of nanotemplates and other higher order structures (Kagawa et al., 2002, *Molecular Microbiology*, in press). The isolated *S. shibatae* TF55 alpha subunit (SEQ ID NO: 39) alone forms discrete homo-oligomeric rosettasomes with the characteristic nine-fold ring member symmetry, and arrays of rosettasomes. The isolated *S. shibatae* TF55 beta subunit (SEQ ID NO: 1) forms filaments of rosettasomes and bundles of filaments. The isolated *S. shibatae* TF55 gamma subunit (SEQ ID NO: 38) does not assemble into rosettasomes, but forms amorphous aggregates and non-uniform round objects. Were seen in the TEM (FIG. 6C). Varying the proportions of the different subunits from a given organism can also result in the assembly of different higher order structure being formed (Kagawa et al., 2002, *Molecular Microbiology*, in press). A 1:1:1 mixture of *S. shibatae* TF55 alpha, beta, and gamma subunits results in heterooligomeric rosettasomes and filaments that were less bundled than the ones formed from isolated beta subunits. The 1:1 mixture of *S. shibatae* TF55 alpha and beta subunits results in filaments that are indistinguishable from filaments formed by the 1:1:1 mixtures of alpha, beta and gamma.

In one embodiment, the higher order structures, such as the nanotemplates and nanostructures, comprise at least one isolated *S. shibatae* TF55 gamma subunit. This embodiment of the invention can comprise mutated or wild-type chaperonin polypeptides. In a specific embodiment, the higher order structures, comprise at least one isolated *S. shibatae* TF55 gamma subunit and wild-type chaperonin polypeptides.

In another embodiment, the nanotemplate forms part of a coating or a nanofabric. Due to the capability of the chaperonins to self-assemble in an ordered arrangement on a fairly large length scale as compared to their pore diameters, they can be applied in these areas that could take advantage of the capability. Additionally, the resulting coating or nanofabric can be made to include optical, electric, magnetic, catalytic, or enzymatic moieties as functional units. These are produced through the selected placement of different nanoscale materials the apical domain of the chaperonin, e.g., near the pores of the nanotemplates, or on other binding sites of the chaperonin, or in between chaperonins. The inclusion of nanoscale material with the nanotemplates is discussed further in the section on nanostructures.

Changes in the subunit composition that can influence volume and reactivity of the central cavity of a chaperonin can also be exploited for various applications of the nanotemplates. While not wishing to be limited to a particular theory or mechanism, it is noted that the N- and C-termini of chaperonin subunits are believed to project into and occlude the central cavity. As such, because these termini can differ between subunits of a given species (e.g., rosettasome of *S. shibatae*), changes in subunit composition of the chaperonin can be used to impact on the central. Changes in the volume and binding properties of the central cavity of the chaperonin can therefore be dictated based on the composition of the chaperonin, which can be exploited in the formation of nanostructures which present different types of binding sites for nanoscale materials. In certain embodiments the N- and C-termini are deleted.

The assembly of chaperonin polypeptides, for example HSP60s, into such structures as rings, tubes, filaments, and sheets (2-D crystals) can be regulated chemically. The assembly can be manipulated by, for example, the proportion of ATP/$Mg^{2+}$ and/or by manipulating the concentration of these regions. HSP60-rings, tubes, and filaments can, for example, function as nano-vessels if they are able to absorb, retain, protect and release gases or chemical reagents, including reagents of medical or pharmaceutical interest. On a nanoscale, the filamentous structures, preferably HSP60 structures, are hollow and chemicals that are diffused or bound inside can be bound or released under programmed conditions at targeted locations.

The structures, e.g., rings, tubes, and filaments, can be induced to form ordered structures on surfaces. Under controlled conditions the chaperonins are observed to form 2-dimensional crystals on surfaces and the filament bundles may be oriented on surfaces. In an alternate embodiment, the nanotemplate functions as a multi-nanowell assay plate, or a single-molecule probe for DNA detection and hybridization.

Layers of interwoven chaperonin filaments may form a nano-fabric. Such fabrics may be induced to form on lipid layers and may ultimately be used to coat surfaces of materials. This may be of value in medical transplants in which the material could be coated with, e.g., an HSP60 fabric from the host and thereby limit the immune response against the transplant.

Fabrics or two-dimensional crystals of chaperonins comprising HSP60 can form nano-arrays of DNA or RNA by taking advantage of the intrinsic affinity of HSP60s for nucleic acids. Such arrays would represent an unprecedented density of DNA probes and thereby greatly amplify the density of information per unit area. Other kinds of probes based on other molecules that associate with HSP60 can also be developed.

For characterization, electron microscopy and electron probing methods (EDAX) can be used for investigating the contents of nano vessels, the continuity of nano-wires, the product of template experiments, and the nature of nanofabrics. Atomic force microscope (AFM) can be used in imaging and analyzing features of these nanotemplates. The DNA nano-arrays can be tested by hybridization methods.

Nanostructures

The present invention provides methods for forming nanostructures. The chaperonins offer many advantages over other molecules for the controlled assembly of complex architectures, in their ability to self-assemble. A nanostructure can be formed from a selective placement process involving self-assembly, or directed binding, depending on the desired resulting architectural arrangement. The steps in the formation of a nanostructure can include adding one or more nanounits comprising (i) at least one nanotemplate, (ii) at least one wild-type chaperonin, or (iii) a mixture of (i) and (ii) to a surface, and adding one or more nanounits comprising (i) at least one nanoparticle, (ii) at least one quantum dot, or (iii) a combination of (i) and (ii) to said surface. Any unbound nanounits are removed in order to maintain the desired architecture. Each of the addition steps are repeated as many times as necessary to result in a nanostructure. Optimal conditions for assembly (i.e., concentration and proportion of $Mg^{2+}$ to ATP, ADP, AMP-PNP, GTP or ATPγS) are easily determined by routine experimentation, such as by changing each variable individually and monitoring formation of the appropriate products. In alternate embodiment, the nanostructures assemble in the absence of any of $Mg^{2+}$, ATP, ADP, AMP-PNP, GTP or ATPγS. In yet other embodiments, assembly may require the presence of $K^+$.

The resulting nanostructures utilize proteins to control the assembly of structures that may, in certain embodiments, incorporate organic materials or inorganic materials such as metallic, semiconducting or magnetic nanoparticles (Bruchez et al., 1998, *Science* 281, 2013-16; Peng et al., 2000, *Nature* 404(6773), 59-61; Whaley et al., 2000, *Nature* 405: 665-68).

For the formation of a nanostructure, nanoscale materials can be combined with the chaperonin polypeptides and/or chaperonins under suitable conditions (e.g., concentration and proportion of $Mg^{2+}$, $K^+$, ATP, ADP, AMP-PNP, GTP or ATPγS). The nanoscale material (i.e., the nanoparticle or quantum dot) can be attached to the chaperonin and/or the polypeptide subunits at specific binding sites prior to assembly of the nanostructure. The nanoscale materials can be introduced before the formation of the nanotemplates, e.g., by being directly bound to a subunit, prior to assembly of the various subunits and/or chaperonins into the nanostructures. In an alternate embodiment, the nanoscale material is attached to specific binding sites after the nanotemplate is assembled. In such an embodiment, a nanotemplate is first formed, with the selected sites for binding of the nanostructures present on pre-determined locations of the nanotemplates, and then the nanostructures are introduced.

In another embodiment, the nanoparticles are coated with a coating that allows specific binding of the nanostructures to the pre-determined locations on the nanotemplates. FIG. 10A shows a gold particle derivatized with surface-accessible, thiol-reactive maleimide groups (monomaleimido Nanogold, Nanoprobes, Inc.). The nanogol quantum dots were covalently bound to the mutant beta subunit of S. shibatae with a cysteine presented as a binding site.

In other embodiments, the nanoscale materials are coated with an inorganic and/or organic compounds, a polymer, a protein, a peptide, hormones, antibodies, nucleic acids, receptors, reactive chemical groups, binding agents and the like. For example, the nanoscale materials can be coated with a polyethylene glycol compound containing chemically reactive amine groups.

In yet another embodiment, the nanoscale materials are coated with biotin or streptavidin. In a specific embodiment, the nanoscale materials are coated with bovine serum albumin (BSA) and biotin, and the streptavidin is located at one or more binding sites of the nanotemplate. In another example, amino acids, or small peptides are coated directly on the surface of the nanoscale materials, or are chemically linked to polymers or other type of macromolecules.

Examples of nanoscale materials include, but are not limited to, nanoparticles, such as gold, silver and other metal nanoparticle or composite nanoparticles of the metals; quantum dots (QD), including CdSe—ZnS, CdS, ZnS, CdSe, InP, InGaAs, CuCl, and InAs quantum dots, silicon nanocrystals and nanopyramids, silver nanoparticles; or magnetic quantum dots, e.g., nanomagnets, such as CoCu, FeCu, NiFe/Ag, and CoAg nanomagnets. The nanoscale materials can comprise one or more materials, or combinations of materials, such as transition metals, including gold, silver, zinc, cadmium, platinum, palladium, cobalt, mercury or nickel; alkali or alkaline earth metals, including sodium, potassium, calcium or cesium; group III elements, including, aluminum, gallium or indium; group IV elements, including, silicon, germanium, tin or lead; group V elements, including, phosphorous, arsenic, antimony, or bismuth; or group VI elements, including, sulfur, selenium or tellurium. The listed materials can be in any given combination. Examples of III-V compounds include GaAs or AlGaAs. The nanoscale material could also be a fullerene, a carbon nanotube, or a dielectric, polymeric, or semiconducting nanoparticle. In an alternate embodiment, flexible protein joints may be added to rigid carbon nanotubes to increase the diversity of possible forms while maintaining the functional features inherent in both kinds of nano-structures.

The size of the nanoscale material can be about 0.5 nm, 1 nm, about 10 nm, about 50 nm, about 100 nm, about 200 nm, or about 500 nm, or more. The size of the nanoparticles can depend on the location of the binding site on the nanotemplate. If the binding site is at an apical domain, or within the internal cavity of the chaperonin, then the size of nanoscale material may correlate with the pore diameter of the chaperonin to which it binds. FIGS. 7C and 7E show that the size of the nanoscale material that bind at the apical domain of chaperonins formed from variants of the beta subunits of S. shibatae. FIG. 7C shows an illustration of the 3-nm-pore 2D crystal (p312) indicating how 5 nm gold binds within the engineered pores. FIG. 7E shows an illustration of the 9-nm-pore 2D crystal (p312) indicating how 10 nm gold binds within the engineered pores. The nanoscale materials may also be located in interstitial regions of the nanotemplate, i.e., between the chaperonins. The nanoscale materials may be bound to more than one chaperonin, such as when the nanoscale material in present in an interstitial site. In another embodiment, the nanoscale material is located on top of a region of the nanotemplate, and serves as a type of "mask." In this embodiment, the nanoscale material can range up to 500 nm in size.

Morphologies of nanoparticles include, for example, nanopillars, nanocrystals, nanorods, nanotubes, nanowires, nanofilaments, nanofibers and composite metal/dielectric nanoshells.

In a specific embodiment, application of an electric field is used to disrupt the nanostructure.

In an alternate embodiment, differing amounts or proportions of ATP, ADP, AMP-PNP, GTP or ATPγS are used to disrupt the nanostructure or nanotemplates, or to cause the nanoscale material to become unbound from the nanostructure or nanotemplate.

In an embodiment, amino acid tails that do not inhibit their ability to assemble into rings and tubes are attached to the chaperonin polypeptides, e.g. i, HSP60s, and that allow the binding of the nanoscale materials inside the chaperonins structure, at an apical, equitorial or intermediate domain, or on other locations of the chaperonin.

Mutated chaperonin polypeptides, including HSP60s, can form nanometer or micron scale tubes and filaments or arrays containing metals or doped or undoped semiconductors, and could function as nano-wires, field-effect transistors, switches, diodes or logic devices. Given that metals can be attached to chaperonin polypeptides, their assembly into tubes would create a protein coated metal-cored conduit, i.e., a wire. By orienting and networking such wires nano-circuitry can potentially be created, which may be of value in the computer industry.

The nanostructures can also be incorporated into coatings with optical, electric, magnetic, catalytic, or enzymatic moieties as functional units.

Nanoarrays

A nanoarray is a nano scale or micro scale ordered arrangement of nanotemplates and/or nanostructures. A nanoarray, therefore comprises an ordered array of nanostructures. A nanoarray can have any type of long range packing symmetry, including 2-, 3-, 4-, or 6-fold packing symmetry. The nanoarray can be a one-dimensional structure, a two-dimensional array, or a three-dimensional array. In a specific embodiment, where the nanoparticles are dielectrics, a three-dimensional nanoarray can be a photonic bandgap crystal. Optimal conditions for assembly and crystallization of a nanoarray (i.e., concentration and proportion of $Mg^{2+}$ to ATP, ADP, AMP-PNP, GTP or ATPγS) are easily determined by routine experimentation, such as by changing each variable individually and monitoring formation of the appropriate products.

In both classes of beta mutants of S. shibatae, the single native cysteine residue in beta is changed to a nonreactive alanine to prevent potential problems with folding and with assembly of mutant subunits. The cysteine is then placed at different solvent-exposed sites. The thiols of these cysteines provide binding sites for soft metals including gold and zinc. In one class of beta mutants, the exposed cysteine was placed near the tip of a 28 amino acid loop on the apical domain of beta, which in the assembled chaperonin protrudes into the central cavity. FIGS. 7A-E shows the assembly of engineered HSP60s into nanoparticle array templates of the preferred embodiment. This mutant chaperonin has a ring of reactive thiols with a diameter of approximately 3 nm on both ends (FIG. 7A, left). In the other class of beta mutants, the protruding 28 amino acid loop is removed and placed the exposed cysteine on the apical domain itself. The mutant chaperonin assembled from this subunit has a ring of reactive thiols with a diameter of approximately 9 nm and an open pore into its central cavity (FIG. 7A, right). FIG. 7A (top left) shows a model of a mutated HSP60 beta subunit indicating apical loop cysteine placement by an arrow. The side view is consistent with both classes of chaperonin variants assembled from mutated beta subunits into two symmetrically stacked ninefold rings (FIG. 7A, center), while FIG. 7A (bottom left) shows a top view of beta chaperonin variant revealing 3 nm pore ringed by nine cysteines.

The TEM image of a negatively stained 2D crystal of the beta chaperonin variant with cysteines substituted into the apical pores is shown in FIG. 7B. The two-sided plane group p312 was assigned to the lattice through image analysis of micrographs of beta chaperonin 2D crystals from *S. shibatae* (Koeck et al., *Biochim. Biophys. Acta* 1429, 40-44). FIG. 7A (top right) Result of genetic removal of the 28 residue apical loop of beta and substitution of cysteine at the site fusing the α-carbon backbone. Residue deletion choices were made based on the structural data from the model in FIG. 7A (left) as indicated by the arrows. FIG. 7B (bottom right) shows a top view of chaperonin variant with 9 nm pore ringed by cysteines. FIG. 7B shows the 2D crystal of 9-nm-pore variant detailing apparent increase in pore size by the change in electron density within the negatively stained rings. Both samples were imaged at the same condenser defocus setting. The ordering of the crystal is illustrated by the FFT of the image. FIG. 7C shows an illustration of the 3-nm-pore 2D crystal (p312) indicating how 5 nm gold binds within the engineered pores. FIG. 7E shows an illustration of the 9-nm-pore 2D crystal (p312) indicating how 10 nm gold binds within the engineered pores.

The beta subunit *S. shibatae* proves to have sufficient structural plasticity in its apical domain to accommodate both the amino acid substitutions and deletions can be made without loss of its ability to form chaperonins and 2D crystals. Under reducing conditions both classes of beta mutants formed chaperonins that assembled into disk-shaped, hexagonally packed 2D crystals up to 20 µm in diameter (FIGS. 7B, 7D). The order within the crystalline lattices is illustrated by fast Fourier transformation (FFT) of the TEM images (FIG. 7B, inset) which produced an optical diffractogram expressing the periodicity.

To determine whether the thiol-containing 2D crystals of chaperonins acts as templates to bind and order nanoparticle QDs into arrays, commercially available gold nanoparticles (Ted Pella, Inc, Redding, Calif.) of different diameters can be used (FIG. 8). FIG. 8 shows gold quantum dot binding to engineered chaperonins and chaperonin templates. The uniform dispersion of these gold QDs in aqueous solution allows them to bind to hydrated chaperonin templates. To increase their likelihood of binding specifically to the reactive thiol of the cysteines, however, the nanoparticles can be passivated with the ligand bis(p-sulfonatophenyl)phenylphosphine (BSPP) Loweth, C. J., Caldwell, W. B., Peng, X., Alivisatos, A. P. & Schultz, P. G. (1999) DNA-based assembly of gold nanocrystals. (*Angew. Chem. Int. Ed.* 38, 1808-1812). BSPP displaces the citrate shell formed during synthesis of gold QDs (Novak, J. P., Nickerson, C., Franzen, S. & Feldheim, D. L. (2001) Purification of molecularly bridged metal nanoparticle arrays by centrifugation and size exclusion chromatography. (*Anal. Chem.* 73, 5758-5761) and thereby reduces nonspecific binding of the QDs to the protein template. The passivated gold QDs were reacted with the chaperonin templates attached to formvar-coated TEM grids (see Example 6.6) and imaged in TEM mode at 60 kV. At low magnifications the chaperonin 2D crystals were visualized in the TEM using the electron density of the gold QDs themselves. FIG. 8A shows a low magnification TEM image of 10 µm diameter unstained 2D crystal of 9 nm chaperonin variant with 10 nm gold QDs bound. Contrast is from gold QDs bound to the crystalline lattice of the underlying protein template. Drying can cause significant cracking and contributes to distortions and separation of regions of order within the array. FIG. 8B Higher-magnification stained TEM image of side views of 5 nm gold QDs tethered at the apical pores of the 3-nm-pore mutant chaperonins. At high magnification the chaperonin-gold interactions were visualized in the TEM by negative-staining samples with uranyl acetate. FIG. 8B (inset) shows a slab-view cutaway diagram of postulated orientation of 5 nm and 10 nm gold QDs bound at the apical pores of the two chaperonin variants. FIG. 8C shows a stained image of 5 nm gold QDs bound within the pores of the 3-nm-pore crystalline template. Occupied rings show the QDs (dark areas) surrounded and held in place by the outer protein density of the chaperonin pores. Empty rings have a brighter, less electron dense appearance. FIG. 8D shows ordered region of 10 nm gold bound to a 9-nm-pore template with similar area coverage as in FIG. 8C. The protein holding the QDs in place is more difficult to see due to the larger size of the 10 nm QDs. Individual chaperonins in solution were observed to bind gold QDs on one or both ends. The QDs are presumably held in place by multiple dative bonds formed between the gold surface and the thiols within the pores (FIG. 8B).

In control experiments, using chaperonin 2D crystals without exposed cysteines and with or without the amino acid loop deletions, the gold QDs appeared randomly distributed with no specific binding to the chaperonin crystals. On the surface of chaperonin 2D crystals with cysteines, however, the gold QDs bound specifically onto the pores (FIG. 8C) forming regions of order on the protein (FIG. 8D) separated from one another by the cracked regions that resulted from drying, indicating that the engineered chaperonin crystals function as templates for gold QDs in solution. These chaperonin templates were size selective when attached to substrates and appeared to bind QDs only on the exposed side. Templates made from beta mutants with cysteines added to the apical loop that formed 3 nm rings of reactive thiols ordered 5 nm (+/−3 nm) gold QDs, but did not order 10 nm (+/−2 nm) or 15 nm (+/−1 nm) gold QDs, which bound randomly on the template surface. Variations in size distribution of gold QDs are a result of the manufacturer's method of synthesis. The chaperonin templates with the loop removed and cysteines on the apical domains that formed 9 nm rings of reactive thiols ordered 10 nm (+/−2 nm) gold QDs, but 5 nm (+/−3 nm) and 15 nm (+/−1 nm) QDs bound randomly. This size selectivity is due to the accessibility and positioning of cysteine residues within the pores of the templates.

The precision of the center-to-center spacing of gold QDs ordered by the chaperonin templates was 16 nm (+/−2 nm, n=200) for both 5 and 10 nm gold QD arrays, as determined by TEM. This is consistent with the center-to-center spacing of the chaperonin pores in the underlying templates. The edge-to-edge spacing between QDs ranged from 6 to 10 mm for arrays made with 5 nm (+/−3 nm) QDs bound to 3-nm-pore chaperonin templates and from 4 to 6 nm for arrays made with 10 mm (+/−2 nm) QDs bound to 9-nm-pore chaperonin templates. This variation in spacing can be attributed to both the variation in the size of the gold QDs and to imperfections in the lattice of the chaperonin templates resulting from drying, cracking and dislocations within the arrays. The observed variation in QD spacing could be decreased with improved routes to QD synthesis having narrower size distributions. With more monodisperse QDs, the precision of center-to-center spacing in the gold nanoarrays should make it possible to tune the physical properties of the arrays by controlling the interparticle coupling using different sized QDs (Dujardin, et al., 2002, *Adv. Mater.* 14, 775-788).

The chaperonin nanotemplate arrays can also bind and order semiconductor QDs to form nanoarrays. Quantum dots of size 4.5 nm luminescent core-shell (CdSe—ZnS QDs) were used (Dabbousi, B. O. et al. (1997) (CdSe)ZnS core-shell quantum dots: Synthesis and characterization of a size series of highly luminescent nanocrystallites. *J. Phys. Chem. B* 101, 9463-9475). These QDs were reacted with 3-nm-pore chaperonin templates attached to glass or formvar substrates. Semiconductor QDs have low solubility in aqueous solutions. A QD suspension in trioctylphosphine/trioctylphosphine oxide (TOP/TOPO) diluted with butanol was reacted with dried chaperonin templates. Under these conditions the QDs bound to the cysteine-containing chaperonin templates (FIG. 9), but not appreciably to chaperonin 2D crystals without exposed cysteines (FIGS. 12 and 13). This is consistent with observations that Zn in the outer ZnS shell of CdSe—ZnS QDs binds solvent-exposed thiols (Chan, W. C. & Nie, S. (1998) Quantum dot bioconjugates for ultrasensitive nonisotopic detection. *Science* 281, 2016-2018).

Figure 9A:
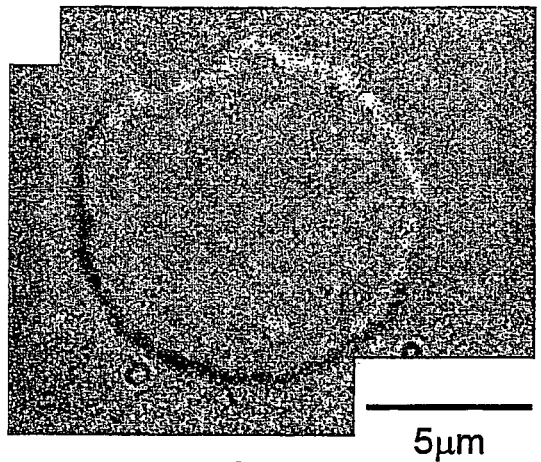
Figure 9B:
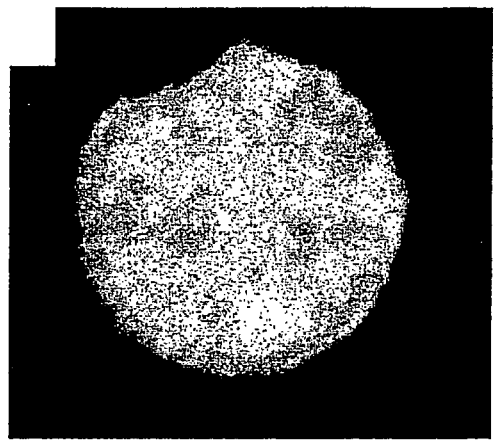
Figure 9C:
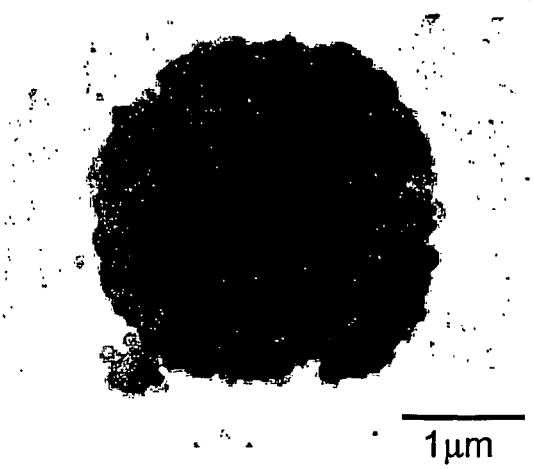
Figure 9D:
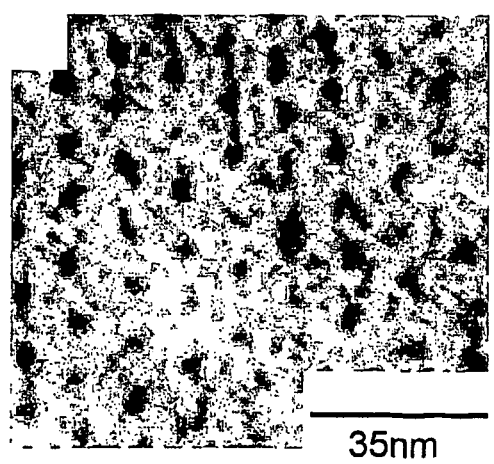

FIGS. 9A-D show the semiconductor QD nanoarray of a specific embodiment. FIG. 9A shows differential interference contrast (DIC) light micrograph of an 8 μm crystalline disc of 3-nm-pore template with 4.5 nm luminescent CdSe—ZnS QDs bound. The differential interference contrast (DIC) image of the QD-bound template (FIG. 9A) and the corresponding fluorescent image reveal that QDs bound to cysteine thiol retain their luminescent properties (Bruchez, M., Jr., Moronne, M., Gin, P., Weiss, S. & Alivisatos, A. P. (1998) Semiconductor nanocrystals as fluorescent biological labels. *Science* 281, 2013-2016). FIG. 9B shows both dry and rehydrated discs fluoresced indicating the QDs bound to the surface of the template. Selectivity for cysteine is confirmed using 2D crystals of beta variant without added cysteines which showed minimal QD binding (supporting information), while FIG. 9C shows low magnification TEM of an unstained array of CdSe—ZnS QDs. Image contrast is due to the bound semiconductor QDs. The mottled appearance of both the QD luminescence and the electron density of low magnification TEM images indicate that the QDs are unevenly distributed on the chaperonin templates. FIG. 9D shows higher-magnification image of same crystal revealing an ordered region of QDs bound to the protein lattice. At higher magnification of unstained samples, regions of ordered QDs are visible. These regions are separated by unoccupied regions where QDs did not bind to the protein template. This difference could be due to drying or to solvent effects of the butanol, both of which may alter the structure of the chaperonin template and the accessibility of the thiols. Water-soluble (silica-capped) CdSe—ZnS (Gerion, D. et al., 2001, "Synthesis and properties of biocompatible water-soluble silica-coated semiconductor nanocrystals," *J. Phys. Chem. B* 105, 8861-8871) QDs containing exposed thiol groups can bind more uniformly to hydrated chaperonin templates. The thiols on these QDs, however, can cause them to aggregate, which can result in the formation of defective arrays, in which case, it is preferable that the thiols be removed.

Nanoscale materials can be maneuvered into nanoarrays and nanostructures by first tethering them to chaperonin subunits and then ordered as the subunits assemble into chaperonins and 2D crystals (nanoarrays) or other nanostructures. As an example, commercially available 1.4 nm gold QDs derivatized with surface-accessible, thiol-reactive maleimide groups can be used (monomaleimido Nanogold, Nanoprobes, Inc., Yaphank, N.Y.). FIGS. 10A-D show an embodiment of a nanogold nanoarray. FIG. 10A shows a covalent attachment of 1.4 nm monomaleimido Nanogold to subunits of loop-minus beta variant of the beta subunit of *S. shibatae* through Michael addition of cysteine thiol to QD surface maleimide groups. FIG. 10A (right) shows possible arrangement of nine 1.4 nm covalently attached Nanogold QDs viewed at one end of a ring assembled from the derivatized subunit. FIG. 10B shows low magnification TEM image of a 2D crystalline array lightly stained with methylamine vanadate. The dark circular feature (arrow) demarks the analyzed area corresponding to the dashed-line spectrum in FIG. 10D and is the result of polymerization of mobile hydrocarbon which is attracted to the beam periphery. FIG. 10C shows higher-magnification brightfield EF-TEM image of the array revealing the ordered pattern of electron density that extends across the crystalline template. FIG. 10D shows XEDS spectra of bare carbon film (solid line) and Nanogold array (dashed line) from the probe outlined in FIG. 10B. Characteristic X-ray peaks from gold (Au $M_\alpha$~2 keV and Au $L_\alpha$~9.7 keV) confirm the presence of Nanogold within the array and the relative absence of Au on the support film.

These Nanogold QDs were covalently bound to the mutant beta subunit with cysteine inserted in place of the 28 amino acid loop in the apical domain (FIGS. 10A-D). Subunits, with Nanogold attached, assembled into chaperonins in the presence of ATP/$Mg^{2+}$ (FIG. 10A); these chaperonins form 2D crystals (FIGS. 10B and 10C). The binding of the Nanogold QDs and localization within the pores of the chaperonin crystals was confirmed by analytical TEM (FIGS. 10 and 11A-11C). FIGS. 11A-11C show an HAADF STEM imaging of Nanogold array. FIGS. 11A-11C show the diameter of the features contributing to the array periodicity is consistent with multiple QDs localized within each ring. The diameter of electron density observed within the chaperonin rings forming the array (FIGS. 11A-11C) is approximately 8 to 12 times that observed for a single 1.4 nm Nanogold QD (FIGS. 11A-11C). FIGS. 11A-11C show the periodicity from the Nanogold QDs localized within the rings extends across the entire crystal.

Ordered hexagonally spaced inclusions within the crystalline template were observed and determined to contain gold by imaging methylamine vanadate stained Nanogold samples in brightfield Energy Filtering (EFTEM) mode and by using X-ray Energy Dispersive Spectroscopy (XEDS) (FIGS. 10B-D). Oxygen plasma-treated carbon support films were used because they are more stable in an electron beam than formvar. Because the protein templates do not adhere to plasma-treated carbon as well as to formvar, samples were stained with methylamine vanadate to enable identification of their location on the substrate. The XEDS spectrum of the Nanogold array reveals distinct peaks due to gold that are well separated from vanadium and copper peaks from the stain and carbon/copper support respectively (FIG. 10D).

High Angle Annular Dark Field (HAADF) Scanning/Transmission Electron Microscopy (STEM) was used to image the gold localized and ordered within the Nanogold arrays (FIGS. 11A-C). Comparisons of bare Nanogold to Nanogold ordered into an array revealed that multiple Nanogold QDs were localized within the pores of the crystallized chaperonins (FIGS. 11A and 11B). The HAADF image of the Nanogold crystal also confirms the presence of gold within the chaperonin pores because contrast in HAADF imaging mode is atomic number dependent, and nearly independent of focus or thickness. An HAADF comparison of the diameter of bare Nanogold particles on carbon to the diameter of the gold nanoparticles contained within the central pores of the chaperonins that template the Nanogold into arrays reveals that the central diameters are approximately eight to twelve times that of the diameter of a single Nanogold QD. This observation is consistent with a model which suggests that each ring can contain up to nine Nanogold QDs (one per subunit). A lower magnification HAADF image of a similar area of an array reveals the ordering of the gold extends throughout the template (FIG. 11C). High resolution XEDS mapping attempts of the gold within the array were unsuccessful as the crystals were destroyed with the electron dose needed for such measurements. EELS (Electron Energy Loss Spectroscopy) mapping using the Au O shell was correspondingly unsuccessful because the V M shell edge lies in close proximity to the Au O shell and thus masks the gold signal. FIG. 12 shows a control experiment showing DIC (left) and fluorescent (right) images of non-cys-mutated chaperonin crystals after incubation with CdSe—ZnS QDs. The luminescence intensity of the fluorescent image is barely visible indicating minimal QD binding. FIG. 13 shows an Energy Filtered TEM thickness map of a typical 2D protein crystal. The intensity in this image is the ratio of the inelastic signal to the elastic signal and is proportional to the ration of t/λ where lambda is the mean free path for inelastic scattering and t is the local mass thickness. Regions of nominally uniform intensity indicate regions of nominally constant mass thickness. Increasing intensity indicates increased thickness. At the various regions and at the edges of the crystal one can observe clear transitions indicating that the crystal is composed of several layers.

Crystal thickness measurements (AFM and TEM) suggest that these crystals can be multilayered (supporting information), and are observed as crystals ranging from 1 to 5 layers (approximately 20 to 200 nm). The assembly of QDs into arrays by first covalently attaching them to subunits may create more defect-tolerant arrays because each chaperonin is composed of 18 subunits and therefore there are 18 chances for each site in the array to contain at least one QD. Likewise, the regions of QD ordering within arrays assembled this way appear to span the dimensions of the crystalline template and with fewer defects than previously observed. These types of arrays may find use in applications that demand longer range ordering than the 5 and 10 nm gold and semiconductor nanoparticle binding protocols allow.

The invention thus provides a hybrid bio/inorganic approach to nanophase materials organization where the functionality of proteins can be rationally engineered. Using structural information and recombinant biotechnology techniques, genetically engineered chaperonins can be made to function both as nanotemplates and as vehicles for controlled nanoscale organization of preformed QDs into ordered nanoarrays, e.g., arrays of nanomagnets. These nanotemplates, nanostructures, and nanoarrays can be "wired" together into functional nanodevices, for example by using genetics, as alternate binding sites may be engineered at different locations on the chaperonin.

Nanodevices

The possibility to induce asymmetry within the arrays by engineering alternate facets of the protein crystal is exploited in forming the nanodevices of the present invention. A nanodevice comprises at least one nanotemplate, at least one nanostructure, at least one nanoarray or some combination thereof. A nanodevice can, for example, be an electronic, semiconductor, mechanical, nanoelectromechanical, magnetic, photonic, optical, optoelectronic or biomedical device formed from at least one nanostructure, at least one nanoarray, and/or at least one nanotemplate.

In a specific embodiment, the nanostructures are organized into a nanodevice that functions with the chaperonins still present. In an alternate embodiment, the chaperonins are removed before the functioning of the nanodevice. The nanotemplate and nanostructure provide an organizational basis for attached molecules, nanoparticles and quantum dots. The attached nanoscale materials can be equally spaced at, e.g., 15 nm intervals, or selectively place at pre-determined sites. Taking advantage of the fact that enzymes (such as proteases) can be used to specifically remove the chaperonin, the nanotemplates can serve to leave behind pure material accurately placed on a surface at nano-scale resolution.

The steps in the formation of a nanodevice are similar to those for forming a nanostructure, except that the building blocks are nanotemplates, nanostructures, and/or nanoarrays. The steps can include adding one or more nanotemplates, nanostructures, nanoarrays, or some combination thereof to a surface, and then removing any unbound nanotemplates, nanostructures, or nanoarrays. The steps are repeated any desired number of times, with the choice of material introduction being changed at each step to build the desired nanodevice. Other masking techniques, e.g., semiconductor fabrication can also be combined with the present invention in the construction of the nanodevice.

There is no direct parallel of the present invention in the semiconductor manufacturing industry. The use of protein-based templates that self assemble into highly ordered structures allow of the engineering of semiconductor materials on a size regime much smaller than that currently attainable. Further, given the diversity of the chaperonin system (e.g., its ability to bind other biomolecules such as lipid and DNA/RNA) the compositions and devices of the invention can also be utilized in a biomedical, e.g., biomedical device, context.

The invention further provides methods to selectively deposit nanoparticles or quantum dots in an ordered array onto inorganic substrates. DNA manipulation and genetic engineering of the genes that code for chaperonins can be used to generate specificity in molecular recognition at defined sites within the protein. For example, by introducing cysteine residues into the protein, it can specifically bind colloidal gold molecules through dative bonding between the sulfhydryl (SH) moeity of Cys and Au0. This allows for the organization of gold nanoparticles into ordered arrays onto substrates. After organizing the gold onto the surface, the protein can be removed using a reactive ion cold plasma, leaving the patterned gold in place on a clean surface (FIG. 14), thereby producing a nanodevice of the invention. The HSP60s bound with proteins or peptides are capable of releasing the bound proteins or peptides in the presence of adenosine triphosphate (ATP) or acidic conditions (Udono and Srivastava, 1993, *J. Exp. Med.* 178, 1391-1396). xxx With advances in microbial genetics, for example using phage and cell surface display to identify inorganic binding peptide sequences (Whaley et al., *Nature* 405, 665-668), the usefulness of this system extends beyond soft metals to other materials by, for example, the addition of sequences back into the loop region that was removed.

Examples of additional, non-limiting applications of the nanodevices include field emitters, sensors, optoelectronic and all-optical switches, lenses, probes, lasers, nanoelectromechanical systems (NEMS), circuitry and nanoelectronics, nanomachines (e.g., by attaching nanomotors), neural networks (nanoelectrodes for connections), nanocomputers, quantum computers, high-density magnetic memory or storage media, photonic crystals, nanocrystal antennas, multi-nanowell assay plates, nanocatalysts (e.g., palladium), nanopores for single-molecule DNA sequencing, amplifiers for telecommunications (approximately 7 nm PbSe and PbS quantum dots have a tunable gap near 1500 nm). Applications include, for example, memory or storage devices (e.g., hard-disk drive read heads, magnetic RAM), magnetic field sensors, magnetic logic devices, logic gates, and switches.

Further applications can also include, for example, biochip applications. Quantum dots in a biochip, for example, can each account for at least one or several data bits. The position of a single electron in a quantum dot can attain several states, so that a quantum dot can represent a byte of data. In an alternate embodiment, a quantum dot can be used in more than one computational instruction at a time.

Other applications of quantum dots include nanomachines, neural networks, and high-density memory or storage media.

In an alternate embodiment, the nanodevice, nanotemplate or nanoarray functions as a single-molecule probe for DNA detection, hybridization, and sequencing.

Polymer microspheres with uniformly embedded polymers have applications as, for example, active fluorescent building blocks in flat panel displays and luminescent labels in biological detection. This application is achieved by forming a nanodevice comprising a nanoarray of embedded polymer nanoparticles Still further applications relate to molecular motors, e.g., molecular motors in a biomedical context.

6. EXAMPLES

Example 6.1

Models

A homology model for S. shibatae HSP60beta was made using the web-based service Swiss Model (Web citation deleted at Examiner's direction). Seven PDB entries of solved structures of homologous proteins were used as templates scoring between 48% and 64% sequence identity in pairwise alignment with native S. shibatae beta. The structure was relaxed in vacuo with the GROMOS96 force field. Symmetry operations were applied to the subunit to form nine-fold symmetrical rings which were assembled into 18-mer chaperonins. All models were constrained by dimensions observed for different chaperonin views as measured in the TEM.

Example 6.2

Cloning and Sequencing of the Gamma Gene of S. shibatae

The gamma gene was amplified by the polymerase chain reaction (PCR) method from S. shibatae genomic DNA purified using Qiagen Genomic Tips (Qiagen). PCR primers (P1: 5'-ATGAACTTAGAGCCTTCCTAT-3' (SEQ ID NO:33) and P2: 5'-TTAACTCCATAAGAAACTTGT-3') (SEQ ID NO:34) were based on previously published partial gamma sequence information (Archibald et al., 1999, Current Biology 9, 1053-1056). The inverse-PCR method (Ochman et al., 1988, Genetics 120, 621-623) was used to obtain the complete gamma gene and its flanking regions. Briefly, AseI digested genomic DNA was circularized by self-ligation and a 1.2 kbp fragment was obtained by PCR amplification after 25 cycles (30 sec at 94° C., 1 min at 50° C., and 1 min at 72° C.), using Vent polymerase (New England BioLabs). The PCR fragment was ligated into pBluescript SK(+) (Stratagene) to obtain a plasmid which was transformed into E. coli (strain DH5a). The gamma gene was sequenced on both strands by the dideoxy-chain termination method (Sanger et al., 1977, Proc. Natl. Acad. Sci. USA 74, 5463-5467), and analyzed using the program DNASTAR (DNASTAR, Inc.). FIGS. 16A and 16B show the DNA sequence (SEQ ID NO: 37) and amino-acid sequence for S. shibatae gamma subunit (SEQ ID NO: 38).

Example 6.3

Expression of the Gamma Gene of S. shibatae in E. coli

The complete gamma gene PCR was amplified from S. shibatae genomic DNA using a pair of primers (Primer 1: 5' GAAAGAACATATGGCCTATTTATTAA-GAGAAGGAACACAG-3' (SEQ ID NO:35) and Primer 2: 5'-TAAAGTACTCGAGAAAAC-CTAAATAAAATAATCATATCTTAAC-3' (SEQ ID NO:36)). This fragment was cloned into the Nde I and Xho I sites of the plasmid vector pET22b (Novagen). Expression in E. coli strain BL21 (DE3) "codon plus" in LB media containing 50 mg/ml carbenicillin (Sigma) was under isopropyl β-D thiogalactopyranoside (IPTG) regulation. The alpha and beta genes were similarly expressed (Kagawa et al., 1995, J. Mol. Biol. 253, 712-725).

Example 6.4

Genetic Modifications

A standard PCR mutagenesis method as described in Current Protocols in Molecular Biology was followed to introduce cysteine residues and to delete the portions of DNA coding for the apical loop. All mutant subunits were purified as described in the text and in corresponding references.

Example 6.5

Chaperonin Assembly and Crystallization

Chaperonins were assembled from purified subunits with the concomitant formation of two-dimensional crystals in solution, without the need of an interacting interface. Concentrated stock solutions of ATP and $MgCl_2$ were added to purified subunits (1.5 mg/ml, 25 μM in 25 mM HEPES, 3.5 mM TCEP) such that the final ATP concentration is 4 mM and the final $MgCl_2$ concentration is 10 mM. The crystallization solution was incubated at 4° C. overnight after which crystals are observed as a white precipitate.

Example 6.6

Quantum Dot Nanoarray Formation

For gold QD binding, crystalline protein templates were applied to formvar coated 200 mesh copper TEM grids and gold QDs were bound by floating the sample-side of the grid on 5 μl drops of passivated QD sols, wicking away with filter paper and washing by floating on HAT buffer (25 mM HEPES, 0.1% sodium azide, 3 mM tris[2-carboxyethyl] phosphine hydrochloride, pH 7.5) for 10 minutes. This process was repeated up to 10 times as more applications increases the site occupation on the template. The 10 nm gold QDs bound better with fewer applications than the 5 nm QDs.

After 10 applications the 3-nm templates were considerably broken up. Samples were viewed in a LEO 912 AB TEM at 60 kV. All quantitative image analysis was performed using AnalySIS 3.5 (Soft Imaging System Corp., Lakewood, Colo.).

Semiconductor QDs were bound and imaged in a similar manner as gold QDs with the exception that templates are applied to TEM grids, were washed with water, dried and re-swelled with butanol before QD binding. For light microscopy, the crystals were applied to a formvar coated glass slide, rinsed with water, dried, rinsed with butanol, and covered with a coverslip. A dilute slurry of CdSe—ZnS QDs in TOP/TOPO/butanol was passed over the crystals by capillary action and thoroughly rinsed with butanol, and imaged in brightfield, DIC and fluorescence modes on a Leica DMR/X microscope.

Nanogold arrays were fabricated in the following manner. Subunits of the loopless mutant with the cysteine insertion are reacted with an excess of Nanogold as per the instructions supplied by the manufacturer. The Nanogold-tagged subunits were separated from unreacted protein and excess Nanogold using gel filtration chromatography (BioRad BioGel P-10), concentrated to 1.5 mg/ml and assembled into rings and 2D crystals as described above.

Samples were applied to carbon coated grids that were briefly treated with an oxygen plasma to enhance protein adhesion to carbon. Specimens were analyzed at room temperature using a double-tilt Be stage in a FEI TecnaiF20 AEM. The instrument was operated in the Transmission (TEM), Scanning Transmission (STEM), High Angle Annular Dark Field (HAADF) and Energy Filtering (EFTEM) modes at 200 kV using a Schottky Field Emisson Gun (FEG) electron source. All X-ray Energy Dispersive Spectroscopy (XEDS) measurements were made using an EDAX ultra thin window Si(Li) detector having a FWHM of ~150 eV at Mn $K^\alpha$, while energy filtering and electron spectroscopy was accomplished using a Gatan GIF2000 imaging electron energy loss spectrometer. Nominal probe sizes used during the study varied between 0.5-500 nm, depending upon the nature of the measurements/observations.

6. MISCELLANEOUS

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

The invention claimed is:

1. An isolated chaperonin polypeptide, comprising a TF55 beta polypeptide from *Sulfolobus shibatae* according to SEQ ID NO: 1 which comprises a deletion of amino acids 254 through 281.

2. The isolated chaperonin polypeptide of claim 1, wherein the deleted amino acids 254 through 281 are replaced with a cysteine.

3. The isolated chaperonin polypeptide of claim 2 which binds a gold nanoparticle.

4. The isolated chaperonin polypeptide of claim 2, further comprising a cysteine at position 299 of SEQ ID NO:1 which is substituted with an alanine.

5. The isolated chaperonin polypeptide of claim 1, further comprising a nanoparticle-binding peptide which replaces the deleted amino acids 254 through 281, wherein the nanoparticle-binding peptide is any one of SEQ ID NOS:16-31.

6. The isolated chaperonin polypeptide of claim 5, wherein the nanoparticle-binding peptide is any one of SEQ ID NOS: 16-26 which binds a gallium (III) arsenide (GaAs) nanoparticle.

7. The isolated chaperonin polypeptide of claim 5, wherein the nanoparticle-binding peptide is SEQ ID NO:27 which binds a zinc sulfide (ZnS) nanoparticle.

8. The isolated chaperonin polypeptide of claim 5, wherein the nanoparticle-binding peptide is any one of SEQ ID NOS: 28-30 which binds a silver nanoparticle.

9. The isolated chaperonin polypeptide of claim 5, wherein the nanoparticle-binding peptide is SEQ ID NO: 31 which binds a gold nanoparticle.

10. The isolated chaperonin polypeptide of claim 5, further comprising a cysteine at position 299 of SEQ ID NO:1 which is substituted with an alanine.

11. The isolated chaperonin polypeptide of claim 1, comprising a TF55 beta polypeptide from *Sulfolobus shibatae* according to SEQ ID NO:1 which comprises a deletion of amino acids 254 through 281, and further comprising an inserted cysteine which replaces the deleted amino acids 254 through 281, and further comprising a substitution of an alanine at position 299 of SEQ ID NO:1.

12. The isolated chaperonin polypeptide of claim 11 which binds a gold nanoparticle.

13. The isolated chaperonin polypeptide of claim 1, comprising a TF55 beta polypeptide from *Sulfolobus shibatae* according to SEQ ID NO:1 which comprises a deletion of amino acids 254 through 281, and further comprising a nanoparticle-binding peptide which replaces the deleted amino acids 254 through 281, wherein the nanoparticle-binding peptide is any one of SEQ ID NOS:16-31, and further comprising a substitution of an alanine at position 299 of SEQ ID NO:1.

14. The isolated chaperonin polypeptide of claim 13, wherein the nanoparticle-binding peptide is any one of SEQ ID NOS:16-26 which binds a gallium (III) arsenide (GaAs) nanoparticle.

15. The isolated chaperonin polypeptide of claim 13, wherein the nanoparticle-binding peptide is SEQ ID NO:27 which binds a zinc sulfide (ZnS) nanoparticle.

16. The isolated chaperonin polypeptide of claim 13, wherein the nanoparticle-binding peptide is any one of SEQ ID NOS:28-30 which binds a silver nanoparticle.

17. The isolated chaperonin polypeptide of claim 13, wherein the nanoparticle-binding peptide is any one of SEQ ID NO:31 which binds a gold nanoparticle.

* * * * *